US010159725B2

(12) United States Patent
Fritsche et al.

(10) Patent No.: US 10,159,725 B2
(45) Date of Patent: Dec. 25, 2018

(54) COMPOSITION OF TUMOR-ASSOCIATED PEPTIDES AND RELATED ANTI-CANCER VACCINE FOR THE TREATMENT OF GASTRIC CANCER AND OTHER CANCERS

(75) Inventors: Jens Fritsche, Tuebingen (DE); Toni Weinschenk, Aichwald (DE); Steffen Walter, Reutlingen (DE); Peter Lewandrowski, Tuebingen-Hirschau (DE); Harpreet Singh, Tuebingen (DE)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 1102 days.

(21) Appl. No.: 13/635,898

(22) PCT Filed: Mar. 16, 2011

(86) PCT No.: PCT/EP2011/053996
§ 371 (c)(1),
(2), (4) Date: Jan. 10, 2013

(87) PCT Pub. No.: WO2011/113872
PCT Pub. Date: Sep. 22, 2011

(65) Prior Publication Data
US 2013/0115188 A1 May 9, 2013

Related U.S. Application Data

(60) Provisional application No. 61/315,715, filed on Mar. 19, 2010.

(30) Foreign Application Priority Data

Mar. 19, 2010 (GB) .................................... 1004575.5

(51) Int. Cl.
*G01N 33/50* (2006.01)
*A61K 39/00* (2006.01)
*C07K 14/47* (2006.01)

(52) U.S. Cl.
CPC ...... *A61K 39/0011* (2013.01); *C07K 14/4748* (2013.01); *A61K 2039/55511* (2013.01); *A61K 2039/55522* (2013.01); *G01N 33/5005* (2013.01)

(58) Field of Classification Search
None
See application file for complete search history.

(56) References Cited

U.S. PATENT DOCUMENTS

| 7,994,276 B2 | 8/2011 | Singh et al. |
| 8,080,634 B2 | 12/2011 | Singh et al. |
| 2007/0218512 A1 | 9/2007 | Strongin et al. |
| 2009/0136528 A1 | 5/2009 | Singh et al. |
| 2009/0148400 A1 | 6/2009 | Singh et al. |
| 2009/0274714 A1 | 11/2009 | Singh et al. |
| 2010/0040641 A1 | 2/2010 | Tsunoda et al. |
| 2011/0229504 A1* | 9/2011 | Fritsche ............. A61K 38/1709 424/185.1 |
| 2011/0229505 A1* | 9/2011 | Fritsche ............. A61K 38/1709 424/185.1 |
| 2011/0318380 A1* | 12/2011 | Brix .................... A61K 39/0011 424/193.1 |

FOREIGN PATENT DOCUMENTS

| EP | 1538163 A2 | 6/2005 |
| EP | 1760089 A1 | 3/2007 |
| EP | 2111867 A1 | 10/2009 |
| EP | 2119726 A1 | 11/2009 |
| WO | 2000020029 A1 | 4/2000 |
| WO | 03100432 A2 | 12/2003 |
| WO | 2007005635 A2 | 1/2007 |
| WO | 2009/015842 A2 | 2/2009 |
| WO | 2009015841 A1 | 2/2009 |
| WO | 2011/113819 A2 | 9/2011 |
| WO | 2011/113882 A1 | 9/2011 |

OTHER PUBLICATIONS

A_GENESEQ ADE36714 (2004).*
A_GENESEQ AAO18896.*
Hida et al (Canc. Immunol. Immunother. 2002, 51(4): 219-228).*
Dziubianau et al (Amer. J. Transpl., 2013, 13: 28423-2854) (Year: 2013).*
Denkberg et al (J. Immunol. 2002, 169: 4399-4407) (Year: 2002).*
DiBrino et al (J. Immunology 151(11) 5390-5935, 1993) (Year: 1993).*
Celis et al (Molecular Immunol. 3: 1423-1430, 1994) (Year: 1994).*
Ochoa-Garay et al (Mol. Immunol., 1997, 34(3): 273-281)ochoa (Year: 1997).*
"Immatics Raises Euro 54 Million to Advance Its Late Stage Clinical Therapeutic Cancer Vaccine Portfolio", 02, Sep. 21, 2010 (Sep. 21, 2010), XP002634488, Retrieved from the Internet: <URL:http://www.immatics.com/page=57&modaction=detail&modid=249> [retrieved on Apr. 28, 2011].

(Continued)

*Primary Examiner* — Michael Szperka
*Assistant Examiner* — Marianne Dibrino
(74) *Attorney, Agent, or Firm* — McBee Moore Woodward & Vanik IP, LLC; Susan McBee

(57) ABSTRACT

The present invention relates to immunotherapeutic peptides and their use in immunotherapy, in particular the immunotherapy of cancer. The present invention discloses tumor-associated T-helper cell peptide epitopes, alone or in combination with other tumor-associated peptides that serve as active pharmaceutical ingredients of vaccine compositions which stimulate anti-tumor immune responses. In particular, the composition of the peptides of the present invention can be used in vaccine compositions for eliciting anti-tumor immune responses against gastric cancers (GC).

4 Claims, 5 Drawing Sheets
Specification includes a Sequence Listing.

(56) References Cited

OTHER PUBLICATIONS

Singh-Jasuja et al.; Immatics: "IMA901—" A novel multi-peptide vaccine for treatment of renal cell carcinoma, J. Immunother; ISBTC Nov./Dec. 2007, vol. 30; No. 8; p. 902; Boston MA, 2007, XP002634490, Abstract.
"Immatics Company Fact Sheet", V, Feb. 1, 2009 (Feb. 1, 2009), XP002634491.
Singh-Jasuja H et al: "IMA901, a novel multi-peptide vaccine for the treatment of renal cell carcinoma—pre-clinical and clinical studies and implications for combination with other agents", Journal of Immunotherapy, Lippincott Williams & Wilkins, Hagerstown, MD, US, vol. 30, No. 8, Nov. 4, 2007 (Nov. 4, 2007), p. 902, XP008098593, ISSN: 1524-9557.
Toni Weinschenk: "Multi-peptide-based Vaccines for Peronalized Cancer Therapy", 2004, XP002634492, Retrieved fro m the Internet: URL:http://tobias-lib.uni-tuebingen.de/volitexte/2004/10951 pdf; Dissertation_Toni_Weinschenk.pdf.
Singh Harpreet: "Development of novel vaccines against prostate hyperplasia and gastric cancer—Report of the BioProfile projects PROstat and GCa", Tissue Engineering, vol. 13, No. 4, Apr. 2007 (Apr. 2007), p. 888, XP009247697, & 2nd International Congress on Regenerative Biology/2nd International Congress on Bio-Nano-Interface; Stuttgart, Germany; Oct. 9-11, 2006; ISSN: 1076-3279.
European Search Report dated Oct. 10, 2013, issued in Application No. 11 708 860.9-1456.
Great Britain Search Report dated Jun. 10, 2010.

\* cited by examiner

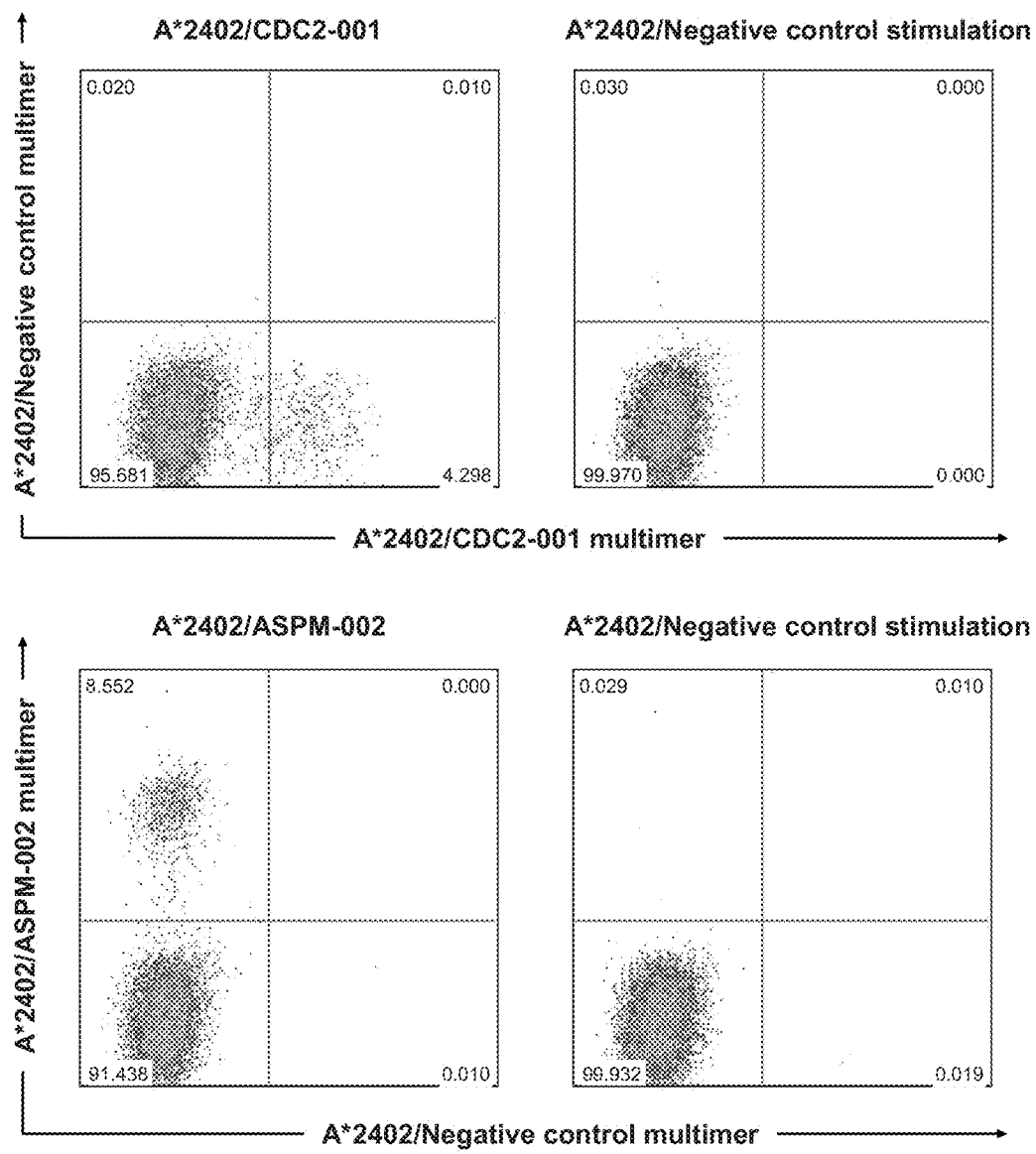
Figure 1: Exemplary *in vitro* immunogenicity of IMA941 class I TUMAPs

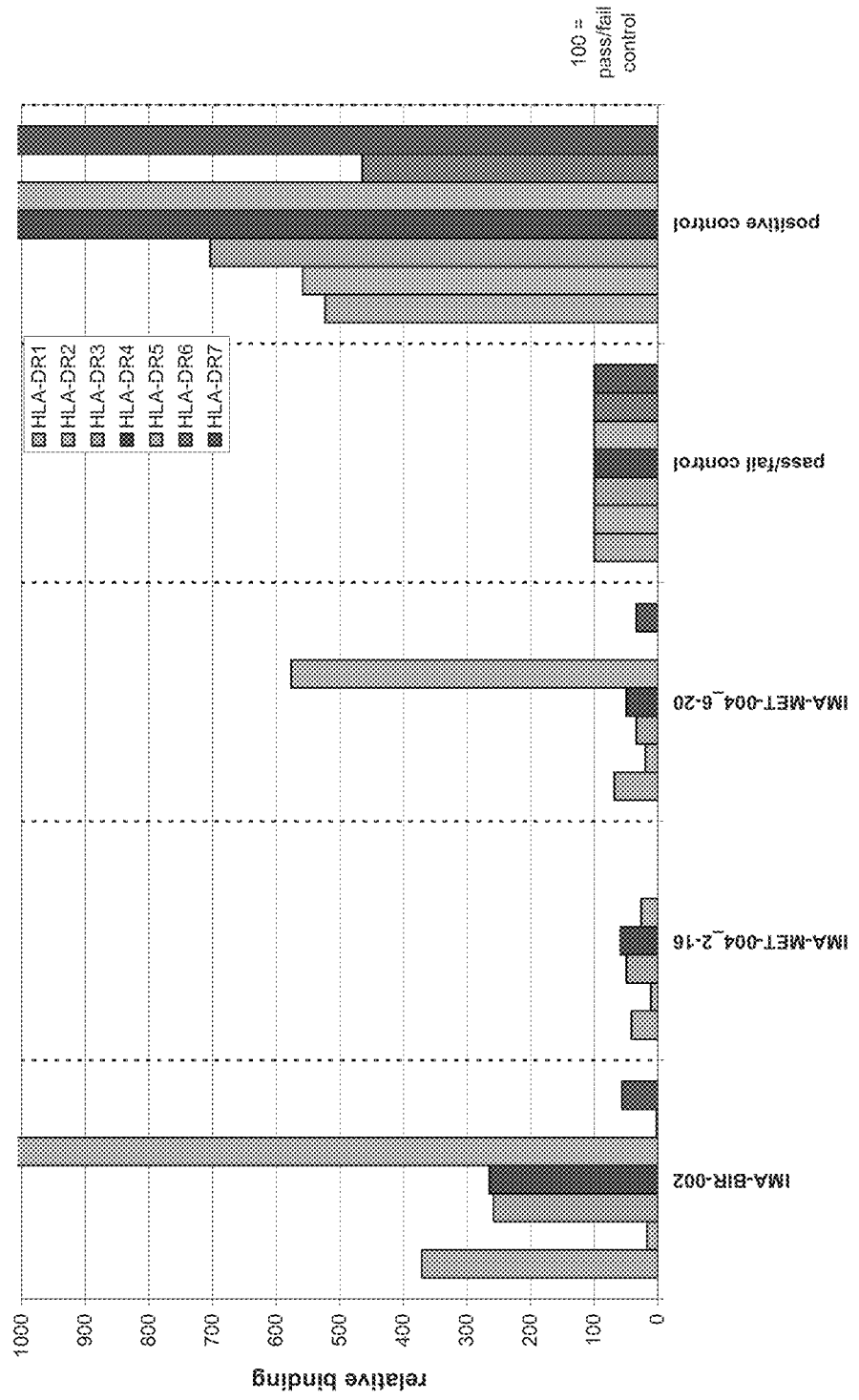

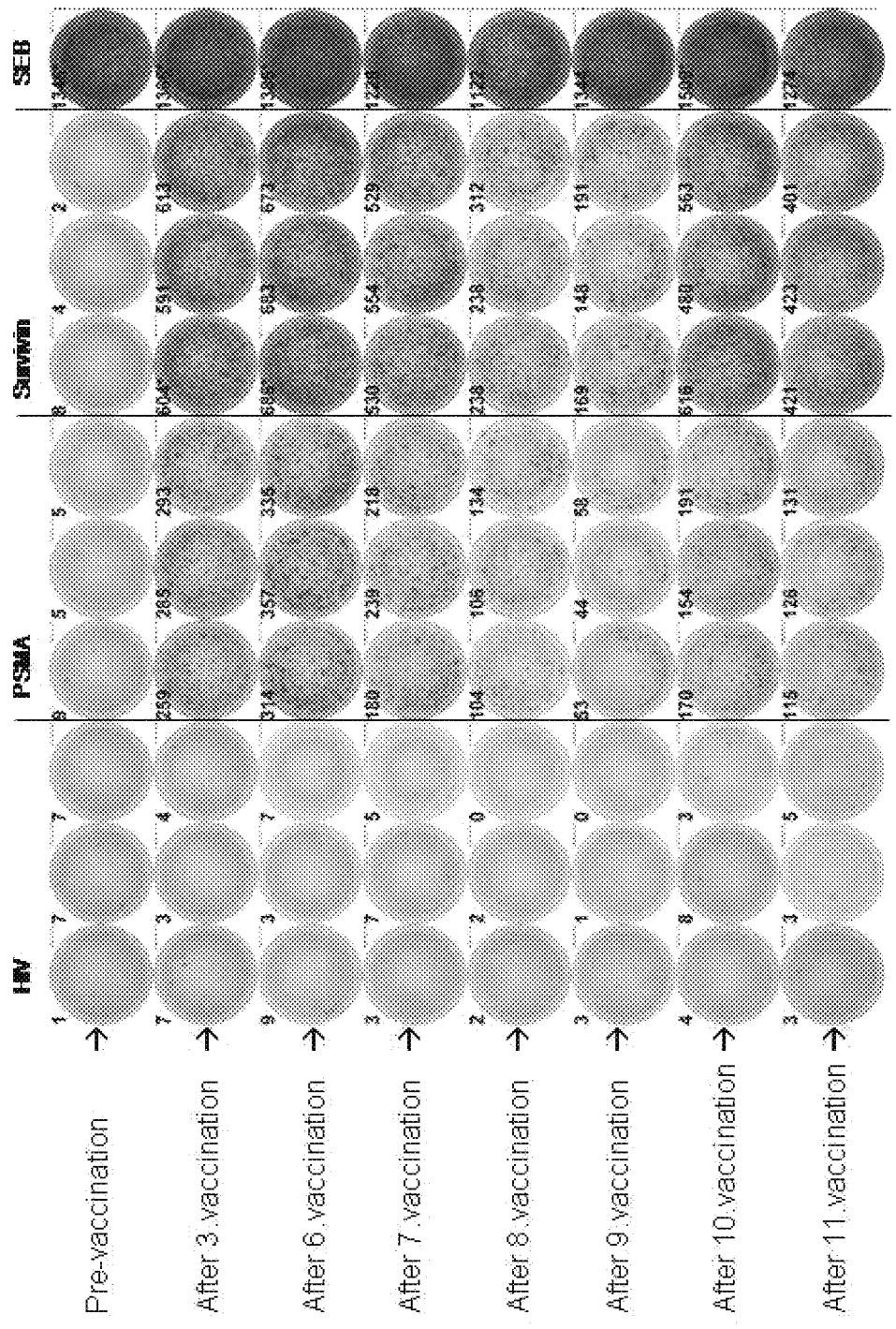
Figure 3a: gamma interferon-ELISpot

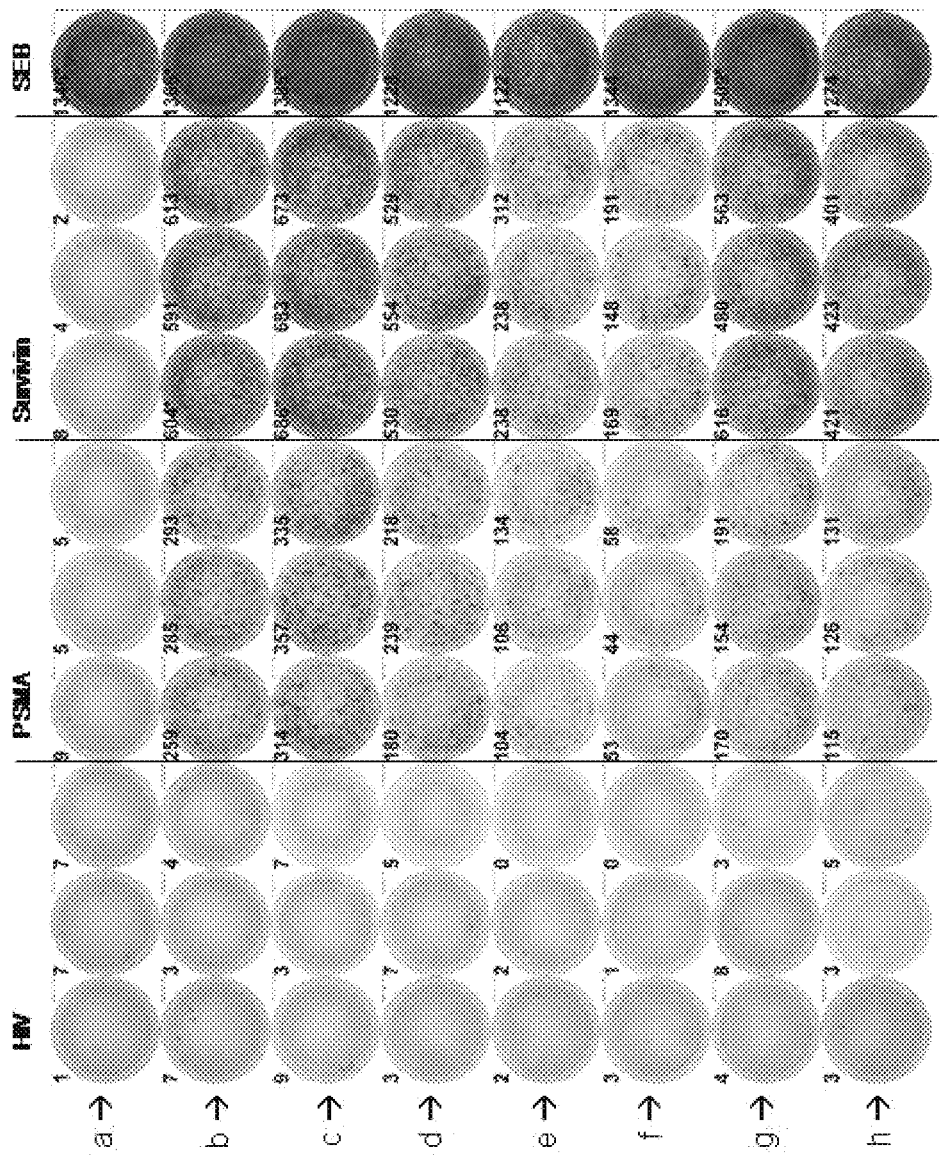

SEQUENCE LISTING

<160> NUMBER OF SEQ ID NOS: 24

<210> SEQ ID NO 1
<211> LENGTH: 10
<212> TYPE: PRT
<213> ORGANISM: Homo sapiens

<400> SEQUENCE: 1

Leu Tyr Gln Ile Leu Gln Gly Ile Val Phe
1               5                   10

<210> SEQ ID NO 2

```
<211> LENGTH: 9
<212> TYPE: PRT
<213> ORGANISM: Homo sapiens

<400> SEQUENCE: 2

Ser Tyr Asn Pro Leu Trp Leu Arg Ile
1               5

<210> SEQ ID NO 3
<211> LENGTH: 9
<212> TYPE: PRT
<213> ORGANISM: Homo sapiens

<400> SEQUENCE: 3

Asn Tyr Leu Pro Phe Ile Met Glu Leu
1               5

<210> SEQ ID NO 4
<211> LENGTH: 9
<212> TYPE: PRT
<213> ORGANISM: Homo sapiens

<400> SEQUENCE: 4

Ser Tyr Ile Asp Val Leu Pro Glu Phe
1               5

<210> SEQ ID NO 5
<211> LENGTH: 9
<212> TYPE: PRT
<213> ORGANISM: Homo sapiens

<400> SEQUENCE: 5

Ser Tyr Ile Ile Asp Pro Leu Asn Leu
1               5

<210> SEQ ID NO 6
<211> LENGTH: 10
<212> TYPE: PRT
<213> ORGANISM: Homo sapiens

<400> SEQUENCE: 6

Tyr Tyr Asn Ala Ala Gly Phe Asn Lys Leu
1               5                   10

<210> SEQ ID NO 7
<211> LENGTH: 9
<212> TYPE: PRT
<213> ORGANISM: Homo sapiens

<400> SEQUENCE: 7

Asn Tyr Leu Leu Tyr Val Ser Asn Phe
1               5

<210> SEQ ID NO 8
<211> LENGTH: 9
<212> TYPE: PRT
<213> ORGANISM: Homo sapiens

<400> SEQUENCE: 8

Ala Tyr Leu Val Tyr Thr Asp Arg Leu
1               5

<210> SEQ ID NO 9
<211> LENGTH: 9
<212> TYPE: PRT
```

```
<213> ORGANISM: Homo sapiens

<400> SEQUENCE: 9

His Tyr Lys Pro Thr Pro Leu Tyr Phe
1               5

<210> SEQ ID NO 10
<211> LENGTH: 10
<212> TYPE: PRT
<213> ORGANISM: Homo sapiens

<400> SEQUENCE: 10

Val Trp Ser Asp Val Thr Pro Leu Thr Phe
1               5                   10

<210> SEQ ID NO 11
<211> LENGTH: 15
<212> TYPE: PRT
<213> ORGANISM: Homo sapiens

<400> SEQUENCE: 11

Thr Leu Gly Glu Phe Leu Lys Leu Asp Arg Glu Arg Ala Lys Asn
1               5                   10                  15

<210> SEQ ID NO 12
<211> LENGTH: 16
<212> TYPE: PRT
<213> ORGANISM: Homo sapiens

<400> SEQUENCE: 12

Asp Asp Pro Ser Thr Ile Glu Lys Leu Ala Lys Asn Lys Gln Lys Pro
1               5                   10                  15

<210> SEQ ID NO 13
<211> LENGTH: 17
<212> TYPE: PRT
<213> ORGANISM: Homo sapiens

<400> SEQUENCE: 13

Asn Lys Gln Lys Pro Ile Thr Pro Glu Thr Ala Glu Lys Leu Ala Arg
1               5                   10                  15

Asp

<210> SEQ ID NO 14
<211> LENGTH: 17
<212> TYPE: PRT
<213> ORGANISM: Homo sapiens

<400> SEQUENCE: 14

Asn Gly Ala Tyr Lys Ala Ile Pro Val Ala Gln Asp Leu Asn Ala Pro
1               5                   10                  15

Ser

<210> SEQ ID NO 15
<211> LENGTH: 15
<212> TYPE: PRT
<213> ORGANISM: Homo sapiens

<400> SEQUENCE: 15

Thr Leu Gly Glu Phe Leu Lys Leu Asp Arg Glu Arg Ala Lys Asp
1               5                   10                  15

<210> SEQ ID NO 16
```

```
<211> LENGTH: 9
<212> TYPE: PRT
<213> ORGANISM: Homo sapiens

<400> SEQUENCE: 16

Phe Thr Glu Leu Thr Leu Gly Glu Phe
1               5

<210> SEQ ID NO 17
<211> LENGTH: 9
<212> TYPE: PRT
<213> ORGANISM: Homo sapiens

<400> SEQUENCE: 17

Leu Met Leu Gly Glu Phe Leu Lys Leu
1               5

<210> SEQ ID NO 18
<211> LENGTH: 9
<212> TYPE: PRT
<213> ORGANISM: Homo sapiens

<400> SEQUENCE: 18

Glu Pro Asp Leu Ala Gln Cys Phe Tyr
1               5

<210> SEQ ID NO 19
<211> LENGTH: 9
<212> TYPE: PRT
<213> ORGANISM: Homo sapiens

<400> SEQUENCE: 19

Val Tyr Gly Ile Arg Leu Glu His Phe
1               5

<210> SEQ ID NO 20
<211> LENGTH: 9
<212> TYPE: PRT
<213> ORGANISM: Homo sapiens

<400> SEQUENCE: 20

Phe Tyr Ile Ser Pro Val Asn Lys Leu
1               5

<210> SEQ ID NO 21
<211> LENGTH: 9
<212> TYPE: PRT
<213> ORGANISM: Homo sapiens

<400> SEQUENCE: 21

Thr Tyr Gly Asn Leu Leu Asp Tyr Leu
1               5

<210> SEQ ID NO 22
<211> LENGTH: 9
<212> TYPE: PRT
<213> ORGANISM: Homo sapiens

<400> SEQUENCE: 22

Arg Phe Leu Ser Gly Ile Ile Asn Phe
1               5

<210> SEQ ID NO 23
<211> LENGTH: 10
<212> TYPE: PRT
```

```
<213> ORGANISM: Homo sapiens

<400> SEQUENCE: 23

Phe Leu Pro Ser Asp Phe Phe Pro Ser Val
1               5                   10

<210> SEQ ID NO 24
<211> LENGTH: 9
<212> TYPE: PRT
<213> ORGANISM: Homo sapiens

<400> SEQUENCE: 24

Val Tyr Ile Glu Lys Asn Asp Lys Leu
1               5
```

COMPOSITION OF TUMOR-ASSOCIATED PEPTIDES AND RELATED ANTI-CANCER VACCINE FOR THE TREATMENT OF GASTRIC CANCER AND OTHER CANCERS

CROSS REFERENCE TO RELATED APPLICATIONS

This application is a § 371 National Stage Application of PCT/EP2011/053996, filed Mar. 16, 2011, which claims priority to United Kingdom Application No. 1004575.5, filed Mar. 19, 2010, and U.S. Provisional Application No. 61/315,715, filed Mar. 19, 2010.

BACKGROUND OF THE INVENTION

Field of the Invention

The present invention relates to immunotherapeutic peptides and their use in immunotherapy, in particular the immunotherapy of cancer. The present invention discloses tumor-associated T-helper cell peptide epitopes, alone or in combination with other tumor-associated peptides that serve as active pharmaceutical ingredients of vaccine compositions which stimulate anti-tumor immune responses. In particular, the composition of the peptides of the present invention can be used in vaccine compositions for eliciting anti-tumor immune responses against gastric and other cancers (GC).

For the purposes of the present invention, all references as cited herein are incorporated by reference in their entireties.

Description of Related Art

Gastric cancer is a disease in which malignant cells form in the lining of the stomach. Stomach or gastric cancer can develop in any part of the stomach and may spread throughout the stomach and to other organs; particularly the esophagus, lungs and the liver. Stomach cancer is the fourth most common cancer worldwide with 930,000 cases diagnosed in 2002. It is a disease with a high death rate (~800,000 per year) making it the second most common cause of cancer death worldwide after lung cancer. It is more common in men and occurs more often in Asian countries and in developing countries. (Informations can be obtained from the WHO.)

It represents roughly 2% (25,500 cases) of all new cancer cases yearly in the United States, but it is more common in other countries. It is the leading cancer type in Korea, with 20.8% of malignant neoplasms. In Japan gastric cancer remains the most common cancer for men. Each year in the United States, about 13,000 men and 8,000 women are diagnosed with stomach cancer. Most are over 70 years old.

Stomach cancer is the fourth most common cancer worldwide, after cancers of the lung, breast, and colon and rectum. Furthermore, stomach cancer remains the second most common cause of death from cancer. The American Cancer Society estimates that in 2007 there were an estimated one million new cases, nearly 70% of them in developing countries, and about 800,000 deaths (see the publications of the American Cancer Society).

Tremendous geographic variation exists in the incidence of this disease around the world. Rates of the disease are highest in Asia and parts of South America and lowest in North America. The highest death rates are recorded in Chile, Japan, South America, and the former Soviet Union.

Gastric cancer is often diagnosed at an advanced stage, because screening is not performed in most of the world, except in Japan (and in a limited fashion in Korea) where early detection is often done. Thus, it continues to pose a major challenge for healthcare professionals. Risk factors for gastric cancer are *Helicobacter pylori* (*H. pylori*) infection, smoking, high salt intake, and other dietary factors. A few gastric cancers (1% to 3%) are associated with inherited gastric cancer predisposition syndromes. E-cadherin mutations occur in approximately 25% of families with an autosomal dominant predisposition to diffuse type gastric cancers. This subset of gastric cancer has been termed hereditary diffuse gastric cancer. 12 It may be useful to provide genetic counseling and to consider prophylactic gastrectomy in young, asymptomatic carriers of germ-line truncating The wall of the stomach is made up of 3 layers of tissue: the mucosal (innermost) layer, the muscularis (middle) layer, and the serosal (outermost) layer. Gastric cancer begins in the cells lining the mucosal layer and spreads through the outer layers as it grows. Four types of standard treatment are used. Treatment for gastric cancer may involve Surgery, Chemotherapy, Radiation therapy or Chemoradiation. Surgery is the primary treatment for gastric cancer. The goal of surgery is to accomplish a complete resection with negative margins (R0 resection). However, approximately 50% of patients with locoregional gastric cancer cannot undergo an R0 resection. R1 indicates microscopic residual cancer (positive margins); and R2 indicates gross (macroscopic) residual cancer but not distant disease. Patient outcome depends on the initial stage of the cancer at diagnosis. (NCCN Clinical Practice Guidelines in Oncology™)

The 5-year survival rate for curative surgical resection ranges from 30-50% for patients with stage II disease and from 10-25% for patients with stage III disease. These patients have a high likelihood of local and systemic relapse. Metastasis occurs in 80-90% of individuals with stomach cancer, with a six month survival rate of 65% in those diagnosed in early stages and less than 15% of those diagnosed in late stages.

There thus remains a need for new efficacious and safe treatment option for gastric cancer, prostate carcinoma, oral cavity carcinomas, oral squamous carcinoma (OSCC), acute myeloid leukemia (AML) (Qian et al., 2009), *H. pylori*-induced MALT lymphoma (Banerjee et al., 2000), colon carcinoma/colorectal cancer, glioblastoma, non-small-cell lung cancer (NSCLC), cervical carcinoma, human breast cancer, prostate cancer, colon cancer, pancreatic cancers, pancreatic ductal adenocarcinoma, ovarian cancer, hepatocellular carcinoma, liver cancer, brain tumors of different phenotypes, leukemias such as acute lymphoblastic leukemia (ALL), lung cancer, Ewing's sarcoma, endometrial cancer, head and neck squamous cell carcinoma, epithelial cancer of the larynx, oesophageal carcinoma, oral carcinoma, carcinoma of the urinary bladder, ovarian carcinomas, renal cell carcinoma, atypical meningioma, papillary thyroid carcinoma, brain tumors, salivary duct carcinoma, cervical cancer, extranodal T/NK-cell lymphomas, Non-Hodgkins Lymphoma and malignant solid tumors of the lung and breast and other tumors. There also remains a need for treatment options that enhance the well-being of the patients without using chemotherapeutic agents or other agents which may lead to severe side effects.

Colorectal Carcinoma

According to the American Cancer Society, colorectal cancer (CRC) is the third most common cancer in the US, afflicting more than 175,000 new patients each year. In the US, Japan, France, Germany, Italy Spain and the UK, it affects more than 480,000 patients. It is one of the most common causes of cancer mortality in developed countries. Research suggests that the onset of colorectal cancer is the result of interactions between inherited and environmental factors. In most cases adenomatous polyps appear to be precursors to colorectal tumors; however the transition may take many years. The primary risk factor for colorectal cancer is age, with 90% of cases diagnosed over the age of 50 years. Other risk factors for colorectal cancer according to the American Cancer Society include alcohol consumption, a diet high in fat and/or red meat and an inadequate intake of fruits and vegetables. Incidence continues to rise, especially in areas such as Japan, where the adoption of westernized diets with excess fat and meat intake and a decrease in fiber intake may be to blame. However, incidence rates are rising not as fast as previously which may be due to increasing screening and polyp removal, thus preventing progression of polyps to cancer.

As in most solid tumors, first line treatment is surgery, however, its benefits remain confined to early-stage patients, yet a significant proportion of patients is diagnosed in advanced stages of the disease. For advanced colorectal cancer chemotherapy regimens based on fluorouracil-based regimens are standard of care. The majority of these regimens are the so-called FOLFOX (infusional 5-FU/leucovorin plus oxaliplatin) and FOLFIRI (irinotecan, leucovorin, bolus and continuous-infusion 5-FU) protocols.

The introduction of third-generation cytotoxics such as irinotecan and oxaliplatin has raised the hope of significantly improving efficacy, but prognosis is still relatively poor, and the survival rate generally remains at approximately 20 months in metastatic disease and, as a result, the unmet needs in the disease remain high.

Recently, a novel generation of drugs, molecular-targeted agents, such as Avastin (bevacizumab) and Erbitux (cetuximab), became available, and about 40 compounds are in late-stage clinical development for different stages of colorectal cancer. Combinations of several of these compounds increase the number of potential treatment options to be expected for the future. The vast majority of substances is in phase 2, with EGFR addressed by these compounds more often than by any other drug in development for colorectal cancer, which is due to the fact that in ~80% of patients with colorectal cancer EGFR expression is upregulated.

Clinical trials with stage II patients combining chemotherapy with the recently approved monoclonal antibodies (mAbs) (cetuximab+irinotecan or FOLFOX4; bevacizumab as a single-agent or together with FOLFOX4) are currently conducted. Three to four year observation periods are expected for statistically significant results from these trials.

Monoclonal antibodies (mAbs) presently used in oncology in general have an excellent chance of not interfering with active immunotherapy. In fact, there is preclinical evidence suggesting that depletion of VEGF (by bevacizumab) contributes positively to DC-mediated activation of T-cells.

Prostate Carcinoma and Other Exemplary Tumors

With an estimated 27,050 deaths in 2007, prostate cancer is a leading cause of cancer death in men. Although death rates have been declining among white and African American men since the early 1990s, rates in African American men remain more than twice as high as those in white men. Prostate cancer is the most frequently diagnosed cancer in men. For reasons that remain unclear, incidence rates are significantly higher in African American men than in white men. Incidence rates of prostate cancer have changed substantially over the last 20 years: rapidly increasing from 1988-1992, declining sharply from 1992-1995, and increasing modestly since 1995. These trends in large part reflect increased prostate cancer screening with the prostate-specific antigen (PSA) blood test. Moderate incidence increases in the last decade are most likely attributable to widespread PSA screening among men younger than 65. Prostate cancer incidence rates have leveled off in men aged 65 years and older. Rates peaked in white men in 1992 (237.6 per 100,000 men) and in African American men in 1993 (342.8 per 100,000 men).

Treatment for prostate cancer may involve watchful waiting, surgery, radiation therapy, High Intensity Focused Ultrasound (HIFU), chemotherapy, cryosurgery, hormonal therapy, or some combination of the above. The best option depends on the stage of the disease, the Gleason score, and the PSA level. Other important factors include the man's age, his general health, and his feelings about potential treatments and their possible side effects. Because all treatments can have significant side effects, such as erectile dysfunction and urinary incontinence, treatment discussions often focus on balancing the goals of therapy with the risks of lifestyle alterations.

If the cancer has spread beyond the prostate, treatment options significantly change, so most doctors who treat prostate cancer use a variety of tomograms to predict the probability of spread. Treatment by watchful waiting, HIFU, radiation therapy, cryosurgery, and surgery are generally offered to men whose cancer remains within the prostate. Hormonal therapy and chemotherapy are often reserved for disease which has spread beyond the prostate. However, there are exceptions: radiation therapy may be used for some advanced tumors, and hormonal therapy is used for some early stage tumors. Cryotherapy, hormonal therapy, and chemotherapy may also be offered if initial treatment fails and the cancer progresses.

In a significant number of patients with prostate carcinoma who undergo radical prostatectomy because of clinically suspected organ-limited growth, a definitive histological workup of the surgical preparation shows a locally extensive tumor extending beyond the borders of the organ. These patients have a high risk for early local recurrence, usually detectable as an increasing PSA level in terms of a biochemical relapse. Therapeutic options in this situation include external radiotherapy and hormone ablation; however, the value of these therapeutic approaches, especially with respect to prolonging the patient's long-term survival, must not be regarded as proven. In addition, possible treatment-associated complications such as the development of urethral strictures (radiotherapy), loss of libido and impotence, the risk of a reduction in skeletal calcium salts in terms of osteoporosis, and a markedly increased risk of pathologic bone fractures (hormone ablation) must be considered.

More than 90% of all prostate cancers are discovered in the local and regional stages; the 5-year relative survival rate for patients whose tumors are diagnosed at these stages approaches 100%. Over the past 25 years, the 5-year survival rate for all stages combined has increased from 69% to nearly 90%. According to the most recent data, relative 10-year survival is 93% and 15-year survival is 77%. The dramatic improvements in survival, particularly at 5 years, are partly attributable to earlier diagnosis and improvements in treatment. Nevertheless, the survival rate drops significantly after the spreading to other tissues and organs.

Lung Cancer

An estimated 210,000 new cases are expected in 2007 in the USA, accounting for about 15% of cancer diagnoses. The incidence rate is declining significantly in men, from a high of 102 cases per 100,000 in 1984 to 78.5 in 2003. In women, the rate is approaching a plateau after a long period of increase. Lung cancer is classified clinically as small cell (13%) or non-small cell (87%) for the purposes of treatment.

Lung cancer accounts for the most cancer-related deaths in both men and women. An estimated 160,390 deaths, accounting for about 29% of all cancer deaths, are expected to occur in 2007. Since 1987, more women have died each year from lung cancer than from breast cancer. Death rates have continued to decline significantly in men from 1991-2003 by about 1.9% per year. Female lung cancer death rates are approaching a plateau after continuously increasing for several decades. These trends in lung cancer mortality reflect the decrease in smoking rates over the past 30 years.

Treatment options are determined by the type (small cell or non-small cell) and stage of cancer and include surgery, radiation therapy, chemotherapy, and targeted biological therapies such as bevacizumab (Avastin®) and erlotinib (Tarceva®). For localized cancers, surgery is usually the treatment of choice. Recent studies indicate that survival with early-stage, non-small cell lung cancer is improved by chemotherapy following surgery. Because the disease has usually spread by the time it is discovered, radiation therapy and chemotherapy are often used, sometimes in combination with surgery. Chemotherapy alone or combined with radiation is the usual treatment of choice for small cell lung cancer; on this regimen, a large percentage of patients experience remission, which is long lasting in some cases.

The 1-year relative survival for lung cancer has slightly increased from 37% in 1975-1979 to 42% in 2002, largely due to improvements in surgical techniques and combined therapies. However, the 5-year survival rate for all stages combined is only 16%. The survival rate is 49% for cases detected when the disease is still localized: however, only 16% of lung cancers are diagnosed at this early stage.

SUMMARY

There thus remains a need for new efficacious and safe treatment option for glioblastoma, prostate tumor, breast cancer, esophageal cancer, colorectal cancer, clear cell renal cell carcinoma, lung cancer, CNS, ovarian, melanoma, pancreatic cancer, squamous cell carcinoma, leukemia and medulloblastoma and other tumors which show an overexpression of survivin, enhancing the well-being of the patients without using chemotherapeutic agents or other agents which may lead to severe side effects.

BRIEF DESCRIPTION OF THE DRAWINGS

FIGS. 1-4 depict embodiments of the present invention as described herein.

DETAILED DESCRIPTION OF A PREFERRED EMBODIMENT

Figure 4:
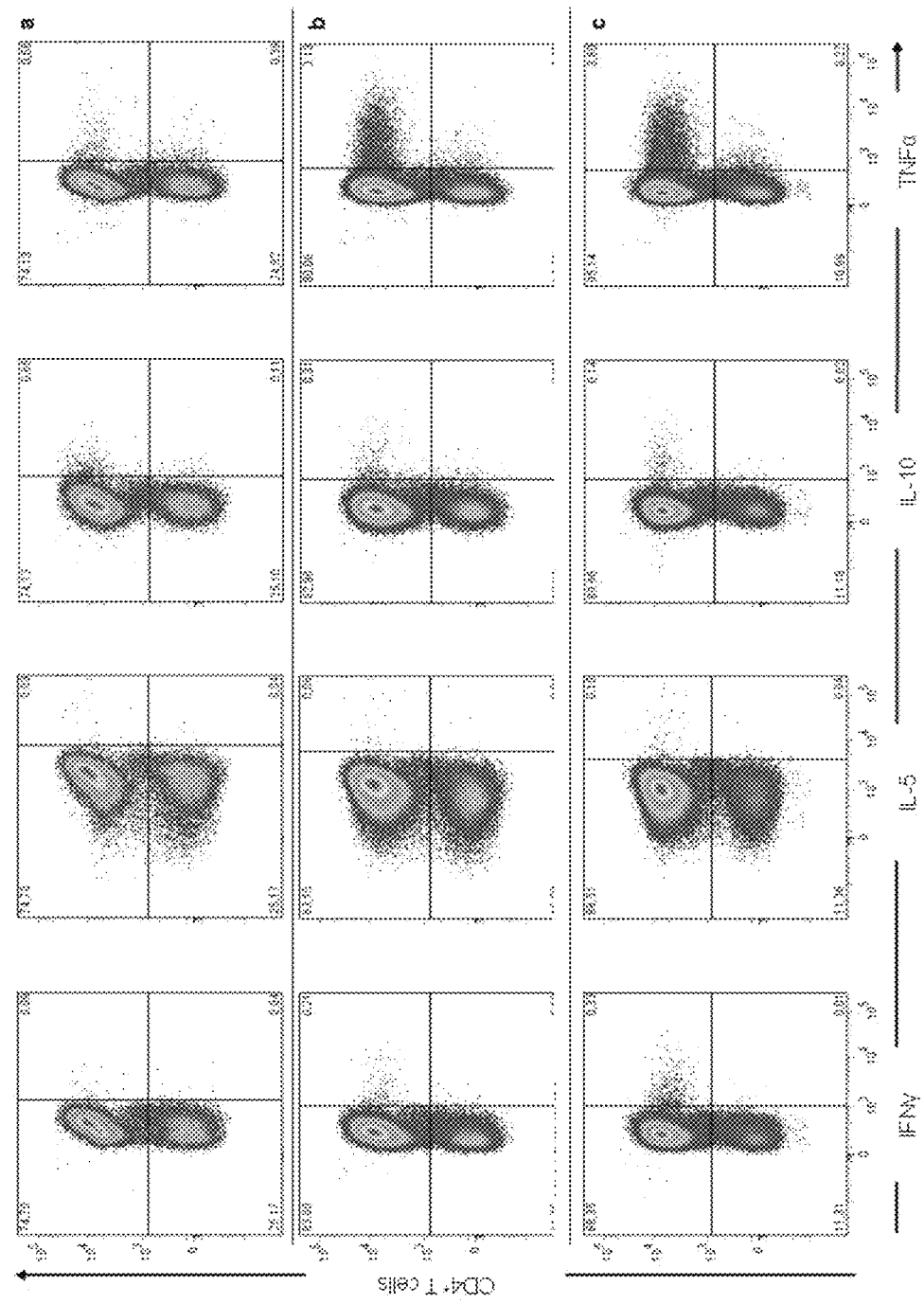

As used herein and except as noted otherwise all terms are defined as given below. The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, 12, 13, 14, 15, 16, 17 or 18 amino acids in length.

The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 14 amino acids in length.

TABLE 1

Estimated new cancer cases and deaths by sex for the US in 2007 (American Cancer Society. Cancer Facts & Figures 2007. Atlanta: American Cancer Society; 2007.)

| | Estimated New Cases | | | Estimated Deaths | | |
| --- | --- | --- | --- | --- | --- | --- |
| Sites | Both Sexes | Male | Female | Both Sexes | Male | Female |
| Glioma and Brain | 20,500 | 11,170 | 9,330 | 12,740 | 7,150 | 5,590 |
| Breast | 180,510 | 2,030 | 178,480 | 40,910 | 450 | 40,460 |
| Prostate | 218,890 | 218,890 | | 27,050 | 27,050 | |
| Esophagus | 15,560 | 12,130 | 3,430 | 13,940 | 10,900 | 3,040 |
| Colon | 112,340 | 55,290 | 57,050 | 52,180 | 26,000 | 26,180 |
| Renal | 51,190 | 31,590 | 19,600 | 12,890 | 8,080 | 4,810 |
| Pancreas | 37,170 | 18,830 | 18,340 | 33,370 | 16,840 | 16,530 |
| Squamous cell carcinomas; Keratinocytic neoplasms of the skin | 1,000,000 | n.d. | n.d. | n.d. | n.d. | n.d. |
| Leukemia | 44,240 | 24,800 | 19,440 | 21,790 | 12,320 | 9,470 |
| Lung | 213,380 | 114,760 | 98,620 | 160,390 | 89,510 | 70,880 |
| Non-Hodgkins Lymphoma | 63,190 | 34,210 | 28,990 | 18,660 | 9,600 | 9,060 |
| Ovarian | 22,430 | | 22,430 | 15,280 | | 15,280 |
| Melanoma | 59,940 | 33,910 | 26,030 | 8,110 | 5,220 | 2,890 |

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response.

A T cell "epitope" requires a short peptide that is bound to a class I or II MHC receptor, forming a ternary complex (MHC class I alpha chain, beta-2-microglobulin, and peptide) that can be recognized by a T cell bearing a matching T-cell receptor binding to the MHC/peptide complex with appropriate affinity. Peptides binding to MHC class I molecules are typically 8-14 amino acids in length, and most typically 9 amino acids in length. T cell epitopes that bind to MHC class II molecules are typically 12-30 amino acids in length. In the case of peptides that bind to MHC class II molecules, the same peptide and the corresponding T cell epitope may share a common core segment, but differ in the overall length due to flanking sequences of differing lengths upstream of the amino-terminus of the core sequence and downstream of its carboxy-terminus, respectively. MHC class II receptors have a more open conformation, peptides bound to MHC class II receptors are correspondingly not completely buried in the structure of the MHC class II molecule peptide-binding cleft as they are in the MHC class I molecule peptide-binding cleft. Surprisingly this is not the case for the peptide according to SEQ ID NO: 1 as small variations in the length of the peptide lead to an extreme decrease of activity (see below).

In humans there, are three different genetic loci that encode MHC class I molecules (the MHC-molecules of the human are also designated human leukocyte antigens (HLA)): HLA-A, HLA-B, and HLA-C, HLA-A*01, HLA-A*02, and HLA-A*11 are examples of different MHC class I alleles that can be expressed from these loci.

There are three different loci in the human genome for MHC class II genes: HLA-DR, HLA-DQ, and HLA-DP. MHC class II receptors are heterodimers consisting of an alpha and a beta chain, both anchoring in the cell membrane via a transmembrane region. HLA-DRB1*04, and HLA-DRB1*07 are two examples of different MHC class II beta alleles that are known to be encoded in these loci. Class II alleles are very polymorphic, e.g. several hundred different HLA-DRB1 alleles have been described. For HLA-A*02 and most frequent HLA-DR serotypes, expression frequencies in different populations are shown in Table 2.

Table 2: Provides expression frequencies F of HLA*A02 and the most frequent HLA-DR serotypes. Frequencies are deduced from haplotype frequencies $G_f$ within the American population adapted from Mori et al. (Mori et al., 1997) employing the Hardy-Weinberg formula $F=1-(1-G_f)^2$. Combinations of A*02 with certain HLA-DR alleles might be enriched or less frequent than expected from their single frequencies due to linkage disequilibrium. For details refer to Chanock et al. (Chanock et al., 2004).

| | Expression frequencies of HLA*02 and HLA-DR serotypes within North American subpopulations | | | |
|---|---|---|---|---|
| HLA Allele | Caucasian American | African American | Asian American | Latin American |
| A*02 | 49.1% | 34.1% | 43.2% | 48.3% |
| DR1 | 19.4% | 13.2% | 6.8% | 15.3% |
| DR2 | 28.2% | 29.8% | 33.8% | 21.2% |
| DR3 | 20.6% | 24.8% | 9.2% | 15.2% |
| DR4 | 30.7% | 11.1% | 28.6% | 36.8% |
| DR5 | 23.3% | 31.1% | 30.0% | 20.0% |
| DR6 | 26.7% | 33.7% | 25.1% | 31.1% |
| DR7 | 24.8% | 19.2% | 13.4% | 20.2% |
| DR8 | 5.7% | 12.1% | 12.7% | 18.6% |
| DR9 | 2.1% | 5.8% | 18.6% | 2.1% |

Table 3: provides expression frequencies F of HLA*A024 and the HLA*A02402 serotype. Frequencies are deduced from haplotype frequencies $G_f$ within the population adapted from Mori et al. (Mori et al., 1997) employing the Hardy-Weinberg formula $F=1-(1-Gf)^2$. For details refer to Chanock et al. (Chanock et al., 2004).

TABLE 3

| | Expression frequencies of HLA*02 and A*2402 serotypes worldwide | |
|---|---|---|
| Allele | Population | Calculated phenotype from Allele Frequency |
| A*24 | Philippines | 65% |
| A*24 | Russia Nenets | 61% |
| A*2402 | Japan | 59% |
| A*24 | Malaysi | 58% |
| A*2402 | Philippines | 54% |
| A*24 | India | 47% |
| A*24 | South Korea | 40% |
| A*24 | Sri Lanka | 37% |
| A*24 | China | 32% |
| A*2402 | India | 29% |
| A*24 | Australia West | 22% |
| A*24 | USA | 22% |
| A*24 | Russia Samara | 20% |
| A*24 | South Amerika | 20% |
| A*24 | Europa | 18% |

Therefore, for therapeutic and diagnostic purposes a peptide that binds with appropriate affinity to several different HLA class II receptors is highly desirable. A peptide binding to several different HL A class II molecules is called a promiscuous binder.

As used herein, reference to a DNA sequence includes both single stranded and double stranded DNA. Thus, the specific sequence, unless the context indicates otherwise, refers to the single strand DNA of such sequence, the duplex of such sequence with its complement (double stranded DNA) and the complement of such sequence. The term "coding region" refers to that portion of a gene which either naturally or normally codes for the expression product of that gene in its natural genomic environment, i.e., the region coding in vivo for the native expression product of the gene.

The coding region can be from a normal, mutated or altered gene, or can even be from a DNA sequence, or gene, wholly synthesized in the laboratory using methods well known to those of skill in the art of DNA synthesis.

The term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

The term "expression product" means the polypeptide or protein that is the natural translation product of the gene and any nucleic acid sequence coding equivalents resulting from genetic code degeneracy and thus coding for the same amino acid(s).

The term "fragment," when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal nontranslated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, the claimed polypeptide which has a purity of preferably 99.999%, or at least 99.99% or 99.9%; and even desirably 99% by weight or greater is expressly contemplated.

The nucleic acids and polypeptide expression products disclosed according to the present invention, as well as expression vectors containing such nucleic acids and/or such polypeptides, may be in "enriched form." As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form.

The term "active fragment" means a fragment that generates an immune response (i.e., has immunogenic activity) when administered, alone or optionally with a suitable adjuvant, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion," "segment," and "fragment," when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. This means that any such fragment will necessarily contain as part of its amino acid sequence a segment, fragment or portion, that is substantially identical, if not exactly identical, to a sequence of SEQ ID NO: 1 to 20, which correspond to the naturally occurring, or "parent" proteins of the SEQ ID NO: 1 to 20. When used in relation to polynucleotides, such terms refer to the products produced by treatment of said polynucleotides with any of the common endonucleases.

In accordance with the present invention, the term "percent identity" or "percent identical," when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula:

Percent Identity=$100[I-(C/R)]$ wherein C is the number of differences between the Reference Sequence and the Compared Sequence over the length of alignment between the Reference Sequence and the Compared Sequence, wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference;

and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the herein above calculated Percent Identity is less than the specified Percent Identity.

The original peptides disclosed herein can be modified by the substitution of one or more residues at different, possibly selective, sites within the peptide chain, if not otherwise stated.

Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often shown in correlation with similarities in size, charge, polarity, and hydrophobicity between the original amino acid and its replacement, and such is the basis for defining "conservative substitutions."

Conservative substitutions are herein defined as exchanges within one of the following five groups: Group 1—small aliphatic, nonpolar or slightly polar residues (Ala, Ser, Thr, Pro, Gly); Group 2—polar, negatively charged residues and their amides (Asp, Asn, Glu, Gln); Group 3—polar, positively charged residues (His, Arg, Lys); Group 4—large, aliphatic, nonpolar residues (Met, Leu, Ile, Val, Cys); and Group 5—large, aromatic residues (Phe, Tyr, Trp).

Less conservative substitutions might involve the replacement of one amino acid by another that has similar characteristics but is somewhat different in size, such as replacement of an alanine by an isoleucine residue. Highly nonconservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, amino acids possessing non-standard R groups (i.e., R groups other than those found in the common 20 amino acids of natural proteins) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would simultaneously be substituted.

The term "T-cell response" means the specific proliferation and activation of effector functions induced by a peptide in vitro or in vivo. For MHC class I restricted CTLs, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation. For MHC class II-restricted T helper cells, effector functions may be peptide induced secretion of cytokines, preferably, IFN-gamma, TNF-alpha, IL-4, IL5, IL-10, or IL-2, or peptide-induced degranulation. Possible effector functions for CTLs and T helper cells are not limited to this list.

Immunotherapeutic Approaches for Treatment

Stimulation of an immune response is dependent upon the presence of antigens recognized as foreign by the host immune system. The discovery of the existence of tumor associated antigens has now raised the possibility of using a host's immune system to intervene in tumor growth. Various mechanisms of harnessing both the humoral and cellular arms of the immune system are currently explored for cancer immunotherapy.

Specific elements of the cellular immune response are capable of specifically recognizing and destroying tumor cells. The isolation of cytotoxic T-cells (CTL) from tumor-infiltrating cell populations or from peripheral blood suggests that such cells play an important role in natural immune defenses against cancer. CD8-positive T-cells in particular, which recognize class I molecules of the major histocompatibility complex (MHC)-bearing peptides of usually 8 to 10 residues derived from proteins or defect ribosomal products (DRIPS) (Schubert U, Antón L C, Gibbs J, Norbury C C, Yewdell J W, Bennink J R.; Rapid degradation of a large fraction of newly synthesized proteins by proteasomes; Nature 2000; 404(6779):770-774) located in the cytosols, play an important role in this response. The MHC-molecules of the human are also designated as human leukocyte-antigens (HLA).

There are two classes of MHC-molecules: MHC class I molecules that can be found on most cells having a nucleus which present peptides that result from proteolytic cleavage of mainly endogenous, cytosolic or nuclear proteins, DRIPS, and larger peptides. However, peptides derived from endosomal compartments or exogenous sources are also frequently found on MHC class I molecules. This non-classical way of class I presentation is referred to as cross-presentation in literature. MHC class II molecules can be found predominantly on professional antigen presenting cells (APCs), and present predominantly peptides of exogenous proteins that are taken up by APCs during the course of endocytosis, and are subsequently processed. As for class I, alternative ways of antigen processing are described that allow peptides from endogenous sources to be presented by MHC class II molecules (e.g. autophagocytosis). Complexes of peptide and MHC class I molecule are recognized by CD8-positive cytotoxic T-lymphocytes bearing the appropriate TCR, whereas complexes of peptide and MHC class II molecule are recognized by CD4-positive helper T-cells bearing the appropriate TCR.

CD4-positive helper T-cells play an important role in orchestrating the effector functions of anti-tumor T-cell responses and for this reason the identification of CD4-positive T-cell epitopes derived from tumor associated antigens (TAA) may be of great importance for the development of pharmaceutical products for triggering anti-tumor immune responses (Gnjatic, S., D. Atanackovic, E. Jäger, M. Matsuo, A. Selvakumar, N. K. Altorki, R. G. Maki, B. Dupont, G. Ritter, Y. T. Chen, A. Knuth, and L. J. Old. Survey of naturally occurring CD4+ T-cell responses against NY-ESO-1 in cancer patients: Correlation with antibody responses. Proc. Natl. Acad. Sci. U.S.A. 2003, 100 (15): 8862-7) CD4+ T cells can lead to locally increased levels of IFN-gamma.

It was shown in mammalian animal models, e.g., mice, that even in the absence of CTL effector cells (i.e., CD8-positive T lymphocytes), CD4-positive T-cells are sufficient for inhibiting manifestation of tumors via inhibition of angiogenesis by secretion of interferon-gamma (IFNγ) (Qin, Z. and T. Blankenstein. CD4+ T-cell-mediated tumor rejection involves inhibition of angiogenesis that is dependent on IFN gamma receptor expression by nonhematopoietic cells. Immunity. 2000, 12:677-686). Additionally, it was shown that CD4-positive T-cells recognizing peptides from tumor-associated antigens presented by HLA class II molecules can counteract tumor progression via the induction of an antibody (Ab) responses (Kennedy, R. C., M. H. Shearer, A. M. Watts, and R. K. Bright. CD4+ T lymphocytes play a critical role in antibody production and tumor immunity against simian virus 40 large tumor antigen. Cancer Res. 2003, 63:1040-1045). In contrast to tumor-associated peptides binding to HLA class I molecules, only a small number of class II ligands of TAA have been described so far (www-.cancerimmunity.org, www.syfpeithi.de).

Since the constitutive expression of HLA class II molecules is usually limited to cells of the immune system the possibility of isolating class II peptides directly from primary tumors was not considered possible. However, the inventors were recently successful in identifying a number of MHC class II epitopes directly from tumors (EP 1642905, EP 1760088; Dengjel J, Nastke M D, Gouttefangeas C, Gitsioudis G, Schoor O, Altenberend F, Müller M, Krämer B, Missiou A, Sauter M, Hennenlotter J, Wernet D, Stenzl A, Rammensee H G, Klingel K, Stevanović S.; Unexpected abundance of HLA class II presented peptides in primary renal cell carcinomas; Clin Cancer Res. 2006; 12:4163-4170).

In the absence of inflammation, expression of MHC class II molecules is mainly restricted to cells of the immune system, especially APCs, e.g., monocytes, monocyte-derived cells, macrophages, dendritic cells. In tumor patients, cells of the tumor have surprisingly been found to express MHC class II molecules (Dengjel J, Nastke M D, Gouttefangeas C, Gitsioudis G, Schoor O, Altenberend F, Müller M, Krämer B, Missiou A, Sauter M, Hennenlotter J, Wernet D, Stenzl A, Rammensee H G, Klingel K, Stevanović S.; Unexpected abundance of HLA class II presented peptides in primary renal cell carcinomas; Clin Cancer Res. 2006; 12:4163-4170).

For a peptide to trigger (elicit) a cellular immune response, it must bind to an MHC-molecule. This process is dependent on the allele of the MHC-molecule and specific polymorphisms of the amino acid sequence of the peptide. MHC-class-1-binding peptides are usually 8-10 amino acid residues in length and usually contain two conserved residues ("anchor") in their sequence that interacts with the corresponding binding groove of the MHC-molecule. In this way each MHC allele has a "binding motif" determining which peptides can bind specifically to the binding groove (Rammensee H G, Bachmann J, Stevanovic S. MHC ligands and peptide motifs, Landes Bioscience, USA, 1997).

In MHC dependent immune reaction, peptides not only have to be able to bind to certain MHC molecules expressed by tumor cells, they also have to be recognized by T-cells bearing specific T-cell receptors (TCR).

The antigens that are recognized by the tumor specific T-lymphocytes, that is, their epitopes, can be molecules derived from all protein classes, such as enzymes, receptors, transcription factors, etc. Furthermore, tumor-associated antigens, for example, can also be present in tumor cells only, for example as products of mutated genes. Another important class of tumor-associated antigens are tissue-specific antigens, such as CT ("cancer testis")-antigens that are expressed in different kinds of tumors and in healthy tissue of the testis.

Various tumor-associated antigens have been identified. Further, much research effort is expended to identify additional tumor associated antigens. Some groups of tumor-associated antigens, also referred to in the art as tumor-specific antigens, are tissue specific. Examples include, but are not limited to, tyrosinase for melanoma, PSA and PSMA for prostate cancer and chromosomal cross-overs (translocations) such as bcr/abl in lymphoma. However, many tumor-associated antigens identified occur in multiple tumor types, and some, such as oncogenic proteins and/or tumor suppressor genes (tumor suppressor genes are, for example reviewed for renal cancer in Linehan W M, Walther M M, Zbar B. The genetic basis of cancer of the kidney. J Urol. 2003 December; 170 (6Pt1):2163-72) which actually cause the transformation event, occur in nearly all tumor types. For example, normal cellular proteins that control cell growth and differentiation, such as p53 (which is an example for a tumor suppressor gene), ras, c-met, myc, pRB, VHL, and HER-2/neu, can accumulate mutations resulting in upregulation of expression of these gene products thereby making them oncogenic {McCartey 1998}(McCartey et al. Cancer Research, 1998, 15:58 2601-5; Disis et al. Ciba Found. Symp. 1994, 187:198-211). These mutant proteins can also be a target of a tumor-specific immune response in multiple types of cancer.

Immunotherapy in cancer patients aims at activating cells of the immune system specifically, especially the so-called cytotoxic T-cells (CTL, also known as "killer cells", also known as CD8-positive T-cells), against tumor cells but not against healthy tissue. Tumor cells differ from healthy cells by the expression of tumor-associated proteins. HLA molecules on the cell surface present the cellular content to the outside, thus enabling a cytotoxic T cell to differentiate between a healthy and a tumor cell. This is realized by breaking down all proteins inside the cell into short peptides, which are then attached to HLA molecules and presented on the cell surface (Rammensee et al., 1993). Peptides that are presented on tumor cells, but not or to a far lesser extent on healthy cells of the body, are called tumor-associated peptides (TUMAPs).

For proteins to be recognized by cytotoxic T-lymphocytes as tumor-specific or -associated antigens, and to be used in a therapy, particular prerequisites must be fulfilled. The antigen should be expressed mainly by tumor cells and not by normal healthy tissues or in comparably small amounts. It is furthermore desirable, that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to a function e.g. in cell cycle control or apoptosis. Additionally, downstream targets of the proteins directly causative for a transformation may be upregulated and thus may be indirectly tumor-associated. Such indirect tumor-associated antigens may also be targets of a vaccination approach. In both cases the presence of epitopes in the amino acid sequence of the antigen is essential, since such peptide ("immunogenic peptide") that is derived from a tumor associated antigen should lead to an in vitro or in vivo T-cell-response.

Basically, any peptide able to bind a MHC molecule may function as a T-cell epitope. A prerequisite for the induction of an in vitro or in vivo T-cell-response is the presence of a T-cell with a corresponding TCR and the absence of tolerance for this particular epitope. T-helper cells play an important role in orchestrating the effector function of CTLs in anti-tumor immunity. T-helper cell epitopes that trigger a T-helper cell response of the TH1 type support effector functions of CD8-positive killer T-cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

Since both types of response, CD8 and CD4 dependent, contribute jointly and synergistically to the anti-tumor effect, the identification and characterization of tumor-associated antigens recognized by either CD8+ CTLs (MHC class I molecule) or by CD4-positive CTLs (MHC class II molecule) is important in the development of tumor vaccines. It is therefore an object of the present invention, to provide compositions of peptides that contain peptides binding to MHC complexes of either class.

First clinical trials using tumor-associated peptides started in the mid-1990s by Boon and colleagues mainly for melanoma. Clinical responses in the best trials have ranged from 10% to 30%. Severe side effects or severe autoimmunity have not been reported in any clinical trial using peptide-based vaccine monotherapy. Mild forms of vitiligo have been reported for some patients who had been treated with melanoma-associated peptides.

However, priming of one kind of CTL is usually insufficient to eliminate all tumor cells. Tumors are very mutagenic and thus able to respond rapidly to CTL attacks by changing their protein pattern to evade recognition by CTLs. To counter-attack the tumor evasion mechanisms a variety of specific peptides is used for vaccination. In this way a broad simultaneous attack can be mounted against the tumor by several CTL clones simultaneously. This may decrease the chances of the tumor to evade the immune response. This hypothesis has been recently confirmed in a clinical study treating late-stage melanoma patients. With only few exceptions, patients that had at least three distinct T-cell responses, showed objective clinical responses or stable disease (Banchereau et al., 2001) as well as increased survival (personal communication with J. Banchereau), while the vast majority of patients with less than three T-cell responses were diagnosed with progressive disease.

A study of the applicants showed a similar effect when patients suffering from renal cell carcinoma were treated with a vaccine composed of 13 different peptides (H. Singh-Jasuja, S. Walter, T. Weinschenk. A. Mayer, P. Y. Dietrich, M. Staehler, A. Stenzl, S. Stevanovic, H. Rammensee, J. Frisch; Correlation of T-cell response, clinical activity and regulatory T-cell levels in renal cell carcinoma patients treated with IMA901, a novel multi-peptide vaccine; ASCO Meeting 2007 Poster #3017; M. Staehler, A. Stenzl, P. Y. Dietrich, T. Eisen, A. Haferkamp, J. Beck, A. Mayer, S. Walter, H. Singh, J. Frisch, C. G. Stief; An open label study to evaluate the safety and immunogenicity of the peptide based cancer vaccine IMA901, ASCO meeting 2007; Poster #3017).

The major task in the development of a tumor vaccine is therefore not only the identification and characterization of novel tumor associated antigens and immunogenic T-helper epitopes derived thereof, but also the combination of different epitopes to increase the likelihood of a response to more than one epitope for each patient. It is therefore an object of the present invention to provide combinations of amino acid sequences of such peptides that have the ability to bind to a molecule of the human major histocompatibility complex (MHC) class-I (HLA class I) or II (HLA class II). It is a further object of the present invention, to provide an effective anti-cancer vaccine that is based on a combination of the peptides.

In the present invention, the inventors isolated and characterized peptides binding to HLA class I or II molecules directly from mammalian tumors, i.e. primary samples of mainly gastric cancer patients, but also from primary tissue samples of glioblastoma, colorectal cancers, renal cell carcinoma, lung cancer, pancreatic cancers, malignant melanoma, and cancer of the stomach.

The present invention provides peptides that stem from antigens associated with tumorigenesis, and have the ability to bind sufficiently to MHC (HLA) class II molecules for triggering an immune response of human leukocytes, especially lymphocytes, especially T lymphocytes, especially CD4-positive T lymphocytes, especially CD4-positive T lymphocytes mediating $T_{H1}$-type immune responses.

The present invention also provides peptides that stem from antigens associated with tumorigenesis, and have the ability to bind sufficiently to MHC (HLA) class I molecules for triggering an immune response of human leukocytes, especially lymphocytes, especially T lymphocytes, especially CD8-positive cytotoxic T-lymphocytes as well as combinations of the two that are particularly useful for vaccination of patients that suffer from cancer.

According to the present invention, the object is solved by providing a pharmaceutical composition comprising at least two peptides containing an amino acid sequence selected from the group consisting of SEQ ID NO 1 to SEQ ID NO 10, and/or containing a variant amino acid sequence that is at least 85% homologous to that of SEQ ID NO 1 to SEQ ID NO 10, and/or a polynucleotide containing a nucleic acid encoding SEQ ID NO 1 to SEQ ID NO or the variant amino acid sequence, and a pharmaceutically acceptable carrier. Pharmaceutical compositions of the present invention may also further comprise at least one additional peptide containing an amino acid sequence selected from the group consisting of SEQ ID NO: 11 to SEQ ID NO: 22, or containing a variant amino acid sequence that is at least 85% identical to that of SEQ ID NO: 11 to SEQ ID NO: 22, or polynucleotide containing a nucleic acid encoding SEQ ID NO: 11 to SEQ TD NO: 22 or the variant amino acid sequence. The peptides may have an overall length of between 8 and 100, preferably between 8 and 30, and most preferably between 8 and 17 amino acids. The peptides may also have non-peptide bonds.

As described herein below, the peptides that form the basis of the present invention have all been identified as presented by MHC class I or II bearing cells. Thus, these particular peptides as well as other peptides containing the sequence (i.e. derived peptides) all elicit a specific T-cell response, although the extent to which such response will be induced might vary from individual peptide to peptide and from individual patient to patient. Differences, for example, could be caused due to mutations in the peptides. The person of skill in the present art is well aware of methods that can be applied to determine the extent to which a response is induced by an individual peptide, in particular with reference to the examples herein and the respective literature.

Preferably the variants of the invention will induce T-cells cross-reacting with the respective peptide of the invention.

The peptides stem from tumor-associated antigens, especially tumor-associated antigens with functions in, e.g., proteolysis, angiogenesis, cell growth, cell cycle regulation, cell division, regulation of transcription, regulation of translation, tissue invasion, etc. Table 4 provides the peptides and the function of the protein the peptides are derived from.

TABLE 4

Peptides of the present invention and function of the parent protein

| SEQ ID NO | Peptide ID | Sequence | Gene Symbol | binds to MHC |
|---|---|---|---|---|
| 1 | CDC2-001 | LYQILQGIVF | CDK1 | HLA-A*024 |
| 2 | ASPM-002 | SYNPLWLRI | ASPM | HLA-A*024 |
| 3 | UCHL5-001 | NYLPFIMEL | UCHL5 | HLA-A*024 |
| 4 | MET-006 | SYIDVLPEF | MET | HLA-A*024 |
| 5 | PROM1-001 | SYIIDPLNL | PROM1 | HLA-A*024 |
| 6 | UQCRB-001 | YYNAAGFNKL | UQCRB | HLA-A*024 |
| 7 | MST1R-001 | NYLLYVSNF | MST1R | HLA-A*024 |
| 8 | PPAP2C-001 | AYLVYTDRL | PPAP2C | HLA-A*024 |
| 9 | SMC4-001 | HYKPTPLYF | SMC4 | HLA-A*024 |
| 10 | MMP11-001 | VWSDVTPLIF | MMP11 | HLA-A* 24 |
| 20 | AVL9-001 | FYISPVNKE | AVL9 | HLA-A*024 |
| 24 | ERBB3-001 | VYIEKNDKL | ERBB3 | HLA-A*024 |

TABLE 5

Additional immunogenic peptides useful in a composition of the invention

| SEQ ID NO | Peptide ID | Sequence | Gene Symbol | binds to MHC |
|---|---|---|---|---|
| 11 | BIR-002 | TLGEFLKLDRERAKN | BIRC5 | HLA-DR and HLA-A*02 |
| 12 | CDC42-001 | DDPSTIEKLAKNKQKP | CDC42 | HLA-DR |
| 13 | CDC42-002 | NKQKPITPETAEKLARD | CDC42 | HLA-DR |
| 14 | SPP1-001 | NGAYKAIPVAQDLNAPS | SPP1 | HLA-DR |
| 15 | BIR-002a | TLGEFLKLDRERAKD | Survivin | HLA-DR and HLA-A*02 |
| 16 | BIR-002b | FTELTLGEF | Survivin | HLA-A1 |
| 17 | BIR-002c | LMLGEFLKL | Survivin | HLA-A2 |
| 18 | BIR-002d | EPDLAQCFY | Survivin | HLA-B35 |
| 19 | NUF2-001 | VYGIRLEHF | NUF2 | HLA-A*024 |
| 20 | AVL9-001 | FYISPVNKL | AVL9 | HLA-A*024 |
| 21 | ABL1-001 | TYGNLLDYL | ABL1 | HLA-A*024 |
| 22 | NUF2-002 | RFLSGIINF | NUF2 | HLA-A*024 |
| 23 | (HBV-001) | FLPSDFFPSV | control peptide | |

Cell Division Cycle 2 Protein (CDC2)

CDC2, also known as p34cdc2 or Cdk1 (Cyclin-dependent kinase 1), belongs to the Cdks, a family of serine/threonine protein kinases, and plays a key role in cell cycle control. It is known as the main regulator of the G2-to-M transition. At the end of interphase, it is activated by binding to A-type cyclins and facilitates the onset of mitosis. After breakdown of the nuclear envelope, A-type cyclins are degraded and replaced by cyclin B. The complex between CDC2 and cyclinB forms the mitosis promoting factor (MPF), which is essential for driving cells through mitosis.

Active CDC2 phosphorylates more than 70 substrates. For example, phosphorylation of the "linker" histone H1 leads to a relaxation of chromatin structure and transcription of specific genes, and phosphorylation of RNA-polymerase II enhances transcription (Cisek and Corden, 1989). BRCA2 phosphorylation stimulates homologous recombination-dependent repair (Esashi et al., 2005), and FOXO1 phosphorylation inhibits its transcriptional activity, resulting in cell proliferation and survival. Phosphorylation of separase inhibits premature sister chromatid separation (Stemmann et al., 2001). CDC2 activity is switched off again during anaphase, as the anaphase-promoting complex/cyclosome (APC/C) ubiquitinates cyclin B, leading to its degradation.

The function of CDC2 in mitosis is non-redundant and cannot be compensated by the activity of other Cdks such as Cdk2, 4 and 6. By contrast, CDC2 was reported to function in other phases of the cell cycle such as the G1-S transition as well, and it is able to substitute for the "interphase Cdks". Thus, CDC2 was proposed to be the only essential cell cycle Cdk. Apart from its expression and function in cell cycle, it was reported that in some cases CDC2 is expressed in apoptotic conditions, and that enhanced activity can lead to mitotic catastrophe. Overexpression of CDC2 was found in several cancers, although the expression of other cell cycle proteins such as cyclins is dysregulated even more frequently. Among the cancer types overexpressing CDC2 are prostate carcinoma, oral cavity carcinomas, oral squamous carcinoma (OSCC), acute myeloid leukemia (AML) (Qian et al., 2009), *H. pylori*-induced MALT lymphoma (Banerjee et al., 2000) and colon carcinoma (Yasui et al., 1993). In several cases, overexpression was correlated with poor prognosis. In gastric carcinoma (GC), overexpression and/or enhanced activity has been reported (14 of 23 cases), and it was suggested that CDC2 overexpression could play a causative role. Furthermore, CDC2 was found to be among a set of genes active during mitosis, which, if overexpressed, lead to chromosomal instability of tumors. Inhibitors of CDC2 and other Cdks have been considered as drug candidates for cancer therapy (Shapiro, 2006).

Abnormal Spindle-Like Microcephaly Associated Protein (ASPM)

Abnormal spindle-like microcephaly associated (ASPM) gene is the human orthologue of the *Drosophila* abnormal spindle (asp) and the most commonly mutated gene of autosomal recessive primary microcephaly. In human, the defective neurogenesis caused by homozygous mutation of ASPM leads to microcephaly and mental retardation.

The most common cause of primary autosomal recessive microcephaly (MCPH) appears to be mutations in the ASPM gene which is involved in the regulation of neurogenesis. ASPM is localized in the spindle poles during mitosis.

ASPM inhibition by siRNA-mediated knockdown inhibits tumor cell proliferation and neural stem cell proliferation, supporting ASPM as a potential molecular target in glioblastoma. ASPM was overexpressed in glioblastoma relative to normal brain. The expression of ASPM may be used as a marker for glioma malignancy and represents a potential therapeutic target. ASPM overexpression is a molecular marker predicting enhanced invasive/metastatic potential of hepatocellular carcinoma HCC, higher risk of early tumor recurrence ETR regardless of p53 mutation status and tumor stage, and hence poor prognosis. ASPM was also upregulated in immortalized cells, cancer cells, and non-small-cell lung cancer (NSCLC) tissues (Jung et al., 2009).

Ubiquitin Carboxyl-Terminal Hydrolase L5 (UCHL5)

Ubiquitin carboxyl-terminal hydrolase L5 (UCHL5), also known as Ubiquitin C-terminal hydrolase (UCH37) or INO80R, is a deubiquitinase that is associated with the proteasome. It disassembles protein-attached polyubiquitin chains from the distal end by cleaving the isopeptide bond between the C-terminal Cys76 and Lys48 (Nishio et al., 2009).

UCHL5 binds to hRpn13 (also known as Adrm1), a component of the 19S (PA700) regulatory particle of the proteasome, which activates its isopeptidase activity. hRpn13 also functions as receptor for ubiquitin, thereby coupling substrate recognition to deubiquitination. UCHL5 can also bind to Rpn10/S5a, another component of the 19S particle located between its "lid" and its "base", but this interaction fails to activate UCHL5. UCH37 could rescue poorly ubiquitinated substrates or other slowly degraded Ub-conjugates from proteolysis. Alternatively, it may also enhance degradation by facilitating release of polyubiquitinated substrates from their initial binding site in the 19S regulatory complex for translocation into the proteolytic core, the 20S particle of the 26S proteasome. In the nucleus, UCHL5 is also associated with the Ino80 chromatin-remodeling complex. Upon binding of a proteasome, it becomes activated and may contribute to the regulation of transcription or DNA repair that has been suggested to be mediated by Ino80 and the proteasome. The function of UCHL5 might at least partly be exerted by other proteins, as RNAi-mediated knockdown of UCHL5 had no detectable effect on cell growth, proteasome structure or proteolytic capacity, although it accelerated cellular protein degradation.

Ubiquitin specific proteases like UCHL5 are involved in several processes such as control of cell cycle progression, differentiation, DNA replication and repair, transcription, protein quality control, immune response and apoptosis. There is at least some evidence that UCHL5 contributes to malignant transformation. Its activity has been shown to be upregulated in human cervical carcinoma tissue as compared to adjacent normal tissue. It is able to deubiquitinate and thereby stabilize the TGF-beta receptor and its downstream mediators, the Smads, thereby enhancing TGF-beta signaling. Enhanced TGF-beta signaling can act as a tumor promoter in late stages of cancer progression, although it has a dual function and can also be a tumor suppressor in early stages and before initiation (Wicks et al., 2005; Wicks et al., 2006; Horton et al., 2007; Bierie and Moses, 2006).

c-Met

See for example EP 08008292.8 and EP1507795B1. Furthermore, constitutive c-Met activation through phosphorylation has also been identified as an important mechanism of oncogenesis in human clear-cell renal cell carcinoma (Nakaigawa et al., 2006).

MET over-expression, often induced by tumor hypoxia, leads to constitutive activation of the receptor and correlates with poor prognosis. Silencing the endogenous MET gene, over-expressed in tumor cells, results in impairment of the execution of the full invasive growth program in vitro, lack of tumor growth and decreased generation of experimental metastases in vivo. Notably, silencing MET in already established metastases leads to their almost complete regression (Corso et al., 2008).

Macrophage-Stimulating Protein Receptor (MST1R)

The MST1R (alias RON) receptor is a member of the Met family of cell surface receptor tyrosine kinases and is primarily expressed on epithelial cells and macrophages. Like c-MET, RON is expressed by a variety of epithelial-derived tumors and cancer cell lines and it is thought to play a functional role in tumorigenesis. Clinical studies have shown that MST1R overexpression is associated with both worse patient outcomes as well as metastasis. MST1R expression is significant in gastric carcinoma tissue and corresponding paraneoplastic tissue, but is not expressed in normal gastric mucosa (Zhou et al., 2008). MST1R receptor can induce cell migration, invasion, proliferation and survival in response to its respective ligand. Moreover, MST1R possess oncogenic activity in vitro, in animal models in vivo and is often deregulated in human cancers (Dussault and Bellon, 2009). Data show that knockdown of MST1R in prostate cancer cells results in significantly less endothelial cell chemotaxis when compared with MST1R-expressing cells in vitro as well as in reduced tumor growth and decreased microvessel density after orthotopic transplantation into the prostate in vivo. It has been shown that RNA interference-mediated knockdown of MST1R kinase in a highly tumorigenic colon cancer cell line led to reduced proliferation as compared with the control cells.

Structural Maintenance of Chromosomes Proteins 4 (SMC4)

Structural maintenance of chromosomes (SMC) proteins are chromosomal ATPases, highly conserved from bacteria to humans, that play fundamental roles in many aspects of higher-order chromosome organization and dynamics.

The SMC4 protein is a core component of the condensin complex that plays a role in chromatin condensation and has also been associated with nucleolar segregation, DNA repair, and maintenance of the chromatin scaffold. Eukaryotes have at least six SMC proteins in individual organisms, and they form three distinct heterodimers with specialized functions: SMC2 and SMC4 function as the core of the condensin complexes that are essential for chromosome assembly and segregation.

Analysis of mRNA levels in 25 different normal tissues by RT-PCR shows that this gene is expressed highly in normal prostate and salivary gland, very weakly in colon, pancreas, and intestine, and not at all in other tissues. RT-PCR studies on human cancer samples show that the RNA is expressed highly in many cancer cell lines and cancer specimens, including 26 of 33 human breast cancers, 3 of 3 prostate cancers, 3 of 3 colon cancers, and 3 of 3 pancreatic cancers (Egland et al., 2006).

AVL9

Surprisingly, this protein was found as source protein, since only poor data is available about the AVL9 protein and the function of the corresponding gene.

Kinetochore Protein Nuf2

NUF2 (CDCA-1) gene encodes a protein that is highly similar to yeast Nuf2, a component of a conserved protein complex associated with the centromere. Yeast Nuf2 disappears from the centromere during meiotic prophase when centromeres lose their connection to the spindle pole body, and plays a regulatory role in chromosome segregation. It was shown that survivin and hNuf2 csiRNAs temporally knockdown their mRNAs causing multinucleation and cell death by mitotic arrest, respectively (Nguyen et al., 2006). Nuf2 and Heel are required for organization of stable microtubule plus-end binding sites in the outer plate that are needed for the sustained poleward forces required for biorientation at kinetochores (DeLuca et al., 2005).

Immunohistochemical analysis using lung cancer tissue microarray confirmed high levels of CDCA1 and KNTC2 proteins in the great majority of lung cancers of various histologic types. Their elevated expressions were associated with poorer prognosis of NSCLC patients. Inhibition of their binding by a cell-permeable peptide carrying the CDCA1-derived 19-amino-acid peptide (11R-CDCA1(398-416)) that correspond to the binding domain to KNTC2 effectively suppressed growth of NSCLC cells (Hayama et al., 2006). siRNA-mediated knockdown against CDCA1 or KNTC2 has been found to inhibit cell proliferation and induction of apoptosis in NSCLC, ovarian cancer, cervical cancer, gastric cancer, colorectal cancer and glioma (Kaneko et al., 2009). CDCA 1 gene is differentially expressed in cervical cancer (expression of mRNA validated by real-time PCR and protein by immunohistochemistry) (Martin et al., 2009). RT-PCR with surgically resected gastric cancer tissues (diffuse type, 6; intestinal type, 4) confirmed that two variants of CDCA1 were upregulated in cancer tissues. Alternative splicing variants, especially in CDCA1, were detected in this study and may be potentially useful as diagnostic markers and/or novel targets for anticancer therapy (Ohnuma et al., 2009).

Lipid Phosphate Phosphohydrolase 2 (PPAP2C)

The protein encoded by this gene is a member of the phosphatidic acid phosphatase (PAP) family. PAPs convert phosphatidic acid to diacylglycerol, and function in de novo synthesis of glycerolipids as well as in receptor-activated signal transduction mediated by phospholipase D. Three alternatively spliced transcript variants encoding distinct isoforms have been reported.

PPAP2C is a potentially novel target that is up-regulated in transformed primary human adult mesenchymal stem cells MSC. Knockdown of PPAP2C decreases cell proliferation by delaying entry into S phase of the cell cycle and is transcriptionally regulated by p53. Some data suggest that overexpression of PPAP2C, observed in numerous human cancers, may be a requirement for increased cell proliferation (Flanagan et al., 2009). A study demonstrates that PPAP2C is a regulator of cell cycle progression in fibroblasts. Overexpression of PPAP2C, but not a catalytically inactive mutant, caused premature S-phase entry, accompanied by premature cyclin A accumulation. These represent substantial changes in the rate of S-phase entry that could have implications in processes such as mitogenesis, migration, wound healing, development, and tumorgenesis.

Ubiquinol-Cytochrome c Reductase Binding Protein (UQCRB)

The UQCRB-gene encodes a protein that is part of the ubiquinol-cytochrome c oxidoreductase complex which contains ten nuclear-encoded and one mitochondrial-encoded subunits. The encoded protein binds ubiquinone and participates in the transfer of electrons when ubiquinone is bound. Mutations in this gene are associated with mitochondrial complex III deficiency. A pseudogene has been described on the X chromosome.

The UQCRB-gene may be a potential oncogene or a tumour suppressor gene in pancreatic ductal adenocarcinoma (Harada et al., 2009). The UQCRB-gene is overexpressed in hepatocellular carcinoma (Jia et al., 2007)

Prominin 1 (Prom1)

Prominin-1, also called CD133, was originally identified as a molecule specific for CD34+ hematopoetic progenitor cells and later on shown to be a marker for normal stem cells and cancer stem cells (CSCs) of various tissues (Mizrak et al., 2008). However, little is known about its function. As it is located mainly in protrusions of the plasma membrane, such as the microvilli of epithelial cells, a functional role was ascribed to prominin-1 as an 'organizer' of plasma membrane topology. As it was found to interact with cholesterol, it might be important in maintaining an appropriate lipid composition within the plasma membrane.

Prominin-1 is used as CSC marker in many human tumors. Only a small percentage of tumor cells is usually positive for prominin-1, as expected for a CSC marker. Depending on the tumor type, the number of positive cells per tumor mass reaches from 1 to 15% and is mostly around 2%. Tumors where prominin-1 expressing cells have been shown to be CSCs by functional tests (such as sphere formation, high capacity to initiate of tumor growth in immunodeficient mice and asymmetric division/self-renewal/pluripotency) are:

colon cancer (2-2.5% of tumor mass) (Todaro et al., 2007; Ricci-Vitiani et al., 2007),
liver cancer (Ma et al., 2007; Suetsugu et al., 2006; Yin et al., 2007),
pancreatic cancer (Hermann 2007; Wang 2009),
prostate cancer (1% of tumor mass) (Richardson et al., 2004),
brain tumors of different phenotypes (Singh et al., 2003; Singh et al., 2004),
leukemias such as acute lymphoblastic leukemia, ALL (Cox et al., 2009),
melanoma (Monzani et al., 2007; Rappa et al., 2008),
lung cancer (Chen and O'Shea, 2008; Eramo et al., 2008; Tirino et al., 2009),
Ewing's sarcoma (Suva et al., 2009),
endometrial cancer (Rutella et al., 2009),
oral squamous cell carcinoma (Zhang et al., 2009) and
head and neck squamous cell carcinoma (Harper et al., 2007).

Moreover, several studies show an increased prominin-2008 expression in cancerous tissue as compared to healthy tissue, and most of them find a correlation of prominin-1 expression with clinical parameters such as overall survival, tumor stage or metastasis. Examples are non-small cell lung cancer, malignant melanoma, retinoblastoma, neuroblastoma and synovial carcinoma. Prominin-1 expression also correlated with poor prognosis in glioma, pancreatic cancer (up to 15% PROM1+ cells), colorectal, rectal and colon cancer and ductal breast carcinoma. Interestingly, PROM1 mRNA is upregulated in PBMCs of cancer patients with metastatic disease, especially in patients with bone metastasis, and PROM1 expression in PBMCs is a prognostic factor for overall survival. No correlation with prognosis was found in ovarian cancer.

In diffuse gastric cancer, PROM1 expression was suggested based on an in silico analysis (Katoh and Katoh, 2007) and overexpression in gastric cancer compared to normal stomach tissue at the protein level was reported by (Smith et al., 2008). However, (Boegl and Prinz, 2009) reported that prominin-1 expression was reduced in gastric cancer, especially in later stages, and claimed that prominin-1 expression rather correlates with angiogenesis—which is also reduced in later stages—than with tumor growth. A study using gastric cancer cell lines (Takaishi et al., 2009) claims that CD44, but not prominin-1 is a CSC marker in gastric cancer.

Evidence for involvement of prominin-1 expressing cells in tumor formation was provided by (Zhu et al., 2009), who reported that in a mouse intestinal cancer model, all neoplastic cells arose from Prom1+ cells, but only 7% retained the Prom1+ phenotype. Apart from that, prominin-1(+) cells have been shown to contribute to tumor angiogenesis. As expected for CSCs, prominin-1(+) cells have been shown to be chemoresistant due to activation of the Akt survival pathway (Ma 2008). (Bertolini et al., 2009) report that they do not respond to cisplatin treatment. They are resistant to TRAIL- and Fas-induced apoptosis due to upregulation of FLIP. They protect themselves from apoptosis by secretion of IL-4. However, they might be accessible by the immune system, as they can be killed by NK cells (Castriconi et al., 2007; Pietra et al., 2009) and cytotoxic T cells (Brown et al., 2009).

Matrix Metalloproteinase 11 (MMP11)

Matrix metalloproteinase 11 (MMP11) was proposed to play a role during several physiological processes requiring tissue remodeling, such as development, postlactating involution of the mammary gland, wound healing and scar formation and during the menstrual cycle. It has also been proposed to negatively regulate fat homeostasis by reducing adipocyte differentiation. In contrast to other MMPs, it is not able to cleave typical extracellular matrix molecules—except collagen VI. However, other substrates have been identified such as alpha 2-macroglobulin, certain serine protease inhibitors (serpins) including alpha 1 anti-trypsin, insulin-like growth factor-binding protein-1 and the laminin receptor. MMP11 was discovered as a gene that is overexpressed specifically in stromal cells surrounding invasive breast carcinoma. Further studies confirmed its expression in the tumor-surrounding stroma of breast carcinoma and of other cancer types, such as skin cancer, non-small cell as well as small cell lung carcinomas, head and neck squamous cell carcinoma, colon and colorectal carcinoma, epithelial cancer of the larynx, oesophageal carcinoma, oral carcinoma, pancreatic carcinoma, carcinoma of the urinary bladder, ovarian carcinomas, renal cell carcinoma, atypical meningioma, papillary thyroid carcinoma, brain tumors (MMP11 was expressed in astrocytomas, but only to a low extent in oligodendrogliomas, and in malignant gliomas), salivary duct carcinoma, cervical cancer, extranodal T/NK-cell lymphomas, Non-Hodgkins Lymphoma and prostate carcinoma. It was stated that MMP11 is overexpressed in the stroma of most invasive human carcinomas, but rarely in sarcomas and other nonepithelial tumors Mostly, MMP11 is expressed in stroma cells directly adjacent to the tumor, whereas the tumor cells themselves, normal tissues and stroma cells distant from the tumor are negative. However, this cannot be generalized as in some cases MMP11 was also found in noncancerous tissue such as that of the colon or in tumor cells, e.g. in tumors of the pancreas, breast, arachnoid membrane and stomach. Higher levels of MMP11 are correlated with a malignant phenotype/higher invasiveness and had prognosis. However, in papillary thyroid carcinomas, MMP11 expression was inversely linked to aggressive characteristics.

A role in angiogenesis is not probable, as MMP11 expression did not correlate with microvessel density. Rather, it appears to enhance cancer cell survival and suppress apoptosis. It was proposed that MMP11 from fibroblasts leads to the stimulation of the IGF-1R pathway in carcinoma cells, thus enhancing their proliferative capacity. Its capacity to lead to adipocyte dedifferentiation supports cancer by accumulation of pen tumoral fibroblast-like cells which favor cancer cell survival and tumor progression (Motrescu and Rio, 2008), MMP11 was found in tumor tissue as well as in serum of gastric cancer patients, and expression correlated with metastasis (Yang et al., 2008). Moreover, (Deng et al., 2005) showed that MMP11 is highly expressed in tumor cell lines and primary tumor of gastric cancer—in contrast to other cancer types not exclusively in the stroma—and that it appears to enhance tumor cell proliferation.

ABL1

The ABL1 protooncogene encodes a cytoplasmic and nuclear protein tyrosine kinase of the Src family that has been implicated in processes of cell differentiation, cell division, cell adhesion, and stress response (Yoshida, 2007). C-Abl shuttles between the nuclear and cytoplasmic compartments. Nuclear c-Abl is involved in cell growth inhibition and promotion of apoptosis. In contrast, the role of cytoplasmic c-Abl is less well described. There are hints for a role in morphogenesis and F-actin dynamics, and a role in signalling induced by extracellular stimuli like growth factors and integrin ligands. Cytoplasmic c-Abl was reported to promote mitogenesis. C-Abl mitogenic substrates have not yet been identified, but they are likely to include regulators of small GTPases of the Rho family, especially Vav and Sos members.

The DNA-binding activity of the ubiquitously expressed ABL1 tyrosine kinase is regulated by CDC2-mediated phosphorylation, suggesting a cell cycle function for ABL1. Activity of c-Abl protein is negatively regulated by its SH3 domain, and deletion of the SH3 domain turns ABL1 into an oncogene. The c-Abl nonreceptor tyrosine kinase regulates actin responses in nonhematopoietic cells. Some studies identify c-Abl as a key player in the signaling cascade, leading to actin reorganization during T-cell activation (Huang et al., 2008).

Mutations in the ABL1 gene are associated with chronic myelogenous leukemia (CML). In CML, the gene is activated by being translocated within the BCR (breakpoint cluster region) gene on chromosome 22. This new fusion gene, BCR-ABL, encodes an unregulated, cytoplasm targeted tyrosine kinase which allows the cells to proliferate without being regulated by cytokines. This in turn allows the cell to become cancerous (Zhao et al., 2009). Activated c-Abl tyrosine kinase, not as a fusion protein, plays an important role in malignant solid tumors of lung and breast (Lin and Arlinghaus, 2008).

Recent observations indicate that c-Abl is also deregulated in solid tumors. High cytoplasmic kinase activities have been detected in breast carcinomas and NSCLC. Overexpression however, not sufficient and constitutive kinase activity required protein phosphorylation. In breast cancer cells, c-Abl phosphorylation is induced by plasma membrane tyrosine kinases, including SFK, EGFR family members and the IGF-1 receptor. ABL fusion proteins have not been detected in solid tumors.

ABL1 and gastric cancer—In a immunohistochemical study of ABL1 expression, a wide range of normal fetal and adult human tissues and a variety of tumour types were examined. Most tumours showed focal or weak ABL immunoreactivity. The most intense staining was seen in chondrosarcoma, liposarcoma, and diffuse gastric (signet ring) adenocarcinoma. In the two latter cases. ABL was also expressed on tumor microvessels, indicating a possible role in angiogenesis.

Recent studies have revealed that infection with cagA-positive *Helicobacter pylori* plays an essential role in the development of gastric carcinoma. *H. pylori* blocks EGFR endocytosis and receptor degradation upon prolonged infection of gastric epithelial cells. Moreover, this inhibition occurs via a CagA-dependent, but CagA phosphorylation-independent activation of the non-receptor kinase c-Abl, which in turn phosphorylates the EGFR target site pY1173 (Bauer et al., 2009). Selective inhibition of c-Abl kinase activity by STI571 or shRNA abrogates sustained cytotoxin-associated gene A (CagA) phosphorylation and epithelial cell migration, indicating a pivotal role of c-Abl in *H. pylori* infection and pathogenicity (Poppe et al., 2007).

An example of kinase blockers is Imatinib (Imatinib mesylate, Gleevec, STI571), the inhibitor of Bcr/Abl oncoprotein, which has become a first-line therapy for chronic myelogenous leukemia (Pytel et al., 2009). Imatinib has been approved for the treatment of patients with advanced gastrointestinal stromal tumour (GIST), in which KIT, a tyrosine kinase receptor, is abnormally expressed (Croom and Perry, 2003). Another kinase inhibitor used recently in cancer therapy is Dasatinib (BMS-354825) which is specific for ABL non-receptor cytoplasmic (Pytel et al., 2009). Nilotinib is an oral second-generation bcr-abl TKI indicated for the treatment of imatinib resistant or -intolerant Ph+ CML-CP and -AP in adults (Deremer et al., 2008).

SEQ ID NO 13, SEQ ID NO 14 and SEQ ID NO 15 are disclosed in WO 2007/028574, CDC42 (cell division cycle 42) is a protein involved, in regulation of the cell cycle. The protein is a small GTPase of the Rho-subfamily, which regulates signaling pathways that control diverse cellular functions including cell morphology, migration, endocytosis and cell cycle progression. CDC42 was found to be highly over-expressed in glioblastoma.

WO 2004/067023 describes WIC Class I-restricted peptides derived from the tumor associated antigen survivin, which peptides are capable of binding to Class I HLA molecules at a high affinity.

Secreted phosphoprotein 1 (SPP1), also known as bone sialoprotein I (BSP-1), early T-lymphocyte activation (ETA-1), and, most commonly as osteopontin (OPN), is a human gene product, which is also conserved in other species. Osteopontin has been implicated as an important factor in bone remodeling. Specifically, research suggests that it plays a role in anchoring osteoclasts to the mineral matrix of bones. The organic part of bone is about 20% of the dry weight, and counts in, other than osteopontin, collagen type I, osteocalcin, osteonectin, bone sialo protein and alkaline phosphatase. Collagen type I counts for 90% of the protein mass.

OPN binds to several integrin receptors including $\alpha 4\beta 1$, $\alpha 9\beta 1$, and $\alpha 9\beta 4$ expressed by leukocytes. These receptors have been well-established to function in cell adhesion, migration, and survival in these cells. Therefore, recent research efforts have focused on the role of OPN in mediating such responses.

Osteopontin is expressed in a range of immune cells, including macrophages, neutrophils, dendritic cells, and T and B cells, with varying kinetics. OPN is reported in act as an immune modulator in a variety of manners. Firstly, it has chemotactic properties, which promote cell recruitment to inflammatory sites. It also functions as an adhesion protein, involved in cell attachment and wound healing. In addition, OPN mediates cell activation and cytokine production, as well as promoting cell survival by regulating apoptosis.

Activated T cells are promoted by IL-12 to differentiate towards the Th1 type, producing cytokines including IL-12 and IFN$\gamma$. OPN inhibits production of the Th2 cytokine IL-10, which leads to enhanced Th1 response, OPN influences cell-mediated immunity and has Th1 cytokine functions. It enhances G cell immunoglobulin production and proliferation. Recent studies in 2008 suggest that OPN also induces mast cell degranulation, [Nagasaka A, Matsue H, Matsushima H, et al. (February 2008). "Osteopontin is produced by mast cells and affects IgE-mediated degranulation and migration of mast cells", Eur. J. Immunol. 38 (2):

189-99] The researchers observed that IgE-mediated anaphylaxis was significantly reduced in OPN knock-out mice compared to wild type mice. The role of OPN in activation of macrophages has also been implicated in a cancer study, when researchers discovered that OPN-producing tumors were able to induce macrophage activation compared to OPN-deficient tumors.

OPN is an important anti-apoptotic factor in many circumstances. OPN blocks the activation-induced cell death of macrophages and T cells as well as fibroblasts and endothelial cells exposed to harmful stimuli, OPN prevents non-programmed cell death in inflammatory colitis.

The fact that OPN interacts with multiple cell surface receptors which are ubiquitously expressed makes it an active player in many physiological and pathological processes including wound healing, bone turnover, tumorigenesis, inflammation, ischemia and immune responses. Therefore, manipulation of plasma OPN levels may be useful in the treatment of autoimmune diseases, cancer metastasis, osteoporosis and some forms of stress.

It has been shown that OPN drives IL-17 production; OPN is overexpressed in a variety of cancers, including lung cancer, breast cancer, colorectal cancer, stomach cancer, ovarian cancer, melanoma and mesothelioma; OPN contributes both glomerulonephritis and tubulointerstitial nephritis; and OPN is found in atheromatous plaques within arteries. Thus, manipulation of plasma OPN levels may be useful in the treatment of autoimmune diseases, cancer metastasis, osteoporosis and some forms of stress.

Human Epidermal Growth Factor Receptor 3 (ERBB3)

ERBB3 encodes a member of the epidermal growth factor receptor (EGFR) family of receptor tyrosine kinases. It is activated by neuregulins, by other ERBB and nonERBB receptors as well as by other kinases, and by novel mechanisms. Downstream it interacts prominently with the phosphoinositol 3-kinase/AKT survival/mitogenic pathway, but also with GRB, SHC, SRC, ABL, rasGAP, SYK and the transcription regulator EBP1 (Sithanandam and Anderson 413-48).

Studies of ERBB3 expression in primary cancers and of its mechanistic contributions in cultured cells have implicated it, with varying degrees of certainty, with causation or sustenance of cancers of the breast, ovary, prostate, certain brain cells, retina, melanocytes, colon, pancreas, stomach, oral cavity and lung (Sithanandam and Anderson 413-48). ERBB3 protein was detected by immunohisto-chemistry in epithelial cells throughout the gastrointestinal tract, including squamous epithelium of the oropharynx and esophagus, parietal cells of the stomach and surface enterocytes of small and large bowel. ERBB3 showed increased expression in gastric cancers (Poller et al. 275-80; Sanidas et al. 935-40). Gastric cancer cell lines all expressed ERBB3 and a truncated, secreted product. Strong evidence for a key role for ERBB3 in gastric malignancy came from a study of poorly differentiated signet-ring cell gastric carcinomas (Kobayashi et al. 1294-301). Zhang et al investigated the expression of ERBB3 in gastric cancer of two pathologic types (intestinal type and diffuse type) using immunohistochemistry (IHC). The diffuse type of GC exhibited a significantly higher rate of ERBB3 overexpression than the intestinal type (26.2% vs. 5.0%, p<0.01). The selective overexpression of ERBB3 in the two histologic types of gastric cancer is strongly associated with a poor prognosis (Zhang et al. 2112-18), ERBB3 expression was significantly associated with parameters involved with tumor progression, including the depth of tumor invasion, involved lymph nodes, distant metastasis, tumor stage, and recurrent disease (Hayashi et al. 7843-49). The expression and coexpression of EGFR, c-erbB-2 and c-erbB-3 in 2.1 gastric cancers and 21) chronic gastritis' were examined using immunohistochemistry on fresh frozen tissues considering clinicopathological variables. Generally, gastric cancer patients showed a higher incidence of EGFR, c-erbB-2 and d-erbB-3 overexpression than the group with chronic gastritis (81% and 43%; 38% and 45%; 35% and 20%, respectively), however, statistically significant differences were found only for EGFR expression (p=0.01) (Slesak et al. 2727-32).

Several approaches for therapeutic targeting of ERBB3 have been tried experimentally. RNA aptamers to the extracellular domain of ERBB3 inhibited NRG-induced ERBB3/ERBB2 heterodimerization, ERBB2 phosphorylation and growth of MCF7 breast cancer cells (Chen et al. 9226-31). A synthetic designer zinc finger transcription factor inhibitory to ERBB3 gene expression in A431 squamous cell carcinoma cells resulted in reduced proliferation and migration, and the repression of ERBB3 expression had a bigger effect than changing ERBB2 (Lund et al. 9082-91). The vitamin E isomer γ-tocotrienol inhibited mammary cell proliferation by specific block of ERBB3 activation and of downstream stimulation of the PI3K/AKT pathway (Samant and Sylvester 563-74). Micro-RNA 125a reduced ERBB3 RNA and protein, activation of AKT and cell growth and invasiveness of SKBR3 mammary carcinoma cells (Scott et al. 1479-86). Downregulation of ERBB3 by siRNA in breast cancer cells abrogated their secondary resistance to tyrosine kinase inhibitors and allowed induction of apoptosis (Sergina et al. 437-41). Small inhibitory RNA (siRNA) to ERBB3 or AKT is showing promise as a therapeutic approach to treatment of lung adenocarcinoma (Sithanandam et al. 1847-59).

Survivin (BIRC5)

Expression of BIRC5 (survivin), a member of the inhibitor of apoptosis protein (IAP) family, is elevated in fetal tissues and in various human cancers. WO 2004/067023 describes MHC Class I-restricted peptides derived from the tumor associated antigen survivin, which peptides are capable of binding to Class I HLA molecules at a high affinity. Survivin seems to be capable of regulating both cellular proliferation and apoptotic cell death. Especially in glioblastoma, very high levels of survivin expression are detectable (Angileri et al., 2008). It is suggested that survivin overexpression in brain gliomas might play an important role in malignant proliferation, anti-apoptosis and angiogenesis (Zhen et al., 2005; Liu et al., 2006). Especially for glioblastoma, but also for other tumor entities, survivin expression was significantly associated with malignancy grade (with highest survivin expression in glioblastoma) and shorter overall survival times compared with patients who had survivin-negative tumors (Kajiwara et al., 2003; Saito et al., 2007; Ueinatsu et al., 2005; Mellai et al., 2008; Grunda et al., 2006; Xie et. al., 2006; Sasaki et al., 2002; Chakravarti et al., 2002).

Hepatitis B Core Antigen

For the Hepatitis B virus (HBV) core protein HBc immunogenic peptides are well known (Bertoletti et al., 1993; Livingston et al., 1997). A ten-amino acid peptide from HBc may be included as a positive control for patients' immunocompetence and successful immunizations into cancer vaccines based on the present invention.

TABLE 6

Cancer associated functions of the source proteins

| Cancer-associated functions of source proteins/TUMAP | HLA class I TUMAPs | | | | | | | | | | | | HLA class II TUMAP |
|---|---|---|---|---|---|---|---|---|---|---|---|---|---|
| activity | ASPM-002 | CDC2-001 | MET-006 | MST1R-001 | PROM1-001 | UCHL5-001 | MMP11-001 | SMC4-001 | PPAP2C-001 | AVL9-001 | UQCRB-001 | ABL1-001 | NUF2-001 | BIRC5-002 |
| Oncofetal protein (OF)/ Cancer-Testis-Antigen (CT) activity | − | − | − | − | − | − | − | − | − | ? | − | − | CT | OF |
| Tumorigenesis (cell cycle progression, proliferation) | + | + | + | + | + | ? | + | − | + | ? | − | + | + | + |
| Tumor invasion, migration, metastasis | + | − | + | + | + | ? | + | − | − | ? | − | + | − | − |
| Cancer-associated signaling pathways | Downstream of EGFR | Cell cycle (G2/M) | Ras/MAPK, PI3K, PLC | Similar to MET | Akt | TGF-beta (enhanced) | IGF1R pathway | mitosis | Cell cycle | ? | | EGFR, PI3K, STAT3, +1, Rac/JNK, Erk5, eta-catenin | cell division | Inhibition of apoptosis |
| Anti-apoptotic effects | (+) | (+) | + | + | − | − | + | − | − | ? | − | + | − | + |
| Angiogenesis | − | − | + | (+) | (+) | − | − | (+) | (+) | ? | − | + | − | − |
| Cancer stem-like cells | − | − | − | − | + | − | − | ? | ? | ? | − | − | − | + |
| Overexpression in GC | ? | + | + | + | (+) | ? | + | ? | ? | ? | ? | + | + | + |
| Overexpression in other cancers | + | + | + | + | + | (+) | + | + | + | ? | + | + | + | + |
| Poor prognosis | + | + | + | + | + | ? | + | − | ? | ? | − | + | + | + |
| Advanced stages | − | ? | + | ? | − | − | − | − | + | ? | − | − | − | + |

Ranking "−" < "(+)" < "+"; "?" means that the situation is currently unknown

As it can be seen from Table 6, the person skilled in the art can easily adapt the composition of the application at hand to the patient and/or tumor specific and select the TUMAPs accordingly.

In a preferred embodiment of the invention the pharmaceutical composition comprises at least two peptides, one of them containing an amino acid sequence according to SEQ ID No 1 and containing further a peptide containing an amino acid sequence according to SEQ ID No 11.

In a preferred embodiment of the invention the pharmaceutical composition comprises at least two peptides, one containing an amino acid sequence according to SEQ ID No 1 and an amino acid sequence according to SEQ ID No 2 and/or SEQ ID No 11.

In a preferred embodiment of the invention the pharmaceutical composition comprises at least two peptides containing an amino acid sequence according to SEQ ID No SEQ ID No 3 and an amino acid sequence according to SEQ ID No 2 and/or SEQ ID No 11.

In a preferred embodiment of the invention the pharmaceutical composition comprises at least two peptides containing an amino acid sequence according to SEQ ID No SEQ ID No 1 and an amino acid sequence according to SEQ ID No 7 and optionally SEQ ID No 11.

In a preferred embodiment of the invention the pharmaceutical composition comprises at least two peptides containing an amino acid sequence according to SEQ ID No SEQ ID No 2 and an amino acid sequence according to SEQ ID No 7 and optionally SEQ ID No 11.

In a preferred embodiment of the invention the pharmaceutical composition comprises at least two peptides containing an amino acid sequence according to SEQ ID No SEQ ID No 3 and an amino acid sequence according to SEQ ID No 7 and optionally SEQ ID No 11.

In an even more preferred embodiment the pharmaceutical composition comprises at least one more peptides containing an amino acid sequence selected from the group consisting of SEQ ID NO 2 to SEQ ID NO 10 and SEQ ID No 11 to SEQ ID No 22 and SEQ ID NO 24 and/or an amino acid sequence that is at least 85% identical to that of SEQ ID NO 2 to SEQ ID NO 10 and SEQ ID No 11 to SEQ ID No 22 and SEQ ID NO 24 and/or a polynucleotide containing a nucleic acid encoding SEQ ID NO 2 to SEQ ID NO 10 and SEQ ID No 11 to SEQ ID No 22 SEQ ID NO 24 or the variant amino acid sequence, and a pharmaceutically acceptable carrier.

Further preferred embodiments of the invention comprise at least 3, 4, 5, 6, 7, 8, 9, 10, 11 12, 13, 14, 15, 16, 17 or 18 peptides containing an amino acid sequence selected from the group consisting of SEQ ID NO 1 to SEQ ID NO 10 and SEQ ID No 11 to SEQ ID No 22 SEQ ID NO 24 and/or an amino acid sequence that is at least 85% identical to that of SEQ ID NO 1 to SEQ ID NO 10 and/or a polynucleotide containing a nucleic acid encoding SEQ ID NO 1 to SEQ ID NO 10 and SEQ ID No 11 to SEQ ID No 22 SEQ ID NO 24 or the variant amino acid sequence, and a pharmaceutically acceptable carrier.

The pharmaceutical composition can furthermore contain additional peptides and/or excipients to be more effective, as will be further explained below.

By a "variant amino acid sequence" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence. For example, a peptide may be modified so that it at least maintains, if not improves, the ability to interact with and bind a suitable MHC molecule, such as HLA-A or -DR, and so that it at least maintains, if not improves, the ability to generate activated CTL which can recognise and kill cells which express a polypeptide containing an amino acid sequence as defined in the aspects of the invention. As can be derived from the database, certain positions of HLA-A binding peptides are typically anchor residues forming a core sequence fitting to the binding motif of the HLA binding groove.

Those amino acid residues that are not essential to interact with the T-cell receptor can be modified by replacement with another amino acid whose incorporation does not substantially affect T-cell reactivity and does not eliminate binding to the relevant MHC. Thus, apart from the proviso given, the peptide of the invention may be any peptide (by which term the inventors include oligopeptide or polypeptide) which includes the amino acid sequences or a portion or variant thereof as given.

It is furthermore known for MHC-class II presented peptides that these peptides are composed of a "core sequence" having a certain HLA-specific amino acid motif and, optionally, N- and/or C-terminal extensions that do not interfere with the function of the core sequence (i.e. are deemed as irrelevant for the interaction of the peptide and the T-cell). The N- and/or C-terminal extensions can, for example, be between 1 to 10 amino acids in length, respectively. These peptides can be used either directly to load MHC class II molecules or the sequence can be cloned into the vectors according to the description herein below. As these peptides form the final product of the processing of larger peptides within the cell, longer peptides can be used as well. The peptides of the invention may be of any size, but typically they may be less than 100,000 in molecular weight, preferably less than 50,000, more preferably less than 10,000, more preferably less than 5,000, more preferably less than 2,500 and typically about 1000 to 2000. In terms of the number of amino acid residues, the peptides of the invention may have fewer than 1000 residues, preferably fewer than 500 residues, more preferably fewer than 100 residues. Accordingly the present invention also provides compositions of peptides and variants thereof wherein the peptide or variant has an overall length of between 8 and 100, preferably between 8 and 30, and most preferred between 8 and 17, namely 8, 9, 10, 11, 12, 13, 14, 15 or 16 amino acids.

Preferred are peptides have a core sequence selected from a group consisting of SEQ ID NO 11 to SEQ ID No 22 and SEQ ID NO 24 with extensions of 1 to 10 amino acids on the C-terminal and/or the N-terminal, more preferred the overall number of these flanking amino acids is 1 to 12, more preferred 1 to 10, more preferred 1 to 8, more preferred 1 to 6, wherein the flanking amino acids can be distributed in any ratio to the C-terminus and the N-terminus (for example all flanking amino acids can be added to one terminus, or the amino acids can be added equally to both termini or in any other ratio), provided that the peptide is still able to bind to an HLA molecule in the same way as said peptide according to any of the SEQ ID NO 11 to SEQ ID No 22 and SEQ ID NO 24.

Correspondingly, variants that induce T-cells cross-reacting with a peptide of the invention are often length variants.

If a peptide is longer than around 12 amino acid residues it is used directly to bind to a MHC class II molecule. It is preferred that the residues that flank the core HLA binding region do not substantially affect the ability of the peptide to bind specifically to the binding groove of the MHC class II molecule or to present the peptide to the CTL. However, as already indicated above, it will be appreciated that larger peptides may be used, especially when encoded by a polynucleotide, since these larger peptides may be fragmented by suitable antigen-presenting cells. Furthermore the flanking amino acids can reduce the speed of peptide degradation in vivo so that the amount of the actual peptide available to the CTLs is higher compared to the peptide without flanking amino acids.

It is also possible, that MHC class I epitopes, although usually between 8-10 amino acids long, are generated by peptide processing from longer peptides or proteins that include the actual epitope. Similar to MHC class II epitopes, it is preferred that the flanking residues of elongated precursor peptides upstream and/or downstream of the N- and C-terminus, of the actual epitope do not substantially affect the presentation of the peptide to the CTL nor mask the sites for proteolytic cleavage necessary to yield the actual epitope mediated by processing of the elongated peptide.

Preferred are peptides with a core sequence consisting of SEQ ID NO 1 to SEQ ID NO 10 and SEQ ID 11 with extensions of 1 to 10 amino acids on the C-terminal and/or the N-terminal, more preferred the overall number of these flanking amino acids is 1 to 12, more preferred 1 to 10, more preferred 1 to 8, more preferred 1 to 6, wherein the flanking amino acids can be distributed in any ratio to the C-terminus and the N-terminus (for example all flanking amino acids can be added to one terminus, or the amino acids can be added equally to both termini or in any other ratio), provided that the peptide is still able to bind to an HLA molecule in the same way as said peptide according to any of the of SEQ ID NO 1 to SEQ ID NO 10 and SEQ ID No 11.

Accordingly the present invention also provides peptides and variants of MHC class I epitopes having an overall length of between 8 and 100, preferably between 8 and 30, and most preferred between 8 and 18 namely 8, 9, 1.0, 11, 12, 13, 14, 15, 16 or 17 amino acids.

Of course, the peptide or variant according to the present invention will have the ability to bind to a molecule of the human MHC class I or II. Binding of a peptide or a variant to a MHC complex may be tested by methods known in the art, for example those described in the examples of the present invention below or those described in the literature for different MHC class II alleles (e.g. Vogt A B, Kropshofer Kalbacher H, Kalbus M, Rammensee H G, Coligan J E, Martin R; Ligand motifs of HLA-DRB5*0101 and DRB1*1501 molecules delineated from self-peptides; J Immunol. 1994; 153(4):1665-1673; Malcherek G, Gnau V, Stevanovic S. Rammensee H G, Jung G, Melms A; Analysis of allele-specific contact sites of natural HLA-DR17 ligands; J Immunol, 1994; 153(3):1141-1149; Manici S, Sturniolo T, Imro M A, Hammer J, Sinigaglia F, Noppen C, Spagnoli G, Mazzi B, Bellone M, Dellabona P, Protti M P; Melanoma cells present a MAGE-3 epitope to CD4(+) cytotoxic T cells in association with histocompatibility leukocyte antigen DR11; J Exp Med. 1999; 189(5): 871-876; Hammer J, Gallazzi F, Bono B, Karr R W, Guenot J, Valsasnini P, Nagy Z A, Sinigaglia F; Peptide binding specificity of HLA-DR4 molecules: correlation with rheumatoid arthritis association; J Exp Med. 1995 181(5):1847-1855; Tompkins S M, Rota P A, Moore J C, Jensen P E; A europium fluoroimmunoassay for measuring binding of antigen to class II MHC glycoproteins; J Immunol Methods. 1993; 163(2): 209-21.6; Boynton R J, Lohmann T, Londei M, Kalbacher H, Halder T, Frater A J, Douek D C, Leslie D G, Flavell R A, Altmann D M; Glutamic acid decarboxylase T lymphocyte responses associated with susceptibility or resistance to type I diabetes: analysis in disease discordant human twins, non-obese diabetic mice and HLA-DQ transgenic mice; Int Immunol. 1998 (12):1765-1776).

Peptides of the present invention may have additional N- and/or C-terminally located stretches of amino acids that do not necessarily form part of the peptide that functions as the actual epitope for MHC molecules but may, nevertheless, be important to provide for an efficient introduction of the peptide according to the present invention into the cells (see above). In one embodiment of the present invention, the peptide of the present invention is a fusion protein which comprises, for example, the 80 N-terminal amino acids of the HLA-DR antigen-associated invariant chain (p33, in the following "Ii") as derived from the NCBI, GenBank Accession-number X00497 (Strubin, M., Mach, B. and Long, E. O. The complete sequence of the mRNA for the HLA-DR-associated invariant chain reveals a polypeptide with an unusual transmembrane polarity EMBO J. 3 (4), 869-872 (1984)).

The present invention also provides a pharmaceutical composition comprising at least one of the peptides of the present invention, wherein the peptides have an overall length of between 8 and 100, preferably between 8 and 30, and most preferred between 8 and 17 or 9, 10, 11, 12, 13, 14, 15, or 16 amino acids.

In addition, the peptide or variant may be modified further to improve stability and/or binding to MHC molecules to elicit a stronger immune response. Methods for such an optimisation of a peptide sequence are well known in the art and include, for example, the introduction of reverse peptide bonds or non-peptide bonds.

Thus, according to another aspect the invention provides a pharmaceutical composition, wherein at least one peptide or variant includes non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) J. Immunol. 159, 3230-3237, incorporated herein by reference. This approach involves making pseudopeptides containing changes involving the backbone, and not the orientation of side chains. Meziere et al (1997) show that for MHC and T helper cell responses, these pseudopeptides are useful. Retro-inverse peptides, containing NH—CO bonds instead of CO—NH peptide bonds, are much more resistant to proteolysis.

A non-peptide bond is, for example, —CH$_2$—NH, —CH$_2$S—, —CH$_2$CH$_2$—, —CH═CH—, —COCH$_2$—, —CH(OH)CH$_2$—, and —CH$_2$SO—, U.S. Pat. No. 4,897,445 provides a method for the solid phase synthesis of non-peptide bonds (—CH$_2$—NH) in polypeptide chains that involves polypeptides synthesized by standard procedures and the non-peptide bond synthesized by reacting an amino aldehyde and an amino acid in the presence of NaCNBH$_3$.

Peptides comprising the sequences of the invention described above may be synthesized with additional chemical groups present at their amino and/or carboxy termini, to enhance, for example, the stability, bioavailability, and/or affinity of the peptides. For example, hydrophobic groups such as carbobenzoxyl, dansyl, or t-butyloxycarbonyl groups may be added to the peptides amino termini. Likewise, an acetyl group or a 9-fluorenylmethoxy-carbonyl group may be placed at the peptides' amino termini. Additionally, e.g. the hydrophobic group, t-butyloxycarbonyl, or an amido group may be added to the peptides' carboxy termini.

Further, all peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarised e.g. in R. Lindblad, Chemical Reagents for Protein Modification, 3rd ed. CRC Press, 2005, which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley & Sons NY 1995-2000) for more extensive methodology relating to chemical modification of proteins.

Successful modification of therapeutic proteins and peptides with PEG is often associated with an extension of circulatory half-life while cross-linking of proteins with glutaraldehyde, polyethyleneglycol diacrylate and formaldehyde is used for the preparation of hydrogels. Chemical modification of allergens for immunotherapy is often achieved by carbamylation with potassium cyanate.

Generally, peptides and variants (at least those containing peptide linkages between amino acid residues) may be synthesized e.g. using the Fmoc-polyamide mode of solid-phase peptide synthesis as disclosed by Lu et al (1981) J. Org. Chem. 46, 3433 and references therein.

Purification may be effected by any one, or a combination of, techniques such as recristallisation, size exclusion chromatography, ion-exchange chromatography, hydrophobic interaction chromatography and (usually) reverse-phase high performance liquid chromatography using e.g. acetonitril/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

A further aspect of the invention provides a nucleic acid (e.g. polynucleotide) encoding a peptide or variant of the invention. The polynucleotide may be e.g. DNA, cDNA, PNA, CNA, RNA, either single- and/or double-stranded, or native or stabilised forms of polynucleotides, such as e.g. polynucleotides with a phosphorothiate backbone, or combinations thereof and it may or may not contain introns so long as it codes for the peptide. Of course, it is only peptides containing naturally occurring amino acid residues joined by naturally occurring peptide bonds are encodable by a polynucleotide. A still further aspect of the invention provides an expression vector capable of expressing a polypeptide according to the invention. Expression vectors for different cell types are well known in the art and can be selected without undue experimentation.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Guidance can be found e.g. in Sambrook et al (1989) Molecular Cloning, A Laboratory Manual, Cold Spring Harbor Laboratory, Cold Spring Harbor, N.Y.

In a particularly preferred embodiment of the invention, however, the pharmaceutical composition comprises at least two peptides consisting of amino acid sequences according to SEQ ID NO 1 to SEQ ID NO 12.

The optimum amount of each peptide to be included in the vaccine and the optimum dosing regimen can be determined by one skilled in the art without undue experimentation. For example, the peptide or its variant may be prepared for intravenous (i.v.) injection, subcutaneous (s.c.) injection, intradermal (i.d.) injection, intraperitoneal (i.p.) injection, intramuscular (i.m.) injection. Preferred routes of peptide injection are s.c., i.d., i.p., i.m., and i.v. Preferred routes of DNA injection are i.d., i.m., s.c., i.p. and i.v. Doses of e.g. between 1 and 500 mg and 50 µg and 1.5 mg, preferably 125 µg to 500 µg, of peptide or DNA may be given and will depend from the respective peptide or DNA. Doses of this range were successfully used in previous trials (Brunsvig P F, Aamdal S, Gjertsen M K, Kvalheim G, Markowski-Grimsrud C J, Sve. I. Dvrhaug M, Trachsel S, Møller M, Eriksen J A, Gaudernack G; Telomerase peptide vaccination: a phase I/II study in patients with non-small cell lung cancer; Cancer Immunol Immunother. 2006; 55(12):1553-1561; M. Staehler, A. Steitzl, P. Y. Dietrich, T. Eisen, A. Haferkamp, J. Beck, A. Mayer, S. Walter, H. Singh, J. Frisch, C. G. Stief; An open label study to evaluate the safety and immunogenicity of the peptide based cancer vaccine IMA901, ASCO meeting 2007; Abstract No 3017).

Pharmaceutical compositions of the present invention may be compiled such that the selection, number and/or amount of peptides present in the composition is/are tissue, cancer, and/or patient-specific. For instance the exact selection of peptides can be guided by expression patterns of the parent proteins in a given tissue to avoid side effects. The selection may be dependent from the specific type of cancer that the patient to be treated is suffering from as well as the status of the disease, earlier treatment regimens, the immune status of the patient, and, of course, the HLA-haplotype of the patient. Furthermore, the vaccine according to the invention can contain individualised components, according to personal needs of the particular patient. Examples are different amounts of peptides according to the expression of the related TAAs in the particular patient, unwanted side-effects due to personal allergies or other treatments, and adjustments for secondary treatments following a first round or scheme of treatment.

For compositions to be used as a vaccine for GBM for example, peptides whose parent proteins are expressed in high amounts in normal tissues will be avoided or be present in low amounts in the composition of the invention. On the other hand, if it is known that the tumor of a patient expresses high amounts of a certain protein the respective pharmaceutical composition for treatment of this cancer may be present in high amounts and/or more than one peptide specific for this particular protein or pathway of this protein may be included. The person of skill will be able to select preferred combinations of immunogenic peptides by testing, for example, the generation of T-cells in vitro as well as their efficiency and overall presence, the proliferation, affinity and expansion of certain T-cells for certain peptides, and the functionality of the T-cells, e.g. by analysing the IFN-gamma production (see also examples below). Usually, the most efficient peptides are then combined as a vaccine for the purposes as described above.

A suitable vaccine will preferably contain between 1 and 20 peptides, more preferably 2, 3, 4, 5, 6, 7, 8, 9, 10, 11, 12, 13, 14, 15, 16, 17, 18, 19, or 20 different peptides, further preferred 6, 7, 8, 9, 10 11, 12, 13, or 14 different peptides, and most preferably 10, 11, 12, 13 or 14 different peptides. The length of the peptide for use in a cancer vaccine may be any suitable length, as disclosed herein. In particular, it may be a suitable 9-mer peptide or a suitable 8-met or 9-mer or 10-mer or 11-mer peptide or 12-mer, 13-mer, 14-mer or 15-mer. Longer peptides may also be suitable, 9-mer or 10-mer peptides as described in the attached Tables 4 and 5 are preferred for MHC class I-peptides, while 12- to 15-mers are preferred for MHC class II peptides.

The peptide(s) constitute(s) a tumor or cancer vaccine. It may be administered directly into the patient, into the affected organ or systemically, or applied ex vivo to cells derived from the patient or a human cell line which are subsequently administered to the patient, or used in vitro to select a subpopulation from immune cells derived from the patient, which are then re-administered to the patient.

The peptide may be substantially pure, or combined with an immune-stimulating adjuvant (see below) or used in combination with immune-stimulatory cytokines, or may be administered with a suitable delivery system, for example liposomes. The peptide may also be conjugated to a suitable carrier such as keyhole limpet haemocyanin (KLH) or mannan (see WO 95/18145 and Longenecker et al (1993) Ann. NY Acad. Sci. 690, 276-291). The peptide may also be tagged, or be a fusion protein, or be a hybrid molecule. The peptides whose sequence is given in the present invention are expected to stimulate CD4 T cells or CD8 CTL. However, stimulation is more efficient in the presence of help provided by T-cells positive for the opposite CD. Thus, for MHC Class II epitopes that stimulate CD4 T cells the fusion partner or sections of a hybrid molecule suitably provide epitopes which stimulate CD8-positive T-cells. On the other hand, for MHC Class I epitopes which stimulate CD8 CTL the fusion partner or sections of a hybrid molecule suitably provide epitopes which stimulate CD4-positive T cells. CD4- and CD8-stimulating epitopes are well known in the art and include those identified in the present invention.

Pharmaceutically acceptable carriers are well known and are usually liquids, in which an active therapeutic agent is formulated. The carrier generally does not provide any pharmacological activity to the formulation, though it may provide chemical and/or biological stability, release characteristics, and the like. Exemplary formulations can be found, for example, in Alfonso R. Gennaro. Remington: The Science and Practice of Pharmacy, 20th Edition. Baltimore, Md.: Lippincott Williams & Wilkins, 2000 and include, but are not limited to, saline, water, buffered water, 0.3% glycine, hyaluronic acid, dextrose and the like. Recently, it was found that certain fat emulsions, which have been in use for many years for intravenous nutrition of human patients, can also act as a vehicle for peptides. Two examples of such emulsions are the available commercial fat emulsions known as Intralipid and Lipofundin. "Intralipid" is a registered trademark of Kabi Pharmacia, Sweden, for a fat emulsion for intravenous nutrition, described in U.S. Pat. No. 3,169,094. "Lipofundin" is a registered trademark of B. Braun Melsungen, Germany. Both contain soybean oil as fat (100 or 200 g in 1,000 ml distilled water: 10% or 20%, respectively). Egg-yolk phospholipids are used as emulsifiers in Intralipid (12 g/l distilled water) and egg-yolk lecithin in Lipofundin (12 g/l distilled water). Isotonicity results from the addition of glycerol (25 g/l) both in Intralipid and Lipofundin.

To elicit an immune response it is usually necessary to include adjuvants that render the composition more immunogenic. Thus in a preferred embodiment of the invention the pharmaceutical composition further comprises at least one suitable adjuvant.

Suitable adjuvants include, but are not limited to, 1018 ISS, aluminium salts, Amplivax®, AS15, BCG, CP-870, 893, CpG7909, CyaA, dSLIM, flagellin or TLR5 ligands derived from flagellin, FLT3 ligand, GM-CSF, IC30, IC31, Imiquimod (ALDARA®), resiquimod, ImuFact IMP321, Interleukins as IL-2, IL-13, IL-21, Interferon-alpha or -beta, or pegylated derivatives thereof, IS Patch, ISS, ISCOMATRIX, ISCOMs, JuvImmune, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactid co-glycolid) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Aucouturier et al., 2001; Allison and Krummel, 1995). Also cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich et al., 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of $T_{H1}$ cells and strong cytotoxic T-lymphocyte (CTL) generation, even in the absence of CD4 T cell help. The $T_{H1}$ bias induced by TLR9 stimulation is maintained even in the presence of vaccine adjuvants such as alum or incomplete Freund's adjuvant (IFA) that normally promote a $T_{H2}$ bias.

CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs CpR, Idera), dsRNA analogues such as poly(I:C) and derivates thereof (e.g. AmpliGen®, Hiltonol®, poly-(ICLC), poly(IC-R), poly(I:C12U), non-CpG bacterial DNA or RNA as well as immunoactive small molecules and antibodies such as cyclophosphamide, sunitinib, Bevacizumab, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g. anti-CD40, anti-TGFbeta, anti-TNFalpha receptor) and SC58175, which may act therapeutically and/or as an adjuvant. The amounts and concentrations of adjuvants and additives useful in the context of the present invention can readily be determined by the skilled artisan without undue experimentation.

Preferred adjuvants are imiquimod, resiquimod, GM-CSF, cyclophosphamide, sunitinib, bevacizumab, interferon-alpha, CpG oligonucleotides and derivates, poly-(I:C) and derivates, RNA, sildenafil, and particulate formulations with PLG or virosomes.

In a preferred embodiment the pharmaceutical composition according to the invention the adjuvant is selected from the group consisting of colony-stimulating factors, such as Granulocyte Macrophage Colony Stimulating Factor (GM-CSF, sargramostim), imiquimod, resiquimod, and interferon-alpha.

In a preferred embodiment of the pharmaceutical composition according to the invention, the adjuvant is imiquimod or resiquimod.

In a preferred embodiment of the pharmaceutical composition according to the invention, the adjuvant is imiquimod or resimiquimod.

In a preferred embodiment of the pharmaceutical composition according to the invention, the adjuvant is the combination of GM-CSF and imiquimod.

Compositions of the present invention may be used for parenteral administration, such as subcutaneous, intradermal, intramuscular, intraperitoneal or for oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavours, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients, $3^{rd}$ Ed. 2000, American Pharmaceutical Association and pharmaceutical press. The composition can be used for a prevention, prophylaxis and/or therapy of adenomateous or cancerous diseases, preferably CRC.

Preferred formulations can be found, for example, in EP2113253.

Cytotoxic T-cells (CTLs) recognise an antigen in the form of a peptide bound to an MHC molecule rather than the intact foreign antigen itself. The MHC molecule itself is located at the cell surface of an antigen presenting cell. Thus, an activation of CTLs is only possible if a trimeric complex of peptide antigen, MHC molecule, and APC is present. Correspondingly, it may enhance the immune response if not only the peptide is used for activation of CTLs but if additionally APCs with the respective MHC molecule are added.

Therefore, in a preferred embodiment the pharmaceutical composition according to the present invention additionally contains at least one antigen-presenting cell.

The antigen-presenting cell (or stimulator cell) typically has an MHC class I or II molecule on its surface and in one embodiment is substantially incapable of loading itself the MHC class I or II molecule with the selected antigen. As it is described in more detail below, the MHC class I or II molecule may readily be loaded with the selected antigen in vitro.

Preferably the mammalian cell lacks or has a reduced level or has reduced function of the TAP peptide transporter. Suitable cells which lack the TAP peptide transporter include T2, a human peptide loading deficient cell line that is available from the American Type Culture Collection, 12301 Parklawn Drive, Rockville, Md. 20852, USA under Catalogue No CRL 1992; TAP-deficient cell lines such as T2 can be used as APCs, and due to the lack of TAP nearly all peptides presented by MHC class I will be the peptides under scrutiny used for externally loading the empty MHC class I molecules of these cell lines, hence all effects will clearly attribute to the used peptides.

Preferably, the antigen presenting cells are dendritic cells. Suitably, the dendritic cells are autologous dendritic cells which are pulsed with an antigenic peptide. The antigenic peptide may be any suitable antigenic peptide which gives rise to an appropriate T-cell response. T-cell therapy using autologous dendritic cells pulsed with peptides from a tumor associated antigen is disclosed, in Murphy et al (1996) The Prostate 29, 371-380, and Tjua et al (1997) The Prostate 32, 272-278.

Thus, in a preferred embodiment of the present invention the pharmaceutical composition containing at least one antigen presenting cell is pulsed or loaded with the peptide, for instance by the method shown in example 5.

As an alternative the antigen presenting cell comprises an expression construct encoding the peptide. The polynucleotide may be any suitable polynucleotide and it is preferred that it is capable of transducing the dendritic cell thus resulting in the presentation of a peptide and induction of immunity.

Conveniently, a nucleic acid of the invention may be comprised in a viral polynucleotide or virus. For example, adenovirus-transduced dendritic cells have been shown to induce antigen-specific antitumor immunity in relation to MUC1 (see Gong et al (1997) Gene Ther. 4, 1023-1028). Similarly, adenovirus-based systems may be used (see, for example, Wan et al (1997) Hum. Gene Ther. 8, 1355-1363); retroviral systems may be used (Koch et al., 2006) J. Exp. Med. 186, 1213-1221 and Szaboles et al (1997) Blood particle-mediated transfer to dendritic cells may also be used {Tuting 1997}Eur. J. Immunol, 27, 2702-2707); and RNA may also be used (Ashley et al., 2007) J. Exp, Med. 186, 1177 1182).

Generally, a pharmaceutical composition of the invention containing (a) nucleic acid(s) of the invention can be administered in a similar manner as those containing peptide(s) of the invention, e.g. intravenously, intra-arterially, intra-peritoneally, intramuscularly, intradermally, intratumorally, orally, nasally, buccally, rectally, vaginally, by inhalation, or by topical administration.

Due to evasion mechanisms a tumor often develops resistance to the treatment. The drug resistance may occur during treatment and manifests itself in metastases and recurring tumors. To avoid such a drug resistance a tumor is commonly treated by a combination of drugs and metastases and tumors recurring after a disease free period of time often require a different combination. Therefore, in one aspect of the invention the pharmaceutical composition is administered in conjunction with a second anticancer agent. The second agent may be administered before after or simultaneously with the pharmaceutical composition of the invention. A simultaneous administration can e.g. be achieved by mixing the pharmaceutical composition of the invention with the second anticancer agent if chemical properties are compatible. Another way of a simultaneous administration is the administration of the composition and anticancer agent on the same day independently from the route of administration such that the pharmaceutical composition of the invention may be e.g. injected while the second anticancer agent is for instance given orally. The pharmaceutical composition and second anticancer agent may also be administered within the same treatment course but on different days and/or within separate treatment courses.

In another aspect the present invention provides a method for treating or preventing a cancer in a patient comprising administering to the patient a therapeutically effective amount any one of the pharmaceutical compositions of the invention.

A therapeutically effective amount will be an amount sufficient to induce an immune response, in particular an activation of a subpopulation of CTLs. A person skilled in the art may easily determine whether an amount is effective by using standard immunological methods, such as those provided in the examples of the present specifications. Another way of monitoring the effect of a certain amount of the pharmaceutical composition is to observe the growth of the tumor treated and/or its recurrence.

In a particularly preferred embodiment of the present invention the pharmaceutical composition is used as an anti-cancer vaccine.

The composition containing peptides or peptide-encoding nucleic acids can also constitute a tumor or cancer vaccine. It may be administered directly into the patient, into the affected organ or systemically, or applied ex vivo to cells derived from the patient or a human cell line which are subsequently administered to the patient, or used in vitro to select a subpopulation from immune cells derived from the patient, which are then re-administered to the patient.

The composition of the invention may be used in a method for treating of or used as a vaccine for cancer. The cancer may be prostate carcinoma, oral cavity carcinomas, oral squamous carcinoma (OSCC) acute myeloid leukemia (AML) (Qian et al., 2009), H. pylori-induced MALT lymphoma (Banerjee et al., 2000), colon carcinoma/colorectal cancer, glioblastoma, non-small-cell lung cancer (NSCLC), cervical carcinoma, human breast cancer, prostate cancer, colon cancer, pancreatic cancers, pancreatic ductal adenocarcinoma, ovarian cancer, hepatocellular carcinoma, liver cancer, brain tumors of different phenotypes, leukemias such as acute lymphoblastic leukemia, ALL, lung cancer, Ewing's sarcoma, endometrial cancer, head and neck squamous cell carcinoma, epithelial cancer of the larynx, oesophageal carcinoma, oral carcinoma, carcinoma of the urinary bladder, ovarian carcinomas, renal cell carcinoma, atypical meningioma, papillary thyroid carcinoma, brain tumors, salivary duct carcinoma, extranodal T/NK-cell lymphomas, Non-Hodgkins Lymphoma and malignant solid tumors of the lung and breast, preferably the cancer is gastric cancer.

In the most preferred embodiment of the method of treatment or vaccine according to the invention, the vaccine is a multiple peptide tumor vaccine for treatment of GC. Preferably, the vaccine comprises a set of tumor-associated peptides selected from SEQ ID No. 1 to SEQ ID No. 11 which are located and have been identified on primary GC cells. This set includes HLA class I and class II peptides. The peptide set can also contain at least one peptide, such as from HBV core antigen (SEQ ID 23), used as a positive control peptide serving as immune marker to test the efficiency of the intradermal administration. In one particular embodiment, the vaccine consists of 11 individual peptides (according to SEQ ID No. 1 to SEQ ID No. 11) with between about 1500 µg to about 75 µg, preferably between about 1000 µg to about 175 µg and more preferred between about 500 µg to about 600 µg, and most preferred about 578 µg of each peptide, all of which may be purified by HPLC and ion exchange chromatography and appear as a white to off-white powder. The lyophilisate is preferably dissolved in sodium hydrogen carbonate, and is used for intradermal injection within 30 min after reconstitution at room temperature. According to the present invention, preferred amounts of peptides can vary between about 0.1 and 100 mg, preferably between about 0.1 and 1 mg, and most preferred between about 300 µg and 800 µg per 500 µl of solution. Herein, the term "about" shall mean+/−10 percent of the given value, if not stated differently. The person of skill will be able to adjust the actual amount of peptide to be used based on several factors, such as, for example, the immune status of the individual patient and/or the amount of TUMAP that is presented in a particular type of cancer. The peptides of the present invention might be provided in other suitable forms (sterile solutions, etc.) instead of a lyophilisate.

The pharmaceutical compositions comprise the peptides either in the free form or in the form of a pharmaceutically acceptable salt.

As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH2 group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, hydrochloric acid, hydrobromic acid, sulfuric acid, nitric acid phosphoric acid and the like. Conversely, basic salts of acid moieties which may be present on a peptide are prepared using a pharmaceutically acceptable base such as sodium hydroxide, potassium hydroxide, ammonium hydroxide, calcium hydroxide, trimethylamine or the like.

In an especially preferred embodiment the pharmaceutical compositions comprise the peptides as salts of acetic acid (acetates), ammonium or hydrochloric acid (chlorides).

In another embodiment, a pharmaceutical composition of the present invention may include sugars, sugar alcohols, aminoacids such a glycin, arginine, glutaminic acid and others as framework former. The sugars may be mono-, di- or trisaccharide. These sugars may be used alone, as well as in combination with sugar alcohols. Examples of sugars include glucose, mannose, galactose, fructose or sorbose as monosaccharides, saccharose, lactose, maltose or trehalose as disaccharides and raffinose as a trisaccharid. A sugar alcohol may be, for example, mannitose. Preferred ingredients are saccharose, lactose, maltose, trehalose, mannit and/or sorbit, and snore preferably, mannitol.

Furthermore pharmaceutical compositions of the present invention may include physiological well tolerated excipients (see Handbook of Pharmaceutical Excipients, $5^{th}$ ed., edited by Raymond Rowe, Paul Sheskey and Sian Owen, Pharmaceutical Press (2006)), such as antioxidants like ascorbic acid or glutathione, preserving agents such as phenole, m-cresole, methyl- or propylparabene, chlorobutanol, thiomersal or benzalkoniumchloride, stabilizer, framework former such as saccharose, lactose, maltose, trehalose, mannitose, mannit and/or sorbit, mannit and/or lactose and solubilizer such as polyethyleneglycols (PEG), i.e. PEG 3000, 3350, 4000 or 6000, or cyclodextrines, i.e. hydroxypropyle-ß-cyclodextrine, sulfobutylethyl-ß-cyclodextrine or γ cyclodextrine, or dextranes or poloxaomers, i.e. poloxaomer 407, poloxamer 188, or Tween 20, Tween 80. In a preferred embodiment pharmaceutical compositions of the present invention include one or more well tolerated excipients, selected from the group consisting of antioxidants, framework formers and stabilizers.

The acceptable pH-range is pH 2-12 intravenous and intramuscular administration, but subcutaneously the range is reduced to 2.7-9.0 as the rate of in vivo dilution is reduced resulting in more potential for irradiation at the injection site. Strickley Robert G., Pharm. Res., 21, NO:2, 201-230 (2004).

The pharmaceutical preparation of the present invention comprising peptides, and/or nucleic acid(s) according to the invention is administered to a patient that suffers from an adenomateous or cancerous disease that is associated with the respective peptide or antigen. By this, a T cell-mediated immune response can be triggered.

Preferred is a pharmaceutical composition according to the invention, wherein the amount of (in particular tumor associated) peptide(s), of nucleic acid(s) according to the invention or expression vector(s) according to the invention as present in the composition is/are tissue, cancer, and/or patient-specific.

In another embodiment of the invention the vaccine is a nucleic acid vaccine. It is known that inoculation with a nucleic acid vaccine, such as a DNA vaccine, encoding a polypeptide leads to a T-cell response. It may be administered directly into the patient, into the affected organ or systemically, or applied ex vivo to cells derived from the patient or a human cell line which are subsequently administered to the patient, or used in vitro to select a subpopulation from immune cells derived from the patient, which are then re-administered to the patient. If the nucleic acid is administered, to cells in vitro, it may be useful for the cells to be transfected so as to co-express immune-stimulating cytokines, such as interleukin-2 or GM-CSF. The nucleic acid(s) may be substantially pure, or combined with an immune-stimulating adjuvant, or used in combination with immune-stimulatory cytokines, or be administered with a suitable delivery system, for example liposomes. The nucleic acid vaccine may also be administered with an adjuvant such as those described for peptide vaccines above. It is preferred if the nucleic acid vaccine is administered without adjuvant.

The polynucleotide may be substantially pure, or contained in a suitable vector or delivery system. Suitable vectors and delivery systems include viral, such as systems based on adenovirus, vaccinia virus, retroviruses, herpes virus, adeno-associated virus or hybrids containing elements of more than one virus. Non-viral delivery systems include cationic lipids and cationic polymers as are well known in the art of DNA delivery. Physical delivery, such as via a 'gene-gun', may also be used. The peptide or peptide encoded by the nucleic acid may be a fusion protein, for example with an epitope from tetanus toxoid which stimulates CD4-positive T-cells.

Suitably, any nucleic acid administered to the patient is sterile and pyrogen free. Naked DNA may be given intramuscularly or intradermally or subcutaneously. Conveniently, the nucleic acid vaccine may comprise any suitable nucleic acid delivery means. The nucleic acid, preferably DNA, may also be delivered in a liposome or as part of a viral vector delivery system. It is preferred if the nucleic acid vaccine, such as DNA vaccine, is administered into the muscle, whilst peptide vaccines are preferably administered s.c. or i.d. It is also preferred if the vaccine is administered into the skin.

It is believed that uptake of the nucleic acid and expression of the encoded polypeptide by professional antigen presenting cells such as dendritic cells may be the mechanism of priming of the immune response; however, dendritic cells may not be transfected but are still important since they may pick up expressed peptide from transfected cells in the tissue ("cross-priming", Thomas A M, Santarsiero L M, Lutz E R, Armstrong T D, Chen Y C, Huang L Q, Lahera D A, Goggins M, Hrdban R H, Jaffee E M. Mesothelin-specific CD8(+) T cell responses provide evidence of in vivo cross-priming by antigen-presenting cells in vaccinated pancreatic cancer patients. J Exp Med. 2004 Aug. 2; 200(3):297-306).

Polynucleotide-mediated immunization therapy of cancer is described in Conry et al (1996) Seminars in Oncology 23, 135-147; Condon et al (1996) Nature Medicine 2, 1122-1127; Gong et al (1997) Nature Medicine 3, 558-561; Zhai et al (1996) J. Immunol, 156, 700-710; Graham et al (1996) et al J. Cancer 65, 664-670; and Burchell et al (1996) 309-313 in: Breast Cancer, Advances in biology and therapeutics, Calvo et al (Eds), John Libbey Eurotext, all of which are incorporated herein by reference in their entireties.

It may also be useful to target the vaccine to specific cell populations, for example antigen presenting cells, either by the site of injection, use of targeting vectors and delivery systems, or selective purification of such a cell population from the patient and ex vivo administration of the peptide or nucleic acid (for example dendritic cells may be sorted as described in Zhou et al (1995) Blood 86, 3295-3301; Roth et al (1996) Scand. J. Immunology 43, 646-651). For example, targeting vectors may comprise a tissue- or tumor-specific promoter which directs expression of the antigen at a suitable place.

Finally, the vaccine according to the invention can be dependent on the specific type of cancer that the patient to be treated is suffering from as well as the status of the disease, earlier treatment regimens, the immune status of the patient, and, of course, the HLA-haplotype of the patient. Furthermore, the vaccine according to the invention can contain individualised components, according to personal needs of the particular patient. Examples are different amounts of peptides according to the expression of the related TAAs in the particular patient, unwanted side-effects due to personal allergies or other treatments, and adjustments for secondary treatments following a first round or scheme of treatment.

In addition to being useful for treating cancer, the peptides of the present invention are also useful as diagnostics. Since the peptides were generated from glioblastoma and since it was determined that these peptides are not present in normal tissues, these peptides can be used to diagnose the presence of a cancer.

The presence of the peptides of the present invention on tissue biopsies can assist a pathologist in diagnosis of cancer. Detection of certain peptides of the present invention by means of antibodies, mass spectrometry or other methods known in the art can tell the pathologist that the tissue is malignant or inflamed or generally diseased. Presence of groups of peptides of the present invention can enable classification or subclassification of diseased tissues.

The detection of the peptides of the present invention on diseased tissue specimen can enable the decision about the benefit of therapies involving the immune system, especially if T lymphocytes are known or expected to be involved in the mechanism of action. Loss of MHC expression is a well described mechanism by which infected or malignant cells escape immunosurveillance. Thus, presence of the peptides of the present invention shows that this mechanism is not exploited by the analyzed cells.

The peptides of the present invention might be used to analyze lymphocyte responses against those peptides of the present invention, such as T cell responses or antibody responses against the peptides of the present invention or the peptides of the present invention complexed to MHC molecules. These lymphocyte responses can be used as prognostic markers for decision on further therapy steps. These responses can also be used as surrogate markers in immunotherapy approaches aiming to induce lymphocyte responses by different means, e.g. vaccination of protein, nucleic acids, autologous materials, adoptive transfer of lymphocytes. In gene therapy settings, lymphocyte responses against the peptides of the present invention can be considered in the assessment of side effects. Monitoring of lymphocyte responses might also be a valuable tool for follow-up examinations of transplantation therapies, e.g. for the detection of graft versus host and host versus graft diseases.

In yet another aspect thereof, the present invention relates to a kit comprising (a) a container that contains a pharmaceutical composition as described above, in solution or in lyophilized form; (b) optionally, a second container containing a diluent or reconstituting solution for the lyophilized formulation; and (c) optionally, instructions for (i) use of the solution or (ii) reconstitution and/or use of the lyophilized formulation. The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contain/s instructions on or associated with the container that indicate directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeated administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 µg) and preferably not more than 3 mg/mL/peptide (=1500 µg). The kit may further include other materials desirable from a commercial and user standpoint, including other buffers, diluents, fillers, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, a anti-angiogenesis agent or inhibitor, an apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The pharmaceutical formulation of the present invention is one that is suitable for administration of the peptides by any acceptable route such as oral (enteral), nasal, ophthal, subcutaneous, intradermal, intramuscular, intravenous or transdermal. Preferably the administration is s.c., and most preferably, i.d. Administration may be by infusion pump.

It should be understood that the features of the invention as disclosed and described herein can be used not only in the respective combination as indicated but also in a singular fashion without departing from the intended scope of the present invention. For the purposes of the present invention, all references as cited herein are incorporated by reference in their entireties.

The invention will now be described in more detail by reference to the following Figures, the Sequence listing, and the Examples. The following examples are provided for illustrative purposes only and are not intended to limit the invention.

FIG. 1: Tetramer analysis of microsphere driven proliferation of CDC2-001 and ASPM-002 specific CD8+ lymphocytes from peripheral blood of a healthy donor. $1\times10^6$ CD8+ enriched PBMCs per well were stimulated weekly with microspheres coupled to anti-CD28 plus high density tumor antigen A*2402/CDC2-001 (left panel) or anti-CD28 plus high density tumor antigen A*024/ASPM-002 (right panel). After three stimulations in vitro, all cells were stained with antibody CD8 FITC, and fluorescently-labeled tetramers A*2402/CDC2-001 and A*2402/ASPM-002-001. Cells are gated on CD8+ lymphocytes; numbers in the plots represent percentage of cells in the indicated quadrant among CD8+ lymphocytes (multimer-positive cells).

FIG. 2: Relative in vitro binding of IMA-BIR-002 and IMA-MET-005 derived 15-mers to the most frequent HLA-DR alleles. The ProImmune REVEAL™ technology employs in vitro HLA-DR assembly assays to determine the on-rates for the MHC:peptide complex as one major determinant of the binding constant of individual peptides. The assay was performed by ProImmune (Oxford, UK). At a fixed time point, the amount of intact MHC:peptide complexes is measured and compared with the amount for a pass/fail control (relative weak binder). A strong, promiscuous HLA-DR binder is included as positive control. Values indicate amount of binding for the individual peptides and HLA-DR molecules relative to the pass/fail control. As the REVEAL™ technology is limited to 15-mers, two overlapping 15-mers (position 2-16; 6-20) were tested instead of full-length MET-005.

FIGS. 3a and 3b depict the presence of PSMA and Survivin-specific IFNγ-secreting CD4+ T-cells in peripheral blood mononuclear cells (PBMC) from different time points of a vaccinated patient which were determined using an IFNγ-EliSpot. Time points: pre-vaccination (a) and after the fter $3^{rd}$ (b), $6^{th}$ (c), $7^{th}$ (d), $8^{th}$ (e), $9^{th}$ (f), $10^{th}$ (g), $11^{th}$(h) vaccination.

FIG. 4 shows the presence of Survivin-specific IFNγ-, IL-5, IF-10, TNFα-secreting CD4+ T-cells in PBMC from three different time points of a vaccinated patient which were determined via the Intracellular staining-Assay (ICS). Time points: after $1^{st}$ (a), $3^{rd}$ (b), $7^{th}$ (c) vaccination.

1. Synthesis

Peptides were synthesized by standard and well-established, solid phase peptide synthesis using the Fmoc-strategy. After purification by preparative RP-HPLC, ion-exchange procedure was performed to incorporate physiological compatible counter ions (for example acetate, ammonium or chloride). Finally, white to off-white solids were obtained after lyophilisation. All TUMAPs are preferably administered as acetate salts, other salt-forms are also possible.

Importantly, identity and purity of each individual peptide have been determined by mass spectrometry and analytical RP-HPLC. After ion-exchange procedure the peptides were obtained as white to off-white lyophilizates in purities shown in table 7:

TABLE 7

| SEQ ID NO. | PEPTIDE ID | PEPTIDE LENGTH (NO OF AMINO ACIDS) | SALT FORM | PURITY [REL. AREA %] |
| --- | --- | --- | --- | --- |
| 1 | ASPM-002 | 9 | ACETATE | 92.5 |
| 2 | BIR-002 | 15 | ACETATE | 96.3 |
| 3 | CDC2-001 | 10 | ACETATE | 94.8 |

TABLE 7-continued

| SEQ ID NO. | PEPTIDE ID | PEPTIDE LENGTH (NO OF AMINO ACIDS) | SALT FORM | PURITY [REL. AREA %] |
| --- | --- | --- | --- | --- |
| 4 | MET-006 | 9 | ACETATE | 96.0 |
| 5 | MMP11-001 | 10 | ACETATE | 96.1 |
| 6 | MST1R-001 | 9 | ACETATE | 96.3 |
| 7 | PPAP2C-001 | 9 | ACETATE | 94.4 |
| 8 | PROM1-001 | 9 | ACETATE | 97.1 |
| 9 | SMC4-001 | 9 | ACETATE | 90.7 |
| 10 | UCHL5-001 | 9 | ACETATE | 95.1 |
| 11 | UQCRB-001 | 10 | ACETATE | 97.3 |
| 12 | (HBV-001) | 10 | ACETATE | 99.5 |
| 20 | AVL9-001 | 9 | ACETATE | 98.6 |
| 24 | ERBB3-001 | 9 | ACETATE | 99.1 |

All peptide have been tested with respect to their stability at different physicochemical conditions such as different temperatures and ph-values.

2. Components of the Exemplary Pharmaceutical Composition IMA941

IMA941 is composed of a cocktail of synthetic tumor associated peptides (TUMAPs) of which the majority has been identified on primary colorectal cancer cells. The TUMAPs include 10 HLA class I-binding peptides with the capacity to activate cytotoxic T cells (CD8+ T cells), 1 HLA class II-binding peptide with the capacity to activate T helper cells (CD4+ T cells) T helper cells play a crucial role in assisting the function of cytotoxic T cells by releasing cytokines which enhance the killer function of CD8+ T cells and may also act directly against tumor cells (Knutson and Disis, 2005). In addition to these II TUMAPs IMA941 may contain one viral control peptide.

Samples from surgically removed malignant and normal tissue from GBM patients and blood from healthy donors were analyzed in a stepwise approach:

First, genome-wide mRNA expression analysis by microarrays was used to identify genes overexpressed in the malignant tissue compared with a range of normal organs and tissues. In a second step, HLA ligands from the malignant material were identified by mass spectrometry. Subsequently identified HLA ligands were compared to gene expression data. Peptides encoded by selectively expressed or overexpressed genes as detected in step 1 were considered suitable candidate TUMAPs for a multi-peptide vaccine.

Finally, peripheral CD8+ T cells of healthy individuals were tested for reactivity against the tumor-associated HLA ligands using several immunoassays (in vitro T-cell assays).

3. Presentation of Tumor Associated Peptides (TUMAPs) Contained in IMA941 on Tumor Samples.

Tissue Samples

Patients' tumor tissues were provided by Kyoto Prefectural University of Medicine (KPUM), Kyoto, Japan, and Osaka City University Graduate School of Medicine (OCU), Osaka, Japan. Written informed consents of all patients had been given before surgery. Tissues were shock-frozen in liquid nitrogen immediately after surgery and stored until isolation of TUMAPs at −80° C.

Isolation of HLA Peptides from Tissue Samples

HLA peptide pools from shock-frozen tissue samples were obtained by immune precipitation from solid tissues according to a slightly modified protocol (Falk et al., 1991) (Seeger et al., 1999) using the HLA-A, -B, -C-specific antibody W6/32, CNBr-activated sepharose, acid treatment, and ultrafiltration.

Detection of TUMAPs by ESI-Liquid Chromatography Mass Spectrometry (ESI-LCMS)

The HLA peptide pools as obtained were separated according to their hydrophobicity by reversed-phase chromatography (Acquity UPLC system, Waters) and the eluting peptides were analyzed in an LTQ-Orbitrap hybrid mass spectrometer (ThermoElectron) equipped with an ESI source. Peptide pools were loaded directly onto the analytical fused-silica micro-capillary column (75 µm i.d.×250 mm) packed with 1.7 µm C18 reversed-phase material (Waters) applying a flow rate of 400 nL per minute. Subsequently, the peptides were separated using a two-step 180 minute-binary gradient from 10% to 33% B at a flow rate of 300 aT, per minute. The gradient was composed of Solvent A (0.1% formic acid in water) and solvent B (0.1% formic acid in acetonitrile). A gold coated glass capillary (PicoTip, New Objective) was used for introduction into the nanoESI source. The LTQ-Orbitrap mass spectrometer was operated in the data-dependent mode using a TOP5 strategy. In brief, a scan cycle was initiated with a full scan of high mass accuracy in the orbitrap (R=30 000), which was followed by MS/MS scans also in the orbitrap (R=7500) on the 5 most abundant precursor ions with dynamic exclusion of previously selected ions. Tandem mass spectra were interpreted by SEQUEST and additional manual control. The identified peptide sequence was assured by comparison of the generated natural peptide fragmentation pattern with the fragmentation pattern of a synthetic sequence-identical reference peptide. FIG. 1 shows an exemplary spectrum obtained from tumor tissue for the MHC class I associated peptide CDC2-001 and its elution profile on the UPLC system.

Example 2

Expression Profiling of Genes Encoding the Peptides of the Invention

Not all peptides identified as being presented on the surface of tumor cells by MHC molecules are suitable for immunotherapy, because the majority of these peptides are derived from normal cellular proteins expressed by many cell types. Only few of these peptides are tumor-associated and likely able to induce T cells with a high specificity of recognition for the tumor from which they were derived. In order to identify such peptides and minimize the risk for autoimmunity induced by vaccination the inventors focused on those peptides that are derived from proteins that are over-expressed on tumor cells compared to the majority of normal tissues.

The ideal peptide will be derived from a protein that is unique to the tumor and not present in any other tissue. To identify peptides that are derived from genes with an expression profile similar to the ideal one the identified peptides were assigned to the proteins and genes, respectively, from which they were derived and expression profiles of these genes were generated.

RNA Sources and Preparation

Surgically removed tissue specimens were provided by two different clinical sites (see Example 1) after written informed consent had been obtained from each patient. Tumor tissue specimens were snap-frozen in liquid nitrogen immediately after surgery and later homogenized with mortar and pestle under liquid nitrogen. Total RNA was prepared from these samples using TRI Reagent (Ambion, Darmstadt, Germany) followed by a cleanup with RNeasy (QIAGEN, Hilden, Germany); both methods were performed according to the manufacturer's protocol.

Total RNA from healthy human tissues was obtained commercially (Ambion, Huntingdon, UK; Clontech, Heidelberg, Germany; Stratagene, Amsterdam, Netherlands; BioChain, Hayward, Calif., USA). The RNA front several individuals (between 2 and 123 individuals) was mixed such that RNA from each individual was equally weighted. Leukocytes were isolated from blood samples of 4 healthy volunteers.

Quality and quantity of all RNA samples were assessed on an Agilent 2100 Bioanalyzer (Agilent, Waldbronn, Germany) using the RNA 6000 Pico LabChip Kit (Agilent).

Microarray Experiments

Gene expression analysis of all tumor and normal tissue RNA samples was performed by Affymetrix Human Genome (HG) U133A or HG-U133 Plus 2.0 oligonucleotide microarrays (Affymetrix, Santa Clara, Calif., USA), All steps were carried out according to the Affymetrix manual. Briefly, double-stranded cDNA was synthesized from 5-8 µg of total RNA, using SuperScript RTII (Invitrogen) and the oligo-dT-T7 primer (MWG Biotech, Ebersberg, Germany) as described in the manual. In vitro transcription was performed with the BioArray High Yield. RNA Transcript Labelling Kit (ENZO Diagnostics, inc., Farmingdale, N.Y., USA) for the U133A arrays or with the GeneChip IVT Labelling Kit (Affymetrix) for the U133 Plus 2.0 arrays, followed by cRNA fragmentation, hybridization, and staining with streptavidin-phycoerythrin and biotinylated anti-streptavidin antibody (Molecular Probes, Leiden, Netherlands). Images were scanned with the Agilent 2500A GeneArray Scanner (U133A) or the Affymetrix Gene-Chip Scanner 3000 (U133 Plus 2.0), and data were analyzed with the GCOS software (Affymetrix), using default settings for all parameters. For normalisation, 100 housekeeping genes provided by Affymetrix were used. Relative expression values were calculated from the signal log ratios given by the software and the normal kidney sample was arbitrarily set to 1.0.

The expression profiles of source genes of the present invention that are highly over-expressed in gastric cancer are shown in FIG. 2.

4. In Vitro Immunogenicity for IMA941 MHC Class I Presented Peptides

To obtain information regarding the immunogenicity of the TUMAPs of the present invention, investigations were performed using a well established in vitro stimulation platform already described by (Walter, S, Herrgen, L, Schoor, O, Jung, G, Wernet, D, Buhring, H J, Rammensee, H G, and Stevanovic, S; 2003, Cutting edge: predetermined avidity of human CD8 T cells expanded on calibrated MHC/anti-CD28-coated microspheres, J. Immunol., 171, 4974-4978). Using this platform, immunogenicity could be shown for the 10 HLA-A*2402 restricted TUMAPs of the invention, thus demonstrating that these peptides are T-cell eptiopes against which CD8+ precursor T cells exist in humans (Table 6).

In Vitro Priming of CD8+ T Cells

In order to perform in vitro stimulations by artificial antigen presenting cells (aAPC) loaded with peptide-MHC complex (pMHC) and anti-CD28 antibody, we first isolated CD8 T cells from fresh HLA-A*24 leukapheresis products of healthy donors obtained from the Blood Bank Tuebingen.

CD8 T cells were either directly enriched from the leukapheresis product or PBMCs (peripheral blood mononuclear cells) were isolated first by using standard gradient separation medium (PAA, Cölbe, Germany), Isolated CD8 lymphocytes or PBMCs were incubated until use in T-cell medium (TCM) consisting of RPMI-Glutamax (invitrogen, Karlsruhe, Germany) supplemented with 10% heat inactivated human AB serum (PAN-Biotech, Aidenbach, Germany), 100 U/ml Penicillin/100 µg/ml Streptomycin (Cambrex, Cologne, Germany), 1 mM sodium pyruvate (CC Pro, Oherdorla, Germany), 20 µg/ml Gentamycin (Cambrex), 2.5 ng/ml IL-7 (PromoCell, Heidelberg, Germany) and 10 U/ml IL-2 (Novartis Pharma, Nürnberg, Germany) were also added to the TCM at this step. Isolation of CD8+ lymphocytes was performed by positive selection using CD8 MicroBeads (Miltenyi Biotec, Bergisch-Gladbach, Germany).

Generation of pMHC/anti-CD28 coated beads, T-cell stimulations and readout was performed as described before (Walter et al., 2003) with minor modifications. Briefly, biotinylated peptide-loaded recombinant HLA-A *2402 molecules lacking the transmembrane domain and biotinylated at the carboxy terminus of the heavy chain were produced. The purified costimulatory mouse IgG2a anti human CD28 Ab 9.3 (Jung et al., 1987) was chemically biotinylated using Sulfo-N-hydroxysuccinimidobiotin as recommended by the manufacturer (Perbio, Bonn, Germany). Beads used were 5.6 µm large streptavidin coated polystyrene particles (Bangs Laboratories, Illinois, USA). pMHC used as controls were A *0201/MLA-001 (peptide ELAGIGILTV (SEQ ID NO: 25) from modified Melan-A/MART-1) and A*0201/DDX5-001 (YLLPAIVHI (SEQ ID NO: 26) from DDX5), respectively.

800.000 beads/200 µl were coated in 96-well plates in the presence of 600 ng biotin anti-CD28 plus 200 ng relevant biotin-0414C (high density beads). Stimulations were initiated in 96-well plates by co-incubating 1×10$^6$ CD8+ T cells with 2×10$^5$ washed coated beads in 200 µl TCM supplemented with 5 ng/ml IL-12 (PromoCell) for 3-4 days at 37° C. Half of the medium was then exchanged by fresh TCM supplemented with 80 U/ml IL-2 and incubating was continued for 3-4 days at 37° C. This stimulation cycle was performed for a total of three times. Finally, multimeric analyses were performed by staining the cells with Live/dead-Aqua dye (Invitrogen, Karlsruhe, Germany), CD8-FITC antibody clone SK1 (BD, Heidelberg, Germany) and PE- or APC-coupled A *2402 MHC multimers. For analysis, a BD LSRII SORP cytometer equipped with appropriate lasers and filters was used. Peptide specific cells were calculated as percentage of total CD8+ cells. Evaluation of multimeric analysis was done using the FLOWJO software (Tree Star, Oregon, USA). In vitro priming of specific multimer+ CD8+ lymphocytes was detected by appropriate gating and by comparing to negative control stimulations. Immunogenicity for a given antigen was detected if at least one evaluable in vitro stimulated well of one healthy donor was found to contain a specific CD8+ T-cell line after in vitro stimulation (i.e. this well contained at least 1% of specific multimer+ among CD8+ T-cells and the percentage of specific multimer+ cells was at least 10× the median of the negative control stimulations).

In Vitro Immunogenicity for IMA941 Peptides

For tested HLA class I peptides, in vitro immunogenicity could be demonstrated for all 14 peptides by generation of peptide specific T-cell lines. Exemplary flow cytometry results after TUMAP-specific multimer staining for two peptides of the invention are shown in FIG. 3, together with a corresponding negative control. Results for the peptides from the invention are summarized in Table 8, which provides in vitro immunogenicity of HLA class I peptides of the invention. The results of in vitro immunogenicity experiments show the percentage of positive tested donors and wells among evaluable peptides. At least two donors and 24 wells were evaluable for each peptide.

TABLE 8

In vitro immunogenicity of HLA class I peptides of the invention

| Antigen | Positive donors/ donors tested [%] | Positive wells/ wells tested [%] | SEQ ID No |
|---|---|---|---|
| CDC2-001 | 88 | 28 | 1 |
| ASPM-002 | 63 | 31 | 2 |
| MET-006 | 63 | 22 | 4 |
| UCHL5-001 | 75 | 14 | 3 |
| MST1R-001 | 50 | 14 | 7 |
| SMC4-001 | 75 | 9 | 9 |
| PROM1-001 | 83 | 26 | 5 |
| MMP11-001 | 33 | 11 | 10 |
| ABL1-001 | 50 | 13 | 21 |
| AVL9-001 | 100 | 50 | 20 |
| NUF2-002 | 50 | 4 | 22 |
| NUF2-001 | 100 | 25 | 19 |
| PPAP2C-001 | 100 | 54 | 8 |
| UQCRB-001 | 100 | 38 | 6 |
| ERBB3-001 | 83 | 15 | 24 |

5. Immunogenicity of IMA941 class II TUMAP BIR-002

A clinical study was conducted in order to confirm the immunogenicity of the peptide with the SEQ NO:11.

The primary study objective was the investigation of the PSA (prostate-specific antigen)-based response (PSA-R) to the subcutaneous administration of a prostate-specific peptide panel (vaccination therapy) in patients with biochemical relapse after radical prostatectomy without detection of manifest metastatic lesions.

The secondary study objective was the investigation of the tolerability and feasibility of administering vaccination therapy in patients with prostate carcinoma with special consideration of immunological phenomena in terms of a T cell response.

The study was designed as a prospective, randomized Phase I/II study for the indication of "biochemical relapse after radical prostatectomy without detection of manifest metastatic lesions."

Study Population

As part of this Phase I/II study, an attempt was made to induce PSA regression as an indicator of cessation of tumor growth by means of vaccination with a prostate-specific peptide panel in HLA-A*02$^+$ patients with biochemical relapse after radical prostatectomy. A combination of prostate-specific peptides was administered subcutaneously with evaluation of the extent of the respective immune response in the context of various administration forms of the antigenic structures.

In contrast to previous vaccination studies, the planned study targeted the treatment of patients with a small tumor burden not yet detectable by imaging procedures. The patients were all immunized in the same way using known prostate-specific antigenic structures to enhance the immune response to the malignantly transformed cells. Nineteen patients were treated.

TABLE 9

Characteristics of study population

| | Total | % | Median | Range |
|---|---|---|---|---|
| Age | 19 | | 63 | 55-77 |
| Prior neo-/adjuvant treatment | | | | |
| None | 11 | 58 | | |
| Radiation | 3 | 16 | | |
| Intermittent Hormonal Therapy | 2 | 11 | | |

TABLE 9-continued

Characteristics of study population

|  | Total | % | Median | Range |
|---|---|---|---|---|
| Rad. + Int. Horm. Therapy | 2 | 11 | | |
| Rad. + Chemotherapy | 1 | 5 | | |
| TNM at RPX | | | | |
| T2a-c R0 | 6 | 32 | | |
| T3a-c R0 | 6 | 32 | | |
| T2a-c R1 | 3 | 16 | | |
| T3a-c R1 | 3 | 16 | | |
| T3aN2 R0 | 1 | 5 | | |
| Gleason score | | | | |
| 5-7 | 10 | 53 | | |
| 8-10 | 3 | 16 | | |
| unknown | 6 | 32 | | |
| RPX prior to vaccination in months | | | 41 | 9-124 |
| First relapse post OP in months | | | 14 | 1-90 |
| PSA at vaccination start | | | 0.76 | 0.14-10.8 |

Treatment Plan

After rule-out of manifest metastatic lesions using computed tomography and skeletal scintigraphy, the prostate-specific peptide vaccine was subcutaneously administered according to the different administration forms to patients with detected PSA relapse after prior radical prostatectomy (PSA increase in terms of a 50% elevated value during two measurements at least 14 days apart). The vaccine was administered 8× on days 0, 7, 14, 28, 42, and 56 (approximately 100 micrograms per peptide and injection each time). After each vaccination treatment and again on day 70, PSA was measured to evaluate the therapeutic response.

If a tumor response (complete remission [PSA-CR], partial remission [PSA-PR], or stable clinical course [no change, PSA-NC]) is detected, the patient received the vaccine once a month as maintenance therapy according to the selected administration form. The patient's response to vaccination therapy was evaluated in detail as follows:

Complete remission (PSA-CR): Normalization of an initially elevated PSA level, confirmed by measurement after an interval of at least 4 weeks. Normalization is defined as a PSA nadir of <0.2 ng/ml, which would be expected after radical prostatectomy with complete tumor or prostate extirpation.

Partial remission: a) PSA-PR≤80% (Reduction in an initially elevated PSA level by 80%, confirmed by measurement after an interval of at least 4 weeks); and b) PSA-PR≤50% (Reduction in an initially elevated PSA level by 50%, confirmed by measurement after an interval of at least 4 weeks.)

Stable disease (PSA-SD): No significant change over a period of at least four weeks. This includes stabilization and a reduction of less than 50% and an increase of less than 10%, confirmed by measurement after an interval of at least 4 weeks.

Progression (PSA-PD): Increase in the PSA level by more than 10%, in the event of PSA progression, the study was terminated.

After enrollment of the patients into the study, the epitope-specific vaccine was used; the proteins specifically expressed in prostatic epithelial cells PSMA/PSCA) were taken into account. In addition to investigating the general efficacy of the administered vaccine with respect to monitoring the growth of residual tumor fractions as evaluated by PSA monitoring, this study investigated the effects of various vaccination methods with respect to efficient modulation of the immune system. In addition to simple subcutaneous administration of the peptides alone, various combinations with adjuvants were also used. In particular, depot and adjuvant activity for peptide vaccines of Montanide (a formulation of the classical incomplete Freund's adjuvant suitable for use in humans), which has recently been described very favorably, was used. For this purpose, 500 µl of the peptide solution was mixed with 500 µl of Montanide and administered. Thereby, a water-in-oil emulsion is built that slowly releases the antigen contained in the aqueous phase over weeks. The physical stability of the emulsion is very high, as at 4° C. it can be stored for more than 3 months without significant phase separation. The depot function of Montanide has been exploited in several vaccination trials with good results (Oka et al., 2004).

One study arm investigated the efficacy of vaccination during concomitant stimulation of the immune system by growth factors, GM-CSF, Leukine® solution for injection, GM-CSF is a very commonly used adjuvant in peptide vaccination trials with several thereof reporting enhanced clinical and T-cell responses. Initially, GM-CSF is a dendritic cell recruitment and differentiation factor that is thought to enhance the number of dendritic cells at the vaccines' injection site. Although GM-CSF does not by itself activate antigen presenting cells as dendritic cells and macrophages an indirect activation in vivo has been reported (Molenkamp et al. 2005).

Another study arm investigated the efficacy of vaccination during concomitant activation of dendritic cells by epicutaneous use of imiquimod. Imiquimod was administered as an 5% ointment (Aldara). It has a strong immunostimulatory via its effect on TLR7 positive cells (e.g. plasmacytoid DCs, Langerhans cells, dermal DCs) and activates the MyD88-dependent pathway, Activated APCs release T-cell stimulating and inflammatory cytokines, upregulate costimulation and migrate to draining lymph nodes. The potential of imiquimod to enhance peptide-induced CTL response by mixing the antigens into the ointment or by application of Aldara over the s.c. or i.d. injection site for the antigens has been demonstrated in animal models.

Another study arm investigated the efficacy of vaccination during concomitant activation of dendritic cells by mixing them with protamine-stabilized mRNA encoding mucin-1 to activate TLR 7/8. mRNA shows a broad activation of mouse and human immune cell populations. The presence of the poly-basic protein protamine in the formulation increases the half-life of the mRNA and induces the formation of potentially depot-forming particles. This adjuvant may therefore combine depot-forming and APC-activating properties.

In summary, the administration forms of the vaccine included the following approaches:
  Subcutaneous administration of the peptide vaccine emulsified in Montanide,
  Subcutaneous administration of the peptide vaccine emulsified in 500 of Montanide in combination with topical administration of 225 of GM-CSF with the objective of achieving a stronger immune response triggered by concomitant administration of growth factors,
  Subcutaneous administration of the peptide vaccine emulsified in 500 µl of Montanide in combination with local hyperthermia, the latter given with the objective of achieving a thermally induced stronger immune response, Subcutaneous administration of the peptide vaccine emulsified in 500 µl of Montanide in combination with epicutaneous imiquimod in order to activate dendritic cells via TLR 7, Subcutaneous administration of the peptide vaccine emulsified in 500 µl of Montanide together with 55 µl of mucin-1 mRNA/protamine in order to activate dendritic cells via TLR 7/8.

Schedule: The entire duration of the study was 3 years.

Prostate-specific peptide vaccines were administered to patients on days 0, 7, 14, 28, 42, and 56. In patients with stable disease or an objective tumor response (PSA-CR or PSA-PR), the vaccinations were received once a month i.d. until detectable progression occurred. On the basis of the experience available thus far, peptide injections are tolerated without significant adverse reactions. Because the response to vaccination therapy was evaluated solely serologically on the basis of the PSA measurement, a test was performed at the start of the study to determine whether the administered vaccine interferes with PSA measurement in vitro, which could simulate a clinical response. On days 0, 7, 14, 28, 42, 56, and 70, blood samples were taken for laboratory tests, PSA levels, differential blood count, FACS analysis, and cytokines. If treatment is continued past day 70, 6-week PSA monitoring was performed in order to detect treatment failure in a timely manner.

Treatment was ended if documented progression of the disease occurred in terms of a continuous PSA elevation.

Beginning on day 84, immunization therapy was continued at 1-week intervals until documented progression or up to day 420 (15 months). Decisions regarding continuation of therapy (in successful cases) outside of this study were made on a case-by-case basis. Unexpected adverse reactions did not occur in this study.

The laboratory tests included coagulation, electrolytes. LDH, ß2-M, CK, hepatic enzymes, bilirubin, creatinine, uric acid, total protein, coagulation, CRP, differential blood count with smear, PSA level, cytokines, FACS, Elispot.

Analysis of the cutaneous reaction to defined bacterial and fungal antigens (48-72 hours after administration, delayed type hypersensitivity (DTH), T cell-mediated, will serve as an analysis of the patient's cellular immune system before the start of the study).

The peptides required for the study (nona-peptides) were manufactured in the laboratory of PD Dr. Stefan Stevanovic in the department of Prof. H.-G. Rammensee. These peptides were purified by HPLC and analyzed by mass spectrometry. The purity of the peptides can also be checked by HPLC, mass spectrometry, and Edman sequencing. Using these methods, purity of up to 98% can be documented (which must be regarded as the maximum according to the current state of the methods). The synthesized peptides were dissolved in DMSO (CryoSure, WAK Chemie Medical GmbH; 10 mg/ml), diluted to 1:10 in Ampuwa (Fresenius Kabi), and aliquoted under sterile conditions.

Clinical Response

In two patients PET-CT scan could reveal local recurrence after local tumor was detected by continuous digital rectal examination. In the remaining 17 patients the location of disease activity could not be verified at study termination.

Repeated laboratory evaluation of differential blood count or extensive clinical chemistry did not reveal any abnormalities or changes during the study.

Of the 19 patients 16 patients reacted to the Survivin II peptide (IFN-g ELISPOT, +/−ICS) according to SEQ ID NO:12. Among them, were 12 patients with induction of an anti-survivin T-cell response upon vaccination, 2 with pre existing anti-Survivin T cells and 2 patients of whom it was not determined, whether pre existing anti-Survivin T cells were abundant.

Biochemical Response

Complete response was considered as a non-detectable. PSA value according to the lowest value detectable of the laboratory collaborating after initially elevated PSA. The measurement had to be confirmed after an interval of at least four weeks. A PR>80% and >50% had to be reevaluated after four weeks accordingly. A PSA within the range of less than 50% decrease or less than 10% increase reflected stable disease if at least confirmed after four weeks. Progressive disease was considered any increase of more than 10% of PSA at treatment start.

Biochemical response in patients who terminated the study was followed until they received further treatment with local radiation or antihormonal therapy.

19 patients consented to participate and the data was analyzed with the longest follow-up lasting about 3.75 years.

PSA Stability and DT Increase

PSA values of two patients (10.2%) exhibited stability according to the above mentioned criteria of biochemical response which state that no rise of the PSA value greater than 10% at treatment start had occurred at study end (FIG. 6, Tables 10, 11, and 12). Follow up in those two cases was conducted 14 and 16 months after the last vaccine application. Average duration of stability was 24 months (28 and 31) at data cut-off with an average of 18 vaccinations (14 and 20) applied.

One of these two patients showed partial response >50% for a period of 9 months, followed by a period of slow PSA rise with a doubling time of 20.5 compared to 9.8 months prior vaccination. Initial PSA relapse started 18 months post surgery for a pT2pN0 Gleason 5 tumor.

At data analysis Patient 8 exhibited stable disease since the beginning of the vaccination program 28 months ago. He had stopped treatment due to an allergic reaction after 10 months and the 14$^{th}$ vaccination, He had an unfavorable pT3b Gleason 3+4 situation with a PSA nadir after radical prostatectomy not below 0.6 ng/ml and PSA progression without timely delay after initial decline postoperatively. Doubling time slowed from 6.6 months to 148 months.

These two patients received dermal Imiquimod at the application site at each peptide vaccination.

PSA DT Increase without PSA Stability

PSA DT of patient 11 was increased from 1.5 to 10.1 months during six month on study. Since he started with a PSA of 10.8 ng/ml and progressed to 17.8 ng/ml he terminated study procedures to receive antiandrogen monotherapy without any malignant lesions visualized in PET-CT. He received Aldara as adjuvant.

Patient 16 started into vaccine treatment plus Mucin-1-mRNA/protamine with a doubling time of 6.1 months. PSA velocity declined into a half life time of 2.7 months for five months followed by a statistically calculated rise of PSA DT of 14.4 months which is continuing 16 months after treatment start. With an initial PSA of 0.29 ng/ml, he dropped to 0.19 ng/ml during the first 5 months on study treatment, rose to 0.4 ng/ml within the following 8 months and terminated the study per protocol with 0.41 ng/ml 19 months after treatment start.

PSA Progression

Patient 5 progressed during the study according to the estimated PSA doubling time before vaccination. However, he experienced a PSA decline with a half-time life of 20.2 months after treatment end for a continuing period of 10 months at data cut-off. He still was not receiving any secondary treatment after vaccination end. He was vaccinated with montanide as the only adjuvant.

TABLE 10

PSA Doubling Time in months

| | Total | % | Geometric Mean | Range of DT |
|---|---|---|---|---|
| PSA DT prior vaccination in months | 19 | | 8.3 | 1.5-44.8 |
| PSA DT at study end or at end of follow-up | 18* | | 11.2 | 2.2-148 |
| No change of PSA DT during vaccination | 11 | 58 | | 2.2-44.8 |
| Increased PSA DT continuing at end of study | 4 | 21 | | |
| No change of PSA DT during vacc but decline after | 1 | 5 | | |
| Interim PSA decline or DT increase followed by DT decrease | 3 | 16 | | |

*PSA DT at study end or end of follow-up was not included for Pat. 5 due to PSA decline 7. Binding of HLA class I-Restricted Peptides of the Invention to HLA-A*0201

Objective and Summary

The objective of this analysis was to evaluate the affinity of the HLA class I peptides to the MHC molecule coded by the HLA-A*0201 allele as this is an important parameter for the mode of action of IMA941. Affinities to HLA-A*0201 were medium to high for all 10 HLA class I-restricted peptide in IMA941 and MET-001, dissociations constants (KD) being in the range from 0.14 (MET-001) to 2.05 nM (CSP-001). All values are in the range between 0.1 for the strong binder HBV-001 and 4.4 for the intermediate binder MUC-001. These results confirmed the strong binding affinity of all HLA class I peptides of the IMA941 vaccine candidate and the MET-005 derived MET-001 to HLA-A*02.

Principle of Test

Stable HLA/peptide complexes consist of three molecules: HLA heavy chain, beta-2 microglobulin (b2m) and the peptidic ligand. The activity of denatured recombinant HLA-A*0201 heavy chain molecules alone can be preserved making them functional equivalents of "empty HLA-A*0201 molecules". When diluted into aqueous buffer containing b2m and an appropriate peptide, these molecules fold rapidly and efficiently in an entirely peptide-dependent manner. The availability of these molecules is used in an ELISA-based assay to measure the affinity of interaction between peptide and HLA class I molecule (Sylvester, 2002).

Purified recombinant HLA-A*0201 molecules were incubated together with b2m and graded doses of the peptide of interest. Instead of full-length MET-005 that does not possess HLA class I binding capacities, the proven A*0— binding product MET-001 was included into the analysis that is generated in vivo from MET-005 by naturally occurring antigen processing. The amount of de novo-folded HLA/peptide complexes was determined by a quantitative ELISA. Dissociation constants (KD values) were calculated using a standard curve recorded from dilutions of a calibrant HLA/peptide complex.

Results

Results are shown in FIG. 2. A lower KD value reflects higher affinity to HLA-A*0201. Most of the IMA941 peptides had similar and strong affinities to HLA-A*0201 within the range from 0.1 (HBV-001, strong binder) to 44.4 nM (MUC-001, intermediate binder). Thereby, all IMA941 class I TUMAPs have a medium to strong binding affinity to the MHC molecule A*02.

8. Binding of HLA class II-Restricted Peptides of the Invention to HLA-DR

Objective and Summary

Class II TUMAPs activate helper T cells which play a crucial role in assisting the function of CTLs triggered by class I-restricted TUMAPs. Binding of the IMA941 class II peptides to several different HLA class II molecules (promiscuous binding) is important to ensure that the majority of patients treated with the vaccine candidate IMA941 are able to benefit from a supportive helper T cell response. HLA-DR for example, the most dominantly expressed human HLA class II molecule, is highly polymorphic with several hundreds of known alleles. Based on known allele frequencies for HLA-DRB1 haplotypes and well-established binding algorithms, it can be predicted that both HLA class II ligands in IMA941-IMA-BIR-002 and IMA-MET-005—are promiscuous HLA-DR binding peptides. In detail, the probability that an HLA-A*02-positive Caucasian expresses at least one suitable HLA-DR allele is >90% for both IMA941 class II TUMAPs. As the remaining human class II alleles HLA-DQ and -DP were omitted from this calculation due to the lack of frequency data or binding prediction algorithms, the real promiscuity is most likely even higher. The calculated promiscuity of the two IMA941 class II TUMAPs is in the same range as for the known pan-DR epitope (PADRE, genotypic frequency Fprojected 93.1%). In addition, the promiscuous binding of these peptides was confirmed experimentally by in vitro binding assays. Moreover, for IMA-BIR-002 a high in vivo immunogenicity could be demonstrated (see above). Summarizing, these results confirm that MET-005 and BIR-002 are promiscuous HLA-DR binding peptides.

Principle of Binding Prediction

Using the SYFPEITHI algorithm developed at the University of Tübingen (Rammensee et al., 1997; Rammensee et al., 1999), binding of IMA941 class II TUMAPs to several common HLA-DR alleles was ranked. The algorithm has already been successfully used to identify class I and class II epitopes from a wide range of antigens, from the human tumor-associated antigens TRP2 (class I) (Sun et al., 2000) and SSX2 (class II) (Neumann et al., 2004). The threshold for binding was defined at a score of 18 based on the analysis of binding scores of known published promiscuous HLA-DR ligands.

Published HLA-DR haplotype frequencies among the MLA-A*02 positive Caucasian population (Mori et al., 1997) and frequencies of high-resolution haplotypes (Chanock et al., 2004) were used (see Table 2). The haplotype frequency is the frequency of a distinct allele on an individual chromosome. Due to the diploid set of chromosomes within mammalian cells, the frequency of genotypic occurrence of this allele is higher and can be calculated employing the Hardy-Weinberg principle (haplotype frequency $G_f$ results in a genotypic occurrence F ($F=2G_f-G_f^2$]).

The SUM of frequency of DRB1-haplotypes with known SYFPEITHI matrix and known individual frequency among the A*02+ Caucasian population is 47.8%. Therefore, the predicted binding distribution of class ft TUMAPs to these alleles was projected to the remaining 52.2% of DRB1-alleles for which these data are not available.

Finally, promiscuous binding is defined as binding of a peptide to several IMA-DR alleles with the probability that one of these is expressed in the Caucasian population being at least 50%.

Principle of In Vitro Binding Assay (ProImmune REVEAL™)

IMA-BIR-002 and IMA-MET-005 were assembled with HLA-DR broad antigens (HLA-DR1 to DR7, which comprise also the split antigens HLA-DR11 to -DR15 (Mori et al., 1997)) and analyzed using the REVEAL™ MHC:peptide binding assay (ProImmune, Oxford, UK) to determine their level of incorporation into MHC molecules. In this assay, binding was compared to that of a pass/fail control binder, and to a positive control peptide for each HLA-DR antigen.

Results

Based on the prediction by the SYFPEITHI algorithm IMA-BIR-002 is likely to bind to ⅞ of HLA-DR alleles with known binding motif (Table 11). The probability that an HLA-A*02 positive Caucasian expresses at least one suitable HLA-DRB1 allele for IMA-BIR-002 is 92.6%. Therefore, both IMA941 class II peptides are predicted to be promiscuous HLA-DR binders.

If the haplotype frequency of binding HLA-DRB1 alleles was overestimated through this approach by factor two, their genotypic occurrence would still be >50% for all class ft TUMAPs in IMA941. In addition, experimental confirmation for promiscuous binding of IMA-BIR-002 to HLA-DR1, 3, 4 and 11 was obtained from in vitro binding data (FIG. 3).

As IMA-BIR-002 has proven broad immunogenicity in a clinical trial in prostate cancer patients with different HLA-DR alleles, the promiscuitivity of this class II peptide has clearly been proven in vivo.

In conclusion, in silico analysis of the HLA-DR binding properties of the two class II peptides contained in IMA941 and additional experimental evidence from in vitro assays and from a clinical trial with BIR-002 strongly suggest that these TUMAPs are promiscuous binders of human class II HLA molecules.

Ashley A C, Sargent D J, Alberts S R, Grothey A, Campbell M E, Morton R F, Fuchs C S, Ramanathan R K, Williamson S K, Findlay B P, Pitot H C, Goldberg R M (2007). Updated efficacy and toxicity analysis of irinotecan and oxaliplatin (IROX): intergroup trial N9741 in first-line treatment of metastatic colorectal cancer. Cancer 110, 670-677.

Aucouturier J, Dupuis L, Ganne V (2001). Adjuvants designed for veterinary and human vaccines. Vaccine 19, 2666-2672.

Banchereau J, Palucka A K, Dhodapkar M, Burkeholder S, Taquet N, Rolland A, Taquet S, Coquery S, Wittkowski K M, Bhardwaj N, Pineiro L, Steinman R, Fay J (2001). Immune and clinical responses in patients with metastatic melanoma to CD34(+) progenitor-derived dendritic cell vaccine. Cancer Res. 61, 6451-6458.

Banerjee S K, Weston A P, Zoubine M N, Campbell D R, Cherian R (2000). Expression of cdc2 and cyclin B1 in Helicobacter pylori-associated gastric MALT and MALT lymphoma: relationship to cell death, proliferation, and transformation. Am J Pathol. 156, 217-225.

Bauer B, Bartfeld S, Meyer T F (2009). H. pylori selectively blocks EGFR endocytosis via the non-receptor kinase c-Abl and CagA. Cell Microbiol. 11, 156-169.

Bertoletti A, Chisari F V, Penna A, Guilhot S, Galati L, Missale G, Fowler P, Schlicht H J, Vitiello A, Chesnut R C, (1993). Definition of a minimal optimal cytotoxic T-cell epitope within the hepatitis B virus nucleocapsid protein. J. Virol. 67, 2376-2380.

Bertolini G, Roz L, Perego P, Tortoreto M, Fontanella E, Gatti L, Pratesi G, Fabbri A, Andriani F, Tinelli S, Roz E, Caserini R, Lo V S, Camerini T, Mariani L, Delia D, Calabro E, Pastorino U, Sozzi G (2009). Highly tumorigenic lung cancer CD133+ cells display stem-like features and are spared by cisplatin treatment. Proc Natl. Acad. Sci. U.S.A 106, 16281-16286.

TABLE 11

Binding scores of IMA941 class II TUMAPs to HLA-DR alleles with known binding motif. Shown are the SYFPEITHI binding scores for the most common HLA-DRB1 alleles in the Caucasian population. p gives the haplotype frequencies among HLA-A*02 positive Caucasians. The peptide was considered as binding to an HLA molecule if the score was equal to or higher than 18. Accumulation of the p values for binding DRB1 alleles results in the minimal haplotype frequency $p_{min}$. Extrapolation of these frequencies to all DRB1 alleles including those with incomplete binding prediction matrix or frequency data gives the projected haplotype frequency $p_{projected}$ that corresponds to the frequency of genotypic occurrence $F_{projected}$.

IMA-BIR-002

| | DRB1* allele | | | | | | | |
|---|---|---|---|---|---|---|---|---|
| | 0101 | 0301 | 0401 | 0404 | 0701 | 1101 | 1104 | 1501 |
| SYFPEITHI score | 28 | 29 | 28 | 24 | 14 | 32 | 24 | 30 |
| p | 6.6% | 5.9% | 9.6% | 6.0% | 13.0% | 4.4% | 2.3% | n.d. |
| predicted binding | yes | yes | yes | yes | no | yes | yes | yes |
| $p_{min}$ | | | | | | | | 34.8% |
| Haplotypic frequency $p_{projected}$ | | | | | | | | 72.8% |
| Genotypic frequency $F_{projected}$ | | | | | | | | 92.6% | n.d. = no data

REFERENCE LIST

Allison J P, Krummel M F (1995). The Yin and Yang of T cell costimulation. Science 270, 932-933.

Angileri F F, Aguennouz M, Conti A, La T D, Cardali S, Crupi R, Tomasello C, Germano A, Vita G, Tomasello F (2008). Nuclear factor-kappaB activation and differential expression of survivin and Bcl-2 in human grade 2-4 astrocytomas. Cancer 112, 2258-2266.

Bierie B, Moses H L (2006). TGF-beta and cancer. Cytokine Growth Factor Rev. 17, 29-40.

Brown C E, Starr R, Martinez C, Aguilar B, D'Apuzzo M, Todorov I, Shih C C, Badie B, Hudecek M, Riddell S R, Jensen M C (2009). Recognition and killing of brain tumor stem-like initiating cells by CDD8+ cytolytic T cells. Cancer Res 69, 8886-8893.

Castriconi R, Dondero A, Negri F, Bellora F, Nozza P, Carnemolia B, Raso A, Moretta L, Moretta A, Bottino C (2007). Both CD133+ and C. Eur. J. Immunol. 37, 3190-3196.

Chakravarti A, Noll E, Black P M, Finkelstein D F, Finkelstein D M, Dyson N J, Loeffler J S (2002). Quantitatively determined survivin expression levels are of prognostic value in human gliomas. J Clin Oncol 20, 1063-1068.

Chanock S J, Foster C B, Miller F W, O'Hanlon T P (2004). HLA-A, -B, -Cw, -DQA1 and -DRB1 Alleles in a Caucasian Population from Bethesda, USA. Hum. Immunol. 65, 1211-1223.

Chen Z, O'Shea J J (2008). Regulation of IL-17 production in human lymphocytes. Cytokine 41, 71-78.

Cisek L J, Corden J L (1989). Phosphorylation of RNA polymerase by the murine homologue of the cell-cycle control protein cdc2. Nature 3.39, 679-684.

Corso S, Migliore C, Ghiso E, De R G, Comoglio P M, Giordano S (2008). Silencing the MET oncogene leads to regression of experimental tumors and metastases. Oncogene 27, 684-693.

Cox C V, Diamanti P, Evely R S, Kearns P R, Blair A (2009). Expression of CD133 on leukemia-initiating cells in childhood ALL. Blood 113, 3287-3296.

DeLuca J G, Dong Y, Hergert P, Strauss J, Hickey J M, Salmon E D, McEwen B F (2005). Hec1 and nuf2 are core components of the kinetochore outer plate essential for organizing microtubule attachment sites. Mol. Biol. Cell 16, 519-531.

Deng H, Guo R F, Li W M, Zhao M, Lu Y Y (2005). Matrix metalloproteinase 11 depletion inhibits cell proliferation in gastric cancer cells. Biochem. Biophys. Res Commun. 326, 274-281.

Deremer D L, Ustun C, Natarajan K (2008). Nilotinib: a second-generation tyrosine kinase inhibitor for the treatment of chronic myelogenous leukemia. Clin Ther. 30, 1956-1975.

Egland K A, Liu X F, Squires S, Nagata S, Man Y G, Bera T K, Onda M, Vincent J J, Strausberg R L, Lee B, Pastan I (2006). High expression of a cytokeratin-associated protein in many cancers. Proc Natl. Acad. Sci. U.S.A 103, 5929-5934.

Eramo A, Lotti F, Sette G, Pilozzi E, Biffoni M, Di V A, Conticello C, Ruco L, Peschle C, De M R (2008). Identification and expansion of the tumorigenic lung cancer stem cell population. Cell Death Differ 15, 504-514.

Esashi F, Christ N, Gannon J, Liu Y, Hunt T, Jasin M, West S C (2005). CDK-dependent phosphorylation of BRCA2 as a regulatory mechanism for recombinational repair. Nature 434, 598-604.

Falk K, Rotzschke O, Stevanovic S, Jung G, Rammensee H G (1991). Allele-specific motifs revealed by sequencing of self-peptides eluted from MHC molecules. Nature 351, 290-296.

Flanagan J M, Funes J M, Henderson S. Wild L, Carey N, Boshoff C (2009). Genomics screen in transformed stem cells reveals RNASEH2A, PPAP2C, and ADARB1 as putative anticancer drug targets. Mol. Cancer. Ther. 8, 249-260.

Gabrilovich D I, Chen H L, Girgis K R, Cunningham H T, Meny G M, Nadaf S, Kavanaugh D, Carbone D P (1996). Production of vascular endothelial growth factor by human tumors inhibits the functional maturation of dendritic cells. Nat. Med. 2, 1096-1103.

Grunda J M, Nabors L B, Palmer C A, Chhieng D C, Steg A, Mikkelsen T, Diasio R B, Zhang K, Allison D, Grizzle W E, Wang W, Gillespie G Y, Johnson M R (2006). Increased expression of thymidylate synthetase (TS), ubiquitin specific protease 10 (USP10) and survivin is associated with poor survival in glioblastoma multiforme (GBM). J Neurooncol. 80, 261-274.

Harada T, Chelala C, Crnogorac-Jurcevic T, Lemoine N R (2009). Genome-wide analysis of pancreatic cancer using microarray-based techniques. Pancreatology. 9, 13-24.

Harper L J, Piper K, Common J, Fortune F, Mackenzie I C (2007). Stem cell patterns in cell lines derived from head and neck squamous cell carcinoma. J Oral Pathol. Med. 36, 594-603.

Hayama S, Daigo Y, Kato T, Ishikawva N, Yamabuki T, Miyamoto M, Ito T, Tsuchiya E, Kondo S, Nakamura Y (2006). Activation of CDCA1-KNTC2, members of centromere protein complex, involved in pulmonary carcinogenesis. Cancer Res 66, 10339-10348.

Horton R A, Strachan E A, Vogel K W, Riddle S M (2007). A substrate for deubiquitinating enzymes based on time-resolved fluorescence resonance energy transfer between terbium and yellow fluorescent protein. Anal. Biochem. 360, 138-143.

Huang Y, Fan J, Yang J, Zhu G Z (2008). Characterization of GPR56 protein and its suppressed expression in human pancreatic cancer cells. Mol. Cell. Biochem. 308, 133-139.

Jia H L, Ye Q H, Qin L X, Budhu A, Forgues M, Chen Y, Liu Y K, Sun H C, Wang L, Lu H Z, Shen F, Tang Z Y, Wang X W (2007). Gene expression profiling reveals potential biomarkers of human hepatocellular carcinoma. Clin Cancer Res 13, 1133-1139.

Jung G, Ledbetter J A, Muller-Eberhard H J (1987). Induction of cytotoxicity in resting human T lymphocytes bound to tumor cells by antibody heteroconjugates. Proc Natl Acad Sci USA 84, 4611-4615.

Jung H M, Choi S J, Kim J K (2009). Expression profiles of SV40-immortalization-associated genes upregulated in various human cancers. J Cell Biochem. 106, 703-713.

Kajiwara Y, Yamasaki F, Hama S, Yahara K, Yoshioka H, Sugiyarna K, Arita K, Kurisu K (2003). Expression of survivin in astrocytic tumors: correlation with malignant grade and prognosis. Cancer 97, 1077-1083.

Kaneko N, Miura K, Gu Z, Karasawa H, Ohnuma S, Sasaki H, Tsukamoto N, Yokoyama S, Yamamura A, Nagase H, Shibata C, Sasaki I, Horii A (2009). siRNA-mediated knockdown against CDCA1 and KNTC2, both frequently overexpressed in colorectal and gastric cancers, suppresses cell proliferation and induces apoptosis. Biochem. Biophys. Res Commun. 390, 1235-1240.

Knutson K L, Disis M L (2005). Augmenting T helper cell immunity in cancer. Curr. Drug Targets. Immune. Endocr. Metabol. Disord. 5, 365-371.

Koch M, Beckhove P, Op den W J, Autenrieth D, Wagner P, Nummer D, Specht S, Antolovic D, Galindo L, Schmitz-Winnenthal F H, Schirrmacher V, Buchler M W, Weitz J (2006). Tumor infiltrating T lymphocytes in colorectal cancer: Tumor-selective activation and cytotoxic activity in situ. Ann. Surg. 244, 986-992.

Krieg A M (2006). Therapeutic potential of Toll-like receptor 9 activation. Nat. Rev. Drug Discov. 5, 471-484.

Liu X, Chen N, Wang X, He Y, Chen X, Huang Y, Yin W, Zhou Q (2006). Apoptosis and proliferation markers in diffusely infiltrating astrocytomas: profiling of 17 molecules. J Neuropathol. Exp. Neurol. 65, 905-913.

Livingston B D, Crimi C, Grey H, Ishioka G, Chisari F V, Fikes J, Grey H, Chesnut R W, Sette A (1997). The hepatitis B virus-specific CTL responses induced in humans by lipopeptide vaccination are comparable to those elicited by acute viral infection. J. Immunol. 159, 1383-1392.

Ma S, Chan K W, Hu L, Lee T K, Wo J Y, Ng I O, Zheng B J, Guan X Y (2007). Identification and characterization of tumorigenic liver cancer stem/progenitor cells. Gastroenterology 132, 2542-2556.

Martin C M, Astbury K, McEvoy L, O'Toole S, Sheils O, O'Leary J J (2009), Gene expression profiling in cervical cancer: identification of novel markers for disease diagnosis and therapy. Methods Mol. Biol. 511, 333-359.

Mellai M, Caldera V, Patrucco A, Annovazzi L, Schiffer D (2008). Survivin expression in glioblastomas correlates with proliferation, but not with apoptosis. Anticancer Res. 28, 109-118.

Mizrak D, Brittan M, Alison M (2008). CD133: molecule of the moment. J Pathol. 214, 3-9.

Molenkamp B G, Vuylsteke R J, van Leeuwen P A, Meijer S, Vos W, Wijnands P G, Scheper R J, de Gruijl T D (2005). Matched skin and sentinel lymph node samples of melanoma patients reveal exclusive migration of mature dendritic cells. Am. J. Pathol. 167, 1301-1307.

Monzani E, Facchetti F, Galmozzi E, Corsini E, Benetti A, Cavazzin C, Gritti A, Piccinini A, Porro D, Santinami M, Invernici G, Parati E, Alessandri G, La Porta C A (2007). Melanoma contains CD133 and ABCG2 positive cells with enhanced tumourigenic potential. Eur. J Cancer 43, 935-946.

Mori M, Beatty P G, Graves M, Boucher K M, Milford E L (1997). HLA gene and haplotype frequencies in the North American population: the National Marrow Donor Program Donor Registry. Transplantation 64, 1017-1027.

Nakaigawa N, Yao M, Baba M, Kato S, Kishida T, Hattori K, Nagashima Y, Kubota Y (2006). Inactivation of von Hippel-Lindau gene induces constitutive phosphorylation of MET protein in clear cell renal carcinoma. Cancer Res. 66, 3699-3705.

Neumann F, Wagner C, Kubuschok B, Stevanovic S, Rammensee H-G, Pfreundschuh M (2004). Identification of an antigenic peptide derived from the cancer-testis antigen NY-ESO-1 binding to a broad range of HLA-DR subtypes. Cancer Immunol. Immunother. 53, 589-599.

Nguyen Q N, Chavli R V, Marques J T, Conrad P G, Jr., Wang D, He W, Belisle B E, Zhang A, Pastor L M, Witney F R, Morris M, Heitz F, Divita G, Williams B R, McMaster G K (2006). Light controllable siRNAs regulate gene suppression and phenotypes in cells. Biochim. Biophys. Acta 1758, 394-403.

Nishio K, Kim S W, Kawai K, Mizushima T, Yamane T, Hamazaki J, Murata S, Tanaka K, Morimoto Y (2009). Crystal structure of the de-ubiquitinating enzyme UCH37 (human UCH-L5) catalytic domain. Biochem. Biophys. Res Commun. 390, 855-860.

Ohnuma S, Miura K, Horii A, Fujibuchi W, Kaneko N, Gotoh O, Nagasaki H, Mizoi T, Tsukamoto N, Kobayashi T, Kinouchi M, Okabe M, Sasaki H, Shiiba K, Miyagawa K, Sasaki 1 (2009). Cancer-associated splicing variants of the CDCA1 and MSMB genes expressed in cancer cell lines and surgically resected gastric cancer tissues. Surgery 145, 57-68.

Oka Y, Tsuboi A, Taguchi T, Osaki T, Kyo T, Nakajima H, Elisseeva O A, Oji Y, Kawakami M, Ikegame K, Hosen N, Yoshihara S, Wu F, Fujiki F, Murakami M, Masuda T, Nishida S, Shirakata T, Nakatsuka S, Sasaki A, Udaka K, Dohy H, Aozasa K, Noguchi S, Kawase I, Sugiyama H (2004). Induction of WT1 (Wilms' tumor gene)-specific cytotoxic T lymphocytes by WT1 peptide vaccine and the resultant cancer regression. Proc Natl. Acad. Sci. U.S.A 101, 13885-13890.

Pietra G, Manzini C, Vitale M, Balsamo M, Ognio E, Boitano M, Queirolo P, Moretta L, Mingari M C (2009). Natural killer cells kill human melanoma cells with characteristics of cancer stem cells. Int Immunol. 21, 793-801.

Poppe M, Feller S M, Romer G, Wessler S (2007). Phosphorylation of *Helicobacter pylori* CagA by c-Abl leads to cell motility. Oncogene 26, 3462-3472.

Pytel D, Sliwinski T, Poplawski T, Ferriola D, Majsterek I (2009). Tyrosine kinase blockers: new hope for successful cancer therapy. Anticancer Agents Med. Chem. 9, 66-76.

Qian Z, Joslin J M, Tennant T R, Reshmi S C, Young D J, Stoddart A, Larson R A, Le Beau M M (2009). Cytogenetic and genetic pathways in therapy-related acute myeloid leukemia. Chem. Biol. Interact.

Rammensee H G, Bachmann J, Emmerich N P, Bachor O A, Stevanovic S (1999). SYFPEITHI: database for MHC ligands and peptide motifs. Immunogenetics 50, 213-219.

Rammensee, H. G., Bachmann, J., and Stevanovic. S. (1997). MHC Ligands and Peptide Motifs. Springer-Verlag, Heidelberg, Germany).

Rammensee H G, Falk K, Rotzschke O (1993). Peptides naturally presented by MHC class I molecules. Annu. Rev. Immunol. 11, 213-244.

Rappa G, Fodstad O, Lorico A (2008). The stem cell-associated antigen CD133 (Prominin-1) is a molecular therapeutic target for metastatic melanoma. Stem Cells 26, 3008-3017.

Ricci-Vitiani L, Lombardi D G, Signore M, Biffoni M, Pallini R, Parati E, Peschle C, De Maria R (2007). Human neural progenitor cells display limited cytotoxicity and increased oligodendrogenesis during inflammation. Cell Death. Differ. 14, 876-878.

Richardson G D, Robson C N, Lang S H, Neal D E, Maitland N J, Collins A T (2004). CD133, a novel marker for human prostatic epithelial stem cells. J Cell Sci. 117, 3539-3545.

Rutella S, Bonanno G, Procoli A, Mariotti A, Corallo M, Prisco M G, Eramo A, Napoletano C, Gallo D, Perillo A, Nuti M, Pierelli L, Testa U. Scambia G, Ferrandina G (2009). Cells with characteristics of cancer stem/progenitor cells express the CD133 antigen in human endometrial tumors. Clin Cancer Res 15, 4299-4311.

Saito T, Arifin M T, Hama S, Kajiwara Y, Sugiyama K, Yamasaki F, Hidaka T, Arita K, Kurisu K (2007). Survivin subcellular localization in high-grade astrocytomas: simultaneous expression in both nucleus and cytoplasm is negative prognostic marker. J Neurooncol. 82, 193-198.

Sasaki T, Lopes M B, Hankins G R, Helm G A (2002). Expression of survivin, an inhibitor of apoptosis protein, in tumors of the nervous system. Acta Neuropathol. 104, 105-109.

Seeger F H, Schirle M, Gatfield J, Arnold D, Keilholz W, Nickolaus P, Rammensee H G, Stevanovic S (1999). The HLA-A*6601 peptide motif: prediction by pocket structure and verification by peptide analysis. Immunogenetics 49, 571-576.

Shapiro G I (2006). Cyclin-dependent kinase pathways as targets for cancer treatment. J Clin Oncol 24, 1770-1783.

Singh S K, Clarke I D, Terasaki M, Bonn V E, Hawkins C, Squire J, Dirks P B (2003). Identification of a cancer stein cell in human brain tumors. Cancer Res. 63, 5821-5828.

Singh S K, Hawkins C, Clarke I D, Squire J A, Bayani J, Hide T, Henkelman R M, Cusimano M D, Dirks P B (2004). Identification of human brain tumour initiating cells. Nature 432, 396-401.

Smith L M, Nesterova A, Ryan M C, Duniho S, Jonas M, Anderson M, Zabinski R F, Sutherland M K, Gerber H P, Van Orden K L, Moore P A, Ruben S M, Carter P J (2008). CD133/prominin-1 is a potential therapeutic target for antibody-drug conjugates in hepatocellular and gastric cancers. Br. J. Cancer 99, 100-109.

Stemmann O, Zou H, Gerber S A, Gygi S P, Kirschner M W (2001). Dual inhibition of sister chromatid separation at metaphase. Cell 107, 715-726.

Suetsugu A, Nagaki M, Aoki H, Motohashi T, Kunisada T, Moriwaki H (2006). Characterization of CD133+ hepatocellular carcinoma cells as cancer stem/progenitor cells. Biochem. Biophys. Res. Commun. 351, 820-824.

Sun Y, Song M, Stevanovic S, Jankowiak C, Paschen A, Rammensee H G, Schadendorf D (2000). Identification of a new HLA-A(*)0201-restricted T-cell epitope from the tyrosinase-related protein 2 (TRP2) melanoma antigen. Int. J. Cancer 87, 399-404.

Suva M L, Riggi N, Stehle J C, Baumer K, Tercier S, Joseph J M, Suva D, Clement V, Provero P, Cironi L, Osterheld M C, Guillou L, Stamenkovic I (2009). Identification of Cancer Stem Cells in Ewing's Sarcoma. Cancer Res.

Sylvester R K (2002). Clinical applications of colony-stimulating factors: a historical perspective. Am J Health Syst. Pharm. 59, S6-12.

Takaishi S, Okumura T, Tu S, Wang S S, Shibata W, Vigneshwaran R, Gordon S A, Shimnada Y, Wang T C (2009). Identification of gastric cancer stem cells using the cell surface marker CD44. Stem Cells 27, 1006-1020.

Tirino V, Camerlingo R, Franco R, Malanga D, La R A, Viglietto G, Rocco G, Pirozzi G (2009). The role of CD133 in the identification and characterisation of tumour-initiating cells in non-small-cell lung cancer. Eur. J. Cardiothorac. Surg 36, 446-453.

Todaro M, Alea M P, Di Stefano A B, Cammareri P, Vermeulen L, Iovino F, Tripodo C, Russo A, Gulotta G, Medema J P, Stassi G (2007). Colon cancer stem cells dictate tumor growth and resist cell death by production of interleukin-4. Cell Stem Cell 1, 389-402.

Uematsu M, Ohsawa I, Aokage T, Nishirnaki K, Matsumoto K, Takahashi H, Asoh S, Teramoto A, Ohta S (2005). Prognostic significance of the immunohistochemical index of survivin in glioma: a comparative study with the MIB-1 index. J Neurooncol. 72, 231-238.

Walter S, Herrgen L, Schoor O, Jung G, Wernet D, Buhring H J, Rammensee H G, Stevanovic S (2003). Cutting edge: predetermined avidity of human CD8 T cells expanded on calibrated MHC/anti-CD28-coated microspheres. J. Immunol. 171, 4974-4978.

Wicks S J, Grocott T, Haros K, Maillard M, ten D P, Chantry A (2006). Reversible ubiquitination regulates the Smad/TGF-beta signalling pathway. Biochem. Soc Trans. 34, 761-763.

Wicks S J, Haros K, Maillard M, Song L, Cohen R E, Dijke P T, Chantry A (2005). The deubiquitinating enzyme UCH37 interacts with Smads and regulates TGF-beta signalling. Oncogene 24, 8080-8084.

Xie D, Zeng Y X, Wang H J, Wen J M, Tao Y, Sham J S, Guan X Y (2006). Expression of cytoplasmic and nuclear Survivin in primary and secondary human glioblastoma. Br. J. Cancer 94, 108-114, Yang L, Anderson D E, Baecher-Allan C, Hastings W D, Bettelli E, Oukka M, Kuchroo V K, Hafler D A (2008). IL-21 and TGF-beta are required for differentiation of human T(H)17 cells. Nature.

Yasui W, Ayhan A, Kitadai Y, Nishimura K, Yokozaki H, Ito H, Tahara E (1993). Increased expression of p34cdc2 and its kinase activity in human gastric and colonic carcinomas. Int J Cancer 53, 36-41.

Yin S, Li J, Hu C, Chen X, Yao M, Yan M, Jiang G, Ge C, Xie H, Wan D, Yang S, Zheng S, Gu J (2007). CD133 positive hepatocellular carcinoma cells possess high capacity for tumorigenicity. Int. J Cancer 120, 1444-1450.

Zhang X, Kedl R M, Xiang J (2009). CD40 ligation converts TGF-beta-secreting tolerogenic CD4-8-dendritic cells into IL-12-secreting immunogenic ones. Biochem. Biophys. Res Commun. 379, 954-958.

Zhao C, Chen A, Jamieson C H, Fereshteh M, Abrahamsson A, Blum J, Kwon H Y, Kim J, Chute J P, Rizzieri D, Munchhof M, Vanarsdale T, Beachy P A, Reya T (2009). Hedgehog signalling is essential for maintenance of cancer stem cells in myeloid leukaemia. Nature.

Zhen H N, Zhang X, Hu P Z, Yang T T, Fei Z, Zhang J N, Fu L A, He X S, Ma F C, Wang X L (2005). Survivin expression and its relation with proliferation, apoptosis, and angiogenesis in brain gliomas. Cancer 104, 2775-2783, Zhou L, Lopes J E, Chong M M, Ivanov I I, Min R, Victora G D, Shen Y, Du J, Rubtsov Y P, Rudensky A Y, Ziegler S F, Littman D R (2008). TGF-beta-induced Foxp3 inhibits T(H)17 cell differentiation by antagonizing RORgammat function. Nature 453, 236-240.

Zhu K J, Cen J P, Lou J X, Wang Q, Zhang X, Xu Y, Chen X Z, Cheng H (2009). Imiquimnod inhibits the differentiation but enhances the maturation of human monocyte-derived dendritic cells. Int Immunopharmacol. 9, 412-417.

The invention claimed is:

1. A method of identifying a T cell receptor specific for a complex of a peptide and an MHC molecule, comprising:
   (a) providing a complex of a peptide and an MHC molecule, wherein the peptide consists of a sequence selected from the group consisting of SEQ ID NO:1 to SEQ ID NO:10, SEQ ID NO:20, and SEQ ID NO:24, wherein the MHC molecule is HLA-A*024;
   (b) providing a negative control complex comprising the MHC molecule;
   (c) isolating CD8+ enriched PBMCs comprising a T cell bearing a T cell receptor, wherein the T cell receptor is expressed on the surface of the T cell;
   (d) detecting a binding between the complex of (a) and the T cell receptor of (c) and a binding between the complex of (b) and the T cell receptor of (c); and
   (e) identifying the T cell receptor specific for the complex of (a) when the percent binding between the complex of (a) and the T cell receptor of (c) in the isolated CD8+ T cells is at least 10 times greater than the percent binding between the complex of (b) and the T cell receptor of (c).

2. The method of claim 1, wherein the specific binding between the complex of (a) and the T cell receptor of (c) induces a T-cell response in the T cell.

3. The method of claim 2, wherein the T cell response is selected from the group consisting of proliferation, lysis of peptide-presenting target cells that express complexes of HLA-A*024 and a peptide consisting of the sequence selected from the group consisting of SEQ ID NO: 1 to SEQ ID NO: 10, SEQ ID NO: 20 and SEQ ID NO: 24, secretion of cytokines and secretion of effector molecules.

4. The method of claim 1, wherein the percent binding is determined by flow cytometry analysis.

* * * * *